(12) United States Patent
Wang et al.

(10) Patent No.: US 11,267,810 B2
(45) Date of Patent: Mar. 8, 2022

(54) AMINOPYRIMIDINE COMPOUND AND COMPOSITION COMPRISING SAME AND USE THEREOF

(71) Applicant: Shenzhen TargetRx, Inc., Guangdong (CN)

(72) Inventors: Yihan Wang, Guangdong (CN); Huanyin Li, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 78 days.

(21) Appl. No.: 16/641,715

(22) PCT Filed: Aug. 21, 2018

(86) PCT No.: PCT/CN2018/101471
§ 371 (c)(1),
(2) Date: Feb. 25, 2020

(87) PCT Pub. No.: WO2019/042187
PCT Pub. Date: Mar. 7, 2019

(65) Prior Publication Data
US 2020/0207751 A1    Jul. 2, 2020

(30) Foreign Application Priority Data
Aug. 30, 2017    (CN) .......................... 201710765745.0

(51) Int. Cl.
| | |
|---|---|
| *C07D 413/14* | (2006.01) |
| *A61P 35/00* | (2006.01) |
| *A61P 3/00* | (2006.01) |
| *A61P 9/00* | (2006.01) |
| *A61P 29/00* | (2006.01) |
| *A61P 31/00* | (2006.01) |
| *A61P 31/12* | (2006.01) |
| *A61P 35/02* | (2006.01) |
| *A61P 37/06* | (2006.01) |
| *A61P 11/00* | (2006.01) |
| *A61P 11/02* | (2006.01) |
| *A61P 11/06* | (2006.01) |
| *A61P 11/08* | (2006.01) |

(Continued)

(52) U.S. Cl.
CPC ............ *C07D 413/14* (2013.01); *A61P 35/00* (2018.01)

(58) Field of Classification Search
CPC ..... C07D 413/14; C07D 403/04; A61P 35/00; A61P 3/00; A61P 9/00; A61P 29/00; A61P 31/00; A61P 31/12; A61P 35/02; A61P 37/06; A61P 37/00; A61P 19/02; A61P 19/06; A61P 11/06; A61P 11/00; A61P 11/02; A61P 11/08; C07B 2200/05; C07B 59/002
See application file for complete search history.

(56) References Cited

U.S. PATENT DOCUMENTS

| | | | |
|---|---|---|---|
| 9,593,098 B2 | 3/2017 | Suh | |
| 2016/0102076 A1* | 4/2016 | Suh | ........................ A61P 35/00 514/210.2 |

FOREIGN PATENT DOCUMENTS

| | | |
|---|---|---|
| CN | 106008639 A | 10/2016 |
| CN | 106795144 A | 5/2017 |

(Continued)

OTHER PUBLICATIONS

Sun, J-M. "Osimertinib for the treatment of non-small cell lung cancer." Expert opinion on pharmacotherapy 18.2 (2017): 225-231.*

(Continued)

*Primary Examiner* — John M Mauro
(74) *Attorney, Agent, or Firm* — Wolf, Greenfield & Sacks, P.C.

(57) ABSTRACT

Provided are an aminopyrimidine compound as shown in formula (I), a polymorph, a pharmaceutically acceptable salt, a prodrug, a stereoisomer, an isotopic variant, a hydrate or a solvate thereof, and a pharmaceutical composition containing the same and the use thereof. The aminopyrimidine compound and the composition containing the same have excellent inhibition to protein kinases, and at the same time have better pharmacokinetic parameter characteristics, and can improve the drug concentration of the compound in animals, and thereby improve the efficacy and safety of the drug.

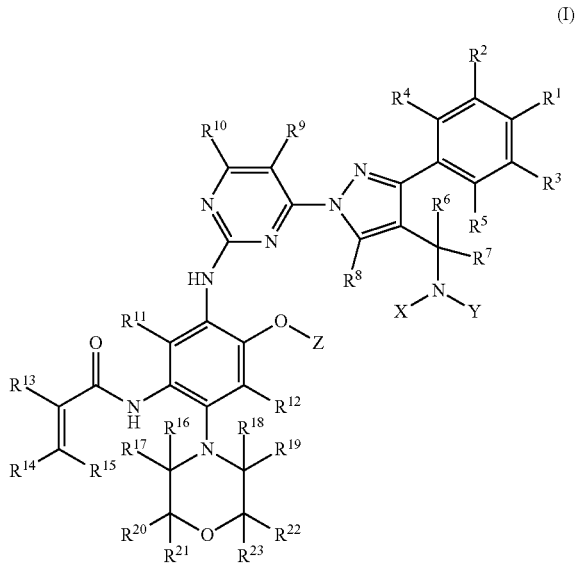

16 Claims, No Drawings

(51) Int. Cl.
　　　*A61P 19/02*　　(2006.01)
　　　*A61P 19/06*　　(2006.01)
　　　*A61P 37/00*　　(2006.01)
　　　*C07B 59/00*　　(2006.01)
　　　*C07D 403/04*　　(2006.01)

(56) References Cited

FOREIGN PATENT DOCUMENTS

| EP | 18849590.7 | 5/2020 |
|----|------------|--------|
| WO | WO 95/26325 A2 | 10/1995 |
| WO | WO 2016/054987 A1 | 4/2016 |
| WO | WO 2016/060443 A2 | 4/2016 |

OTHER PUBLICATIONS

Chinese Office Action for Application No. CN202010353107.X, dated Nov. 27, 2020.

Extended European Search Report for Application No. 18849590.7, dated May 20, 2020.

[No Author Listed] Precision Deuterium Chemistry Backgrounder. Concert Pharmaceuticals. 2009. pp. 1-6. URL:http://www.concertpharma.com/about/documents/ConcertProductPlatformBackgrounder.pdf [retrieved on Apr. 30, 2013].

Dumont, Prospects in the Use Of Deuterated Molecules as Therapeutic Agents. Revue IRE, Institut National Des Radioelements, Belgium. Jan. 1982;6(4):2-10.

Foster, Deuterium Isotope Effects in the Metabolism of Drugs and Xenobiotics: Implications for Drug Design. Advances in Drug Research. Jan. 1985;14:1-40.

O'Driscoll, Heavyweight Drugs. Chemistry & Industry, Society of Chemical Industry. Mar. 9, 2009:24-6.

Yarnell, Heavy-Hydrogen Drugs Turn Heads, Again. Science & Technology. Jun. 22, 2009;87(25):36-9. URL:http://pubs.acs.org/cen/science/87/8725scil .html [retrieved on Sep. 16, 2009].

* cited by examiner

AMINOPYRIMIDINE COMPOUND AND COMPOSITION COMPRISING SAME AND USE THEREOF

CROSS REFERENCE TO RELATED APPLICATIONS

The present application is a national application of PCT/CN2018/101471 filed on Aug. 21, 2018, which claims the priority of the Chinese Patent Application No. 201710765745.0 filed on Aug. 30, 2017. The Chinese Patent Application No. 201710765745.0 is incorporated herein by reference as part of the disclosure of the present application.

FIELD OF THE INVENTION

The present disclosure relates to the field of pharmaceutical technology, particularly relates to an aminopyrimidine compound, a composition comprising the same and use thereof. More specifically, the present disclosure relates to some deuterated N-(5-((4-(4-((dimethylamino)methyl)-3-phenyl-1H-pyrazol-1-yl)pyrimidin-2-yl)amino)-4-methoxy-2-morpholinophenyl)acrylamides. These deuterated compounds and compositions thereof can be used for the treatment of diseases mediated by certain mutant forms of EGFR, and have better pharmacokinetic properties.

BACKGROUND OF THE INVENTION

EGFR tyrosine kinase inhibitor (EGFR-TKI) is a molecular targeted drug targeting EGFR, which mainly blocks the further transmitting of signal into the cell by competitively binding to the binding site of the EGFR tyrosine kinase catalytic domain located on the cell surface with ATP, thereby inhibiting the growth of tumor cells and inducing their apoptosis. At present, EGFR-TKIs such as gefitinib and erlotinib have been widely used in the clinical practice. Although EGFR inhibitors such as gefitinib and erlotinib have achieved remarkable therapeutic effects against EGFR-mutant, advanced non-small cell lung cancer (NSCLC), these existing EGFR-TKIs were later found to encounter primary resistance or secondary resistance in the treatment of NSCLC. Therefore, the treatment of advanced NSCLC is facing new challenges, which needs our continuous new exploration and finding of new countermeasures.

Bruton's tyrosine kinase (BTK) is a member of the TEC family of tyrosine kinases, which plays an important role in the B cell activation and cell signaling BTK plays an indispensable role in the B cell signaling pathway, which connects the B cell receptor stimulators on the surface of B cells with the responders in the downstream cells. In addition, BTK is known to be a key regulator of the formation of B cells as well as the activation and survival of the mature B cells. Therefore, inhibiting BTK can be a key regulator to block the formation of B cells and the activation and survival of the mature B cells. Thus, the inhibition of BTK can be a therapeutic approach to block the process of the B cell-mediated disease. For example, abnormal signaling may induce the dysregulated B-cell proliferation and differentiation, thereby becoming the treatment of all types of lymphoma, including various acute or chronic lymphocytic leukemias; and may lead to the formation of autoantibodies, thereby becoming the treatment of inflammatory diseases, autoimmune diseases and/or immune-mediated diseases.

At the same time, T cells play a role in the signaling by activating various intercellular kinases (e.g. Janus kinase), and such signals are transmitted by antigen-presenting cells to downstream effectors through T cell receptors on the cell surface. At this time, they secrete various interleukins or interferon-γ to activate various leukocytes and B cells. The protein kinases involved in the T cell signal transduction are Janus kinases (JAKs, such as JAK1, JAK2, JAK3 and TYK2), IL-2 inducible T cell kinase (ITK) and TEC family kinases (e.g. Resting Lymphocyte Kinase, RLK). JAK3 inhibitors can be used to treat rheumatoid arthritis, psoriasis, allergic dermatitis, lupus, multiple sclerosis, type I diabetes and complications of diabetes, cancer, asthma, autoimmune thyroid disease, ulcerative colitis, Crohn's disease, Alzheimer's disease, leukemia and other indications in which immunosuppressants are beneficial (such as organ transplantation or xenotransplantation).

In WO2016060443A1, a novel compound YH25448 (its chemical name is N-(5-((4-(4-((dimethylamino)methyl)-3-phenyl-1H-pyrazol-1-yl)pyrimidin-2-yl)amino)-4-methoxy-2-morpholinophenyl)acrylamide with the following structural formula) was disclosed. It has significant inhibitory activity against EGFR mutant kinase.

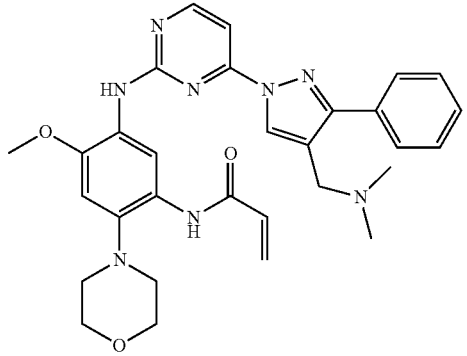

YH25448

Poor absorption, distribution, metabolism, and/or excretion (ADME) properties are known to be the primary causes of clinical trial failure of many drug candidates. At present, many marketed drugs have limitations on their application due to their poor ADME properties. The rapid metabolism of many drugs, which could have been effective in treating diseases, could make them difficult to be used as drugs due to their rapid removal from the body. Although a frequent or high-dose administration may solve the problem of rapid drug clearance, this approach will bring problems such as poor compliance of patients, side effects caused by high-dose administration and increased treatment costs. In addition, drugs that are rapidly metabolized may also expose the patients to undesirable toxic or reactive metabolites.

Therefore, it is still necessary to develop a compound with higher specificity and/or better pharmacodynamic/pharmacokinetic properties in this field.

SUMMARY OF THE INVENTION

In view of the above technical problems, the present disclosure provides an aminopyrimidine compound, a composition comprising the same and use thereof. The compounds have protein kinase inhibitory activity and better pharmacodynamic/pharmacokinetic properties.

In this regard, the technical solution adopted by the present disclosure is as follows:

In one aspect, the present disclosure relates to an aminopyrimidine compound of formula (I), or a polymorph, pharmaceutically acceptable salt, prodrug, stereoisomer, isotopic variants, hydrate or solvate thereof:

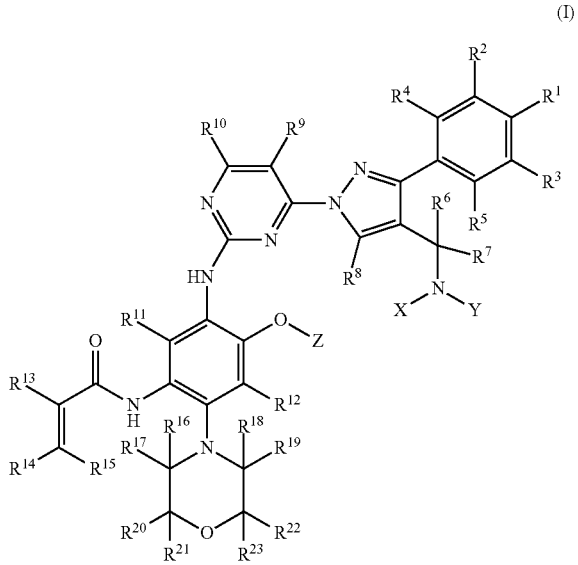

(I)

wherein, $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}$ and $R^{23}$ are independently selected from hydrogen, deuterium or halogen;

X, Y and Z are independently selected from the group consisting of $CH_3$, $CH_2D$, $CHD_2$ and $CD_3$.

As a preferred embodiment of the present disclosure, the compound of formula (I) contains at least one deuterium atom, more preferably one deuterium atom, more preferably two deuterium atoms, more preferably three deuterium atoms, more preferably six deuterium atoms, and more preferably nine deuterium atoms.

As a preferred embodiment of the present disclosure, the content of deuterium isotope in each deuterated position is at least greater than the natural content of deuterium isotope (0.015%), preferably greater than 30%, more preferably greater than 50%, more preferably greater than 75%, more preferably greater than 95%, and more preferably greater than 99%.

Specifically, in the present disclosure, the content of the deuterium isotope in each deuterated position of $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}$ and $R^{23}$, X, Y and Z is at least 5%, preferably greater than 10%, more preferably greater than 15%, more preferably greater than 20%, more preferably greater than 25%, more preferably greater than 30%, more preferably greater than 35%, more preferably greater than 40%, more preferably greater than 45%, more preferably greater than 50%, more preferably greater than 55%, more preferably greater than 60%, more preferably greater than 65%, more preferably greater than 70%, more preferably greater than 75%, more preferably greater than 80%, more preferably greater than 85%, more preferably greater than 90%, more preferably greater than 95%, and more preferably greater than 99%.

In another specific embodiment, among $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}, R^{19}, R^{20}, R^{21}, R^{22}$ and $R^{23}$, X, Y and Z of the compound of formula (I), at least one of them contains deuterium, more preferably two contain deuterium, more preferably three contain deuterium, more preferably four contain deuterium, more preferably five contain deuterium, more preferably six contain deuterium, more preferably seven contain deuterium, more preferably eight contain deuterium, more preferably nine contain deuterium, more preferably ten contain deuterium, more preferably eleven contain deuterium, more preferably twelve contain deuterium, more preferably thirteen contain deuterium, more preferably fourteen contain deuterium, more preferably fifteen contain deuterium, more preferably sixteen contain deuterium, more preferably seventeen contain deuterium, more preferably eighteen contain deuterium, more preferably nineteen contain deuterium, more preferably twenty contain deuterium, more preferably twenty-one contain deuterium, more preferably twenty-two contain deuterium, and more preferably twenty-three contain deuterium. Specifically, the compound of formula (I) contains at least one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight and twenty-nine deuterium atoms.

As a preferred embodiment of the present disclosure, $R^1$, $R^2$, $R^3$, $R^4$, and $R^5$ are independently selected from deuterium or hydrogen.

In another preferred embodiment, $R^1$, $R^2$, $R^3$, $R^4$, and $R^5$ are deuterium.

As a preferred embodiment of the present disclosure, $R^6$ and $R^7$ are independently selected from deuterium or hydrogen.

In another preferred embodiment, $R^6$ and $R^7$ are deuterium.

As a preferred embodiment of the present disclosure, $R^8$, $R^9$, $R^{10}$, $R^{11}$, $R^{12}$, $R^{13}$, $R^{14}$, $R^{15}$ are independently selected from deuterium or hydrogen.

In another preferred embodiment, $R^8$, $R^9$, $R^{10}$, $R^{11}$, $R^{12}$, $R^{13}$, $R^{14}$, $R^{15}$ are deuterium.

As a preferred embodiment of the present disclosure, $R^{16}$, $R^{17}$, $R^{18}$, $R^{19}$, $R^{20}$, $R^{21}$, $R^{22}$ and $R^{23}$ are independently selected from deuterium or hydrogen.

In another preferred embodiment, $R^{16}$, $R^{17}$, $R^{18}$, $R^{19}$, $R^{20}$, $R^{21}$, $R^{22}$ and $R^{23}$ are deuterium.

As a preferred embodiment of the present disclosure, X, Y and Z are independently methyl substituted with one or more deuteriums.

In another preferred embodiment, X, Y and Z are methyl substituted with three deuteriums ($CD_3$).

In another aspect, the present disclosure also provides a pharmaceutical composition, which comprises a pharmaceutically acceptable excipient and the aminopyrimidine compound as described above, or the polymorph, pharmaceutically acceptable salt, prodrug, stereoisomer, isotopic variants, hydrate or solvate thereof.

In another aspect, the present disclosure also provides a method of preparing the pharmaceutical composition described above, comprising the steps of: mixing the pharmaceutically acceptable excipient(s) and the aminopyrimidine compound as described above, or the polymorph, pharmaceutically acceptable salt, prodrug, stereoisomer, isotopic variants, hydrate or solvate thereof, thereby forming the pharmaceutical composition.

In another embodiment, the pharmaceutical composition is an injection, a capsule, a pill, a tablet, a powder or a granule.

In another embodiment, the pharmaceutical composition also includes other therapeutic drugs, which are drugs for cancer, cardiovascular disease, inflammation, infection, immune disease, cell proliferative disease, viral disease, metabolic disease or organ transplantation.

In another aspect, the present disclosure also provides a use of the compound in the first aspect disclosed herein, or a polymorph, pharmaceutically acceptable salt, prodrug, stereoisomer, isotopic variants, hydrate or solvate thereof, in the preparation of a medicament for the treatment and/or prevention of the diseases related to protein kinases.

In another aspect, the present disclosure also provides a method of treating and/or preventing a protein kinase-related disease in a subject, comprising administering to the subject an aminopyrimidine compound of formula (I), or a polymorph, a pharmaceutically acceptable salt, a prodrug, a stereoisomer, an isotopic variants, a hydrate or a solvate thereof, or a pharmaceutical composition thereof.

In another aspect, the present disclosure also provides an aminopyrimidine compound of formula (I), or a polymorph, pharmaceutically acceptable salt, prodrug, stereoisomer, isotopic variants, hydrate or solvate thereof, or a pharmaceutical composition thereof, for use in treating and/or preventing the protein kinase-related diseases.

In another aspect, the present disclosure provides a method of treating a protein kinase-mediated disease in a subject, comprising administering to the subject a therapeutically effective amount of the compound described herein or a pharmaceutically acceptable salt thereof, which is effective in treating the abnormal cell growth and immune diseases.

In another aspect, the present disclosure provides a method of selectively inhibiting at least one EGFR mutant compared to a wild-type EGFR in a biological sample or a subject, comprising contacting the biological sample with the compound described herein or a composition thereof (such as a pharmaceutical composition comprising the compound described herein and a pharmaceutically acceptable carrier), or administering the compound described herein or a composition thereof to the subject. In some embodiments, the at least one mutant is del19, L858R or T790M. In some other embodiments, the at least one mutant is at least one double mutant selected from del19, L858R or T790M.

In another embodiment, the compound or the pharmaceutical composition is used to treat and/or prevent the following diseases: cancer, cell proliferative disease, inflammation, infection, immune disease, organ transplantation, viral disease, cardiovascular disease or metabolic disease.

In another embodiment, the cancer includes, but is not limited to, lung cancer, head and neck cancer, breast cancer, prostate cancer, esophageal cancer, rectal cancer, colon cancer, nasopharyngeal carcinoma, uterine cancer, pancreatic cancer, lymphoma, blood cancer, osteosarcoma, melanoma, kidney cancer, gastric cancer, liver cancer, bladder cancer, thyroid cancer or colorectal cancer.

In another embodiment, the immune disease or inflammation includes, but is not limited to, rheumatoid arthritis, osteoarthritis, rheumatoid spondylitis, gout, asthma, bronchitis, rhinitis, chronic obstructive pulmonary disease or cystic fibrosis.

In another embodiment, the cell proliferative disease refers to lung cancer, head and neck cancer, breast cancer, prostate cancer, esophageal cancer, rectal cancer, colon cancer, nasopharyngeal carcinoma, uterine cancer, pancreatic cancer, lymphoma, blood cancer, osteosarcoma, melanoma, kidney cancer, gastric cancer, liver cancer, bladder cancer, thyroid cancer or colorectal cancer.

In another embodiment, the cancer is non-small cell lung cancer.

In another embodiment, the protein kinase is selected from the group consisting of epidermal growth factor receptor (EGFR) tyrosine kinase or a mutant thereof, Bruton's tyrosine kinase (BTK), Janus kinase 3 (JAK3), interleukin-2 inducible T cell kinase (ITK), resting lymphocyte kinase (RLK) and bone marrow tyrosine kinase (BMX).

In another aspect, the present disclosure also provides a kit, which includes a first container containing an amide compound of formula (I), a polymorph, pharmaceutically acceptable salt, prodrug, stereoisomer, isotopic variants, hydrate or solvate thereof; and optionally, a second container containing other therapeutic drugs; and optionally, a third container containing a pharmaceutically acceptable excipient for diluting or suspending the compounds disclosed herein and/or other therapeutic drugs.

In another aspect, the present disclosure also provides a use of the aminopyrimidine compound described above in the preparation of a pharmaceutical composition for inhibiting the protein kinase. Preferably, it is used in the preparation of a pharmaceutical composition for inhibiting the EGFR kinase.

In addition, the compound of formula (I) or a polymorph, pharmaceutically acceptable salt, prodrug, stereoisomer, isotopic variants, hydrate or solvate thereof, may treat or prevent the diseases caused by the Bruton's tyrosine kinase (BTK), Janus kinase 3 (JAK3), interleukin-2 inducible T cell kinase (ITK), resting lymphocyte kinase (RLK) and bone marrow tyrosine kinase (BMX) expressed in an abnormally activated B-lymphocyte and/or T-lymphocyte.

The compound of formula (I) disclosed herein or a polymorph, pharmaceutically acceptable salt, prodrug, stereoisomer, isotopic variants, hydrate or solvate thereof, may treat or prevent the cancer, tumor, inflammatory disease, autoimmune disease or immune-mediated disease caused by an abnormally activated B lymphocyte, T lymphocyte or both. Therefore, the present disclosure also provides a pharmaceutical composition for treating and/or preventing cancer, tumor, inflammatory disease, autoimmune disease or immune-mediated disease, which comprises the compound of formula (I) disclosed herein or a polymorph, pharmaceutically acceptable salt, prodrug, stereoisomer, isotopic variant, hydrate or solvate thereof as the active ingredient.

Representative examples of the inflammatory disease, autoimmune disease and immune-mediated disease may include, but are not limited to, arthritis, rheumatoid arthritis, spinal arthritis, gouty arthritis, osteoarthritis, juvenile arthritis, other arthritic conditions, lupus, systemic lupus erythematosus (SLE), skin-related disease, psoriasis, eczema, dermatitis, allergic dermatitis, pain, lung disease, pulmonary inflammation, adult respiratory distress syndrome (ARDS), pulmonary sarcoidosis, chronic pulmonary inflammatory disease, chronic obstructive pulmonary disease (COPD), cardiovascular disease, atherosclerosis, myocardial infarction, congestive heart failure, myocardial ischemia reperfusion injury, inflammatory bowel disease, Crohn's disease, ulcerative colitis, irritable bowel syndrome, asthma, Sjogren's syndrome, autoimmune thyroid disease, urticaria, multiple sclerosis, scleroderma, organ transplantion rejection, xenotransplantation, idiopathic thrombocytopenic purpura, Parkinson's disease, Alzheimer's disease, diabetes-related disease, inflammation, pelvic inflammatory disease, allergic rhinitis, allergic bronchitis, allergic sinusitis, leukemia, lymphoma, B-cell lymphoma, T-cell lymphoma, myeloma, acute lymphocytic leukemia (ALL), chronic lymphocytic leukemia (CLL), acute myeloid leukemia (AML), chronic myeloid leukemia (CML), hairy cell leukemia, Hodgkin's disease, non-Hodgkin's lymphoma, multiple myeloma, myelodysplastic syndrome (MDS), myeloproliferative neoplasm (MPN), diffuse large B-cell lymphoma and follicular lymphoma.

When the compound of formula (I) disclosed herein or a polymorph, pharmaceutically acceptable salt, prodrug, stereoisomer, isotopic variants, hydrate or solvate thereof is administered in combination with another therapeutic agent for treating inflammatory disease, autoimmune disease and immune-mediated disease, the compound of formula (I) disclosed herein or a polymorph, pharmaceutically acceptable salt, prodrug, stereoisomer, isotopic variants, hydrate or solvate thereof may provide an enhanced therapeutic effect.

Representative examples of the other therapeutic agent used to treat inflammatory disease, autoimmune disease and immune-mediated disease may include, but are not limited to, steroid drug (e.g., prednisone, prednisolone, methyl prednisolone, cortisone, hydroxycortisone, betamethasone, dexamethasone, etc.), methotrexate, leflunomide, anti-TNFα agent (e.g., etanercept, infliximab, adalimumab, etc.), calcineurin inhibitor (e.g., tacrolimus, pimecrolimus, etc.) and antihistamine (e.g., diphenhydramine, hydroxyzine, loratadine, ebastine, ketotifen, cetirizine, levocetirizine, fexofenadine, etc.), and at least one therapeutic agent selected from them may be included in the pharmaceutical composition disclosed herein.

Also disclosed herein are isotopically labeled compounds (also referred to as "isotopic variants") to the extent of the original compounds disclosed herein. Examples of isotopes that can be listed in compounds disclosed herein include hydrogen, carbon, nitrogen, oxygen, phosphorus, sulfur, fluorine and chlorine isotopes, such as $^2$H, $^3$H, $^{13}$C, $^{14}$C, $^{15}$N, $^{17}$O, $^{18}$), $^{31}$P, $^{32}$P, $^{35}$S, $^{18}$F and $^{36}$Cl, respectively. A compound of formula (I) disclosed herein containing the above isotope or other isotopic atom, or a polymorph, a pharmaceutically acceptable salt, a prodrug, a stereoisomer, an isotopic variant, a hydrate or a solvate thereof are all within the scope disclosed herein. Certain isotopically labeled compounds disclosed herein, such as the radioisotopes of $^3$H and $^{14}$C, are also among them and are useful in the tissue distribution experiments of drugs and substrates. Tritium, i.e., $^3$H, and carbon-14, i.e., $^{14}$C, are easier to prepare and detect and are the first choice for isotopes. In addition, substitution with heavier isotopes such as deuterium, i.e., $^2$H, has advantages in some therapies due to its good metabolic stability, for example, increased half-life in vivo or reduced dosage, and thus priority may be given in some cases. Isotopically-labeled compounds can be prepared using the schemes shown in the Examples by conventional methods by replacing the non-isotopic reagents with readily available isotopically labeled reagents.

It is to be understood that within the scope disclosed herein, the above various technical features, embodiments and various technical features specifically described hereinafter (as in the examples) in the present disclosure may be combined with each other to constitute a new or preferred technical solution. Due to space limitations, we will not repeat them here.

Compared with the prior art, the present disclosure has the following beneficial effects: first, the aminopyrimidine compounds of the technical solutions disclosed herein have excellent inhibitory properties against protein kinases. Second, the metabolism of the compound in the organism is improved, allowing the compound to have better pharmacokinetic parameters. In this case, the dose may be changed and a long-acting formulation may be formed to improve the applicability. Third, the drug concentration of the compound in animals is increased, so as to improve the efficacy of the drug. Fourth, the safety of the compound may be increased due to the inhibition of certain metabolites.

Definitions

When a range of values is listed, it is intended to encompass each value and sub-range within the range. For example "$C_1$-$C_6$ alkyl" is intended to encompass, $C_1$, $C_2$, $C_3$, $C_4$, $C_5$, $C_6$, $C_1$-$C_6$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$ and $C_5$-$C_6$ alkyl.

It should be understood that when described herein any of the moieties defined forth below may be substituted with a variety of substituents, and that the respective definitions are intended to include such substituted moieties within their scope as set out below. Unless otherwise stated, the term "substituted" is to be defined as set out below.

"Halogen" refers to fluorine (F), chlorine (Cl), bromine (Br) and iodine (I).

The term "polymorph" refers to the different arrangement of chemical drug molecules, which is generally presented as the existence form of the drug raw materials in the solid state. A drug may exist in a variety of crystal forms, and different crystal forms of the same drug may have different dissolution and absorption properties in vivo, thereby affecting the dissolution and release of the formulation.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66:1-19. Pharmaceutically acceptable salts of the compounds of the present disclosure include those derived from suitable inorganic and organic acids and inorganic and organic bases. Examples of pharmaceutically acceptable, nontoxic acid addition salts are salts formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Also included are salts formed by using conventional methods in the art, such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Other pharmaceutically acceptable salts include, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i. e., a male or female of any age group, e.g., a pediatric subject (e.g., infant, child, adolescent) or adult subject (e.g., young adult, middle-aged adult or senior adult)) and/or a non-human animal, e g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human", "patient" and "subject" can be used interchangeably herein.

"Disease", "disorder" and "condition" are used interchangeably herein.

The term "treatment" as used herein includes the effect on a subject who is suffering from a particular disease, disorder, or condition, which reduces the severity of the disease, disorder or condition, or delays or slows the progression of the disease, disorder or condition. The term "prevention" includes the effect that occurs before the subject begins to suffer from a specific disease, disorder or condition.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

The compound disclosed herein may include one or more asymmetric centers, and thus may exist in a variety of "stereoisomer" forms, for example, enantiomeric and/or diastereomeric forms. For example, the compound disclosed herein may be in the form of an individual enantiomer, a diastereomer or a geometric isomer (e.g., cis and trans isomers), or may be in the form of a mixture of stereoisomers, including a racemic mixture and a mixture enrich in one or more stereoisomers. The isomers can be separated from the mixture by methods known to those skilled in the art, including: chiral high pressure liquid chromatography (HPLC) and formation and crystallization of a chiral salt; or preferred isomers can be prepared by asymmetric synthesis.

Those skilled in the art will appreciate that many organic compounds can form complexes with solvents that react in or precipitate or crystallize from the solvent. These complexes are referred to as "solvates." When the solvent is water, the complex is referred to as a "hydrate." The invention encompasses all solvates of the compounds disclosed herein.

In addition, a prodrug is also included within the context disclosed herein. The term "prodrug" as used herein refers to a compound which is converted in vivo to an active form thereof having a medical effect by, for example, hydrolysis in blood. Pharmaceutically acceptable prodrugs are described in T. Higuchi and V. Stella, Prodrugs as Novel Delivery Systems, A.C.S. Symposium Series Vol. 14, Edward B. Roche, ed., Bioreversible Carriers in Drug Design, American Pharmaceutical Association and Pergamon Press, 1987, and D. Fleisher, S. Ramon, and H. Barbra "Improved oral drug delivery: solubility limitations overcome by the use of prodrugs", Advanced Drug Delivery Reviews (1996) 19(2) 115-130, each of which is incorporated herein by reference.

A prodrug is any covalently bonded carrier which, when administered to a patient, releases the compound disclosed herein in vivo. A prodrug is typically prepared by modifying a functional group of a drug that cleaves the prodrug in vivo to yield the parent compound. A prodrug includes, for example, a compound disclosed herein wherein a hydroxy, amino or mercapto group is bonded to any group which, when administered to a patient, can be cleaved to form a hydroxy, amino or mercapto group. Thus, representative examples of prodrugs include, but are not limited to, covalent derivatives of compounds of the present disclosure formed by the hydroxyl, amino or mercapto functional groups thereof with acetic acid, formic acid or benzoic acid. Further, in the case of a carboxylic acid (—COOH), an ester such as a methyl ester, an ethyl ester or the like may be used. The ester itself may be active and/or may be hydrolyzed in vivo under human body conditions. Suitable pharmaceutically acceptable in vivo hydrolysable esters include those which readily decompose in a human body to release a parent acid or its salt.

A "pharmaceutically acceptable excipient" for use in the present disclosure refers to a non-toxic carrier, adjuvant or vehicle that does not destroy the pharmacological activity of the compound formulated together. Pharmaceutically acceptable carriers, adjuvants, or vehicles that can be used in the compositions disclosed herein include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based substances, polyethylene glycol, sodium carboxymethyl cellulose, polyacrylate, wax, polyethylene-polyoxypropylene block polymer, polyethylene glycol and lanolin.

DETAILED DESCRIPTION OF THE INVENTION

Compounds

The present disclosure relates to an aminopyrimidine compound of formula (I), or a polymorph, pharmaceutically acceptable salt, prodrug, stereoisomer, isotopic variants, hydrate or solvate thereof:

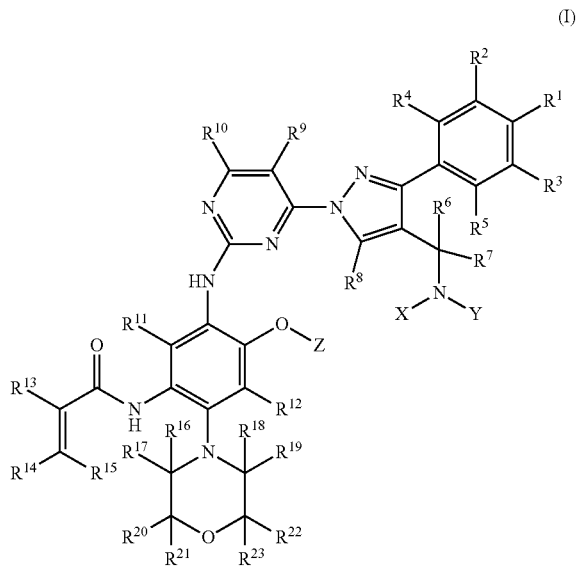

(I)

wherein,

R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ are independently selected from hydrogen, deuterium or halogen;

X, Y and Z are independently selected from the group consisting of CH$_3$, CH$_2$D, CHD$_2$ and CD$_3$;

with the proviso that the aminopyrimidine compound described above contains at least one deuterium atom.

In a specific embodiment, "R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$, R$^{20}$, R$^{21}$, R$^{22}$ and R$^{23}$ are independently selected from hydrogen, deuterium or halogen" includes the technical solutions wherein, R$^1$ is selected from hydrogen, deuterium or halogen, R$^2$ is selected from hydrogen, deuterium or halogen, R$^3$ is selected from hydrogen, deuterium or halogen and so on, until R$^{23}$ is selected from hydrogen, deuterium or halogen. More specifically, the technical solutions wherein, R$^{23}$ is hydrogen, R$^1$ is deuterium or R$^1$ is halogen (F, Cl, Br or I), R$^2$ is hydrogen, R$^2$ is deuterium or R$^2$ is halogen (F, Cl, Br or I), R$^3$ is hydrogen, R$^3$ is deuterium or R$^3$ is halogen (F, Cl, Br or I) and so on, until R$^{23}$ is hydrogen, R$^{23}$ is deuterium or R$^{23}$ is halogen (F, Cl, Br or I), are included.

In another specific embodiment, "X, Y and Z are independently selected from the group consisting of CH$_3$, CH$_2$D, CHD$_2$ and CD$_3$" includes the technical solutions wherein, X is CH$_3$, X is CH$_2$D, X is CHD$_2$ or X is CD$_3$, Y is CH$_3$, Y is CH$_2$D, Y is CHD$_2$ or Y is CD$_3$, Z is CH$_3$, Z is CH$_2$D, Z is CHD$_2$ or Z is CD$_3$.

As a preferred embodiment of the present disclosure, the present disclosure relates to a compound of formula (I), or a polymorph, pharmaceutically acceptable salt, prodrug, stereoisomer, isotopic variants, hydrate or solvate thereof, wherein, R$^9$ to R$^{15}$ are hydrogen, R$^1$ to R$^8$ and R$^{16}$ to R$^{23}$ are independently selected from hydrogen or deuterium, X, Y and Z are independently selected from CH$_3$, CH$_2$D, CHD$_2$ or CD$_3$, with the proviso that the compound described above contains at least one deuterium atom.

As a preferred embodiment of the present disclosure, the present disclosure relates to a compound of formula (I), or a polymorph, pharmaceutically acceptable salt, prodrug, stereoisomer, isotopic variants, hydrate or solvate thereof, wherein, R$^9$ to R$^{23}$ are hydrogen, R$^1$ to R$^8$ are independently selected from hydrogen or deuterium, X, Y and Z are independently selected from CH$_3$, CH$_2$D, CHD$_2$ or CD$_3$, with the proviso that the compound described above contains at least one deuterium atom.

As a preferred embodiment of the present disclosure, the present disclosure relates to a compound of formula (I), or a polymorph, pharmaceutically acceptable salt, prodrug, stereoisomer, isotopic variants, hydrate or solvate thereof, wherein, R$^1$ to R$^5$ and R$^9$ to R$^{23}$ are hydrogen, R$^6$ to R$^8$ are independently selected from hydrogen or deuterium, X, Y and Z are independently selected from CH$_3$, CH$_2$D, CHD$_2$ or CD$_3$, with the proviso that the compound described above contains at least one deuterium atom.

As a preferred embodiment of the present disclosure, the present disclosure relates to a compound of formula (I), or a polymorph, pharmaceutically acceptable salt, prodrug, stereoisomer, isotopic variants, hydrate or solvate thereof, wherein, R$^6$ to R$^{23}$ are hydrogen, R$^1$ to R$^5$ are independently selected from hydrogen or deuterium, X, Y and Z are independently selected from CH$_3$, CH$_2$D, CHD$_2$ or CD$_3$, with the proviso that the compound described above contains at least one deuterium atom.

As a preferred embodiment of the present disclosure, the present disclosure relates to a compound of formula (I), or a polymorph, pharmaceutically acceptable salt, prodrug, stereoisomer, isotopic variants, hydrate or solvate thereof, wherein, R$^1$ to R$^{23}$ are hydrogen, X, Y and Z are independently selected from CH$_3$, CH$_2$D, CHD$_2$ or CD$_3$, with the proviso that the compound described above contains at least one deuterium atom.

As a preferred embodiment of the present disclosure, the present disclosure relates to a compound of formula (I), or a polymorph, pharmaceutically acceptable salt, prodrug, stereoisomer, isotopic variants, hydrate or solvate thereof, wherein, R$^1$ to R$^{23}$ are hydrogen, X and Y are CH$_3$, and Z is CD$_3$.

As a preferred embodiment of the present disclosure, R$^1$ to R$^5$ are the same.

As a preferred embodiment of the present disclosure, R$^6$ to R$^8$ are the same.

As a preferred embodiment of the present disclosure, the amide compound is represented by any of the following structures, or a pharmaceutically acceptable salt thereof, but is not limited to the following structures:

Formula (1)

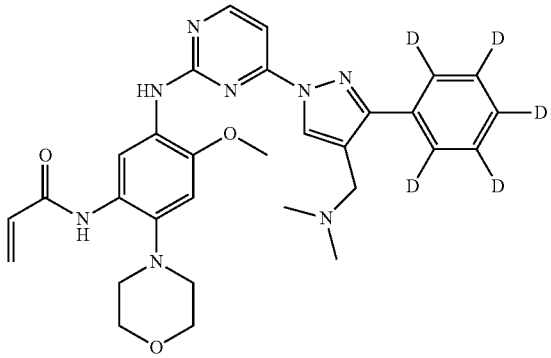

Formula (2)

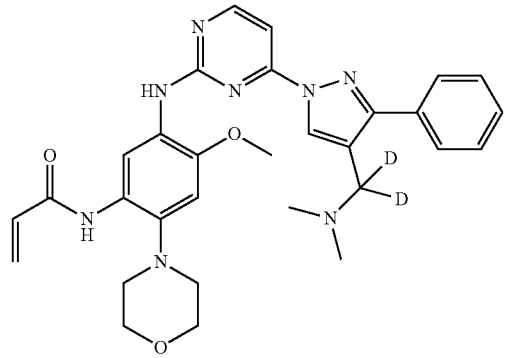

Formula (3)

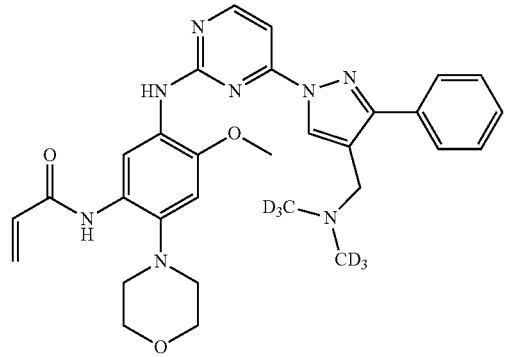

Formula (4)
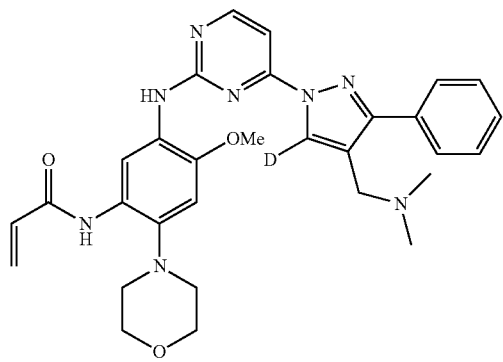
Formula (5)
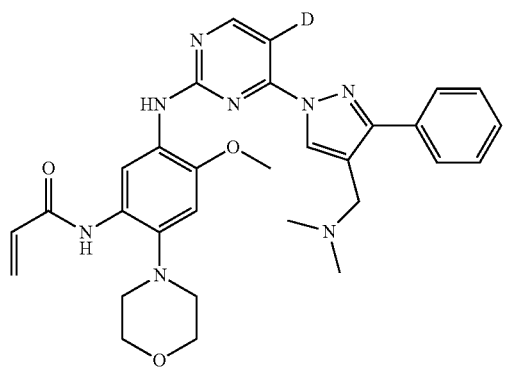
Formula (6)
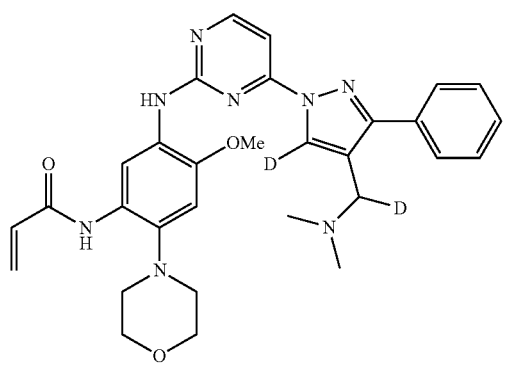
Formula (7)
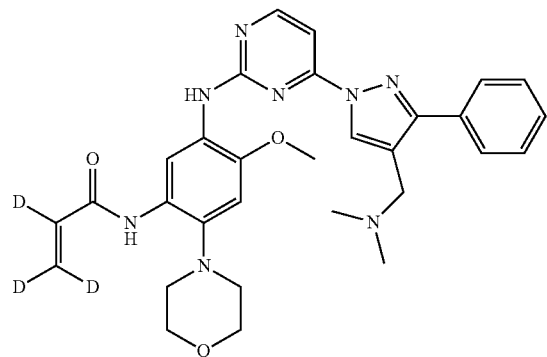
Formula (8)
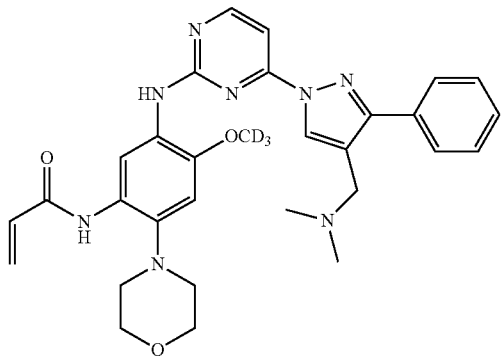
Formula (9)
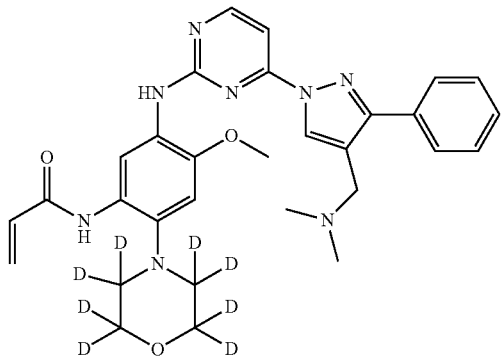
Formula (10)
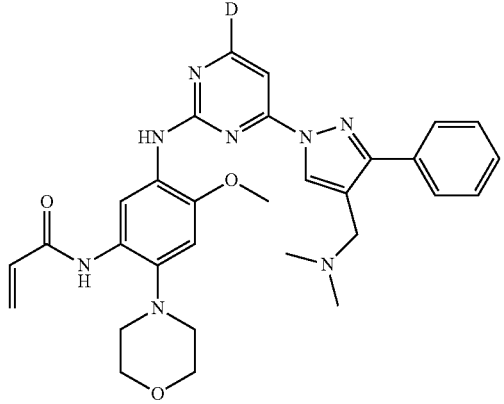
Formula (11)
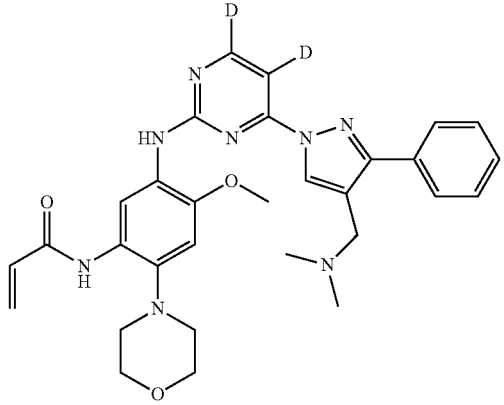

Formula (12)
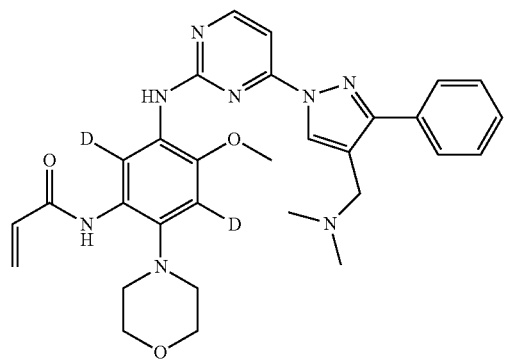
Formula (13)
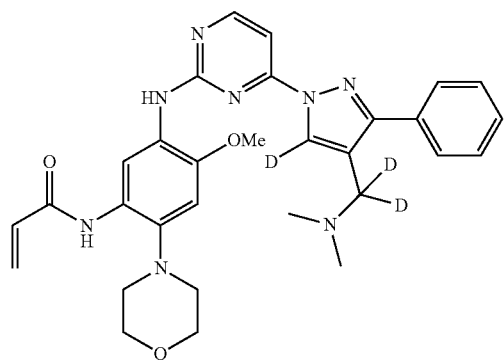
Formula (14)
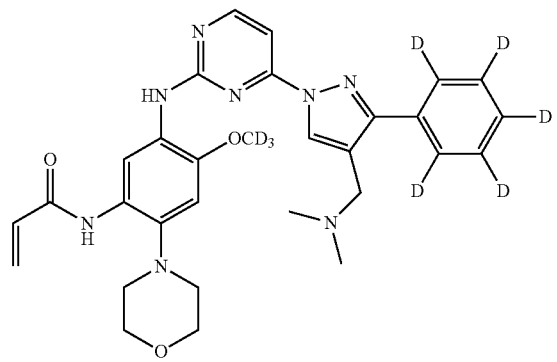
Formula (15)
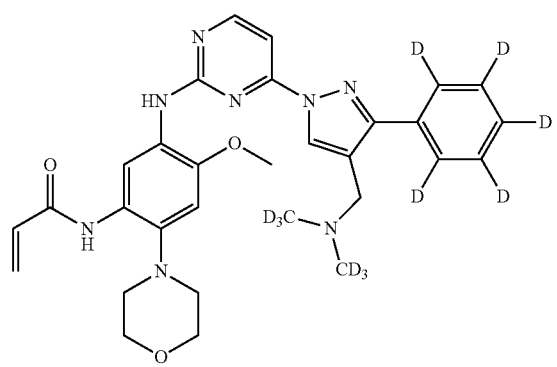
Formula (16)
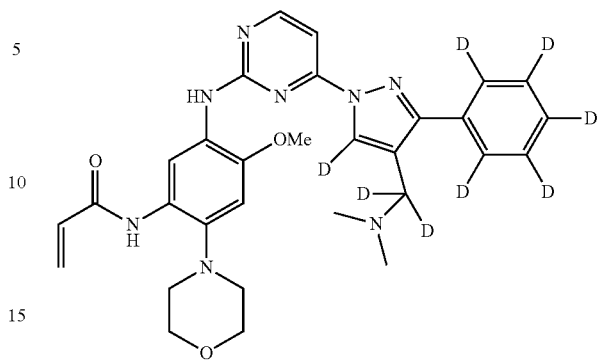
Formula (17)
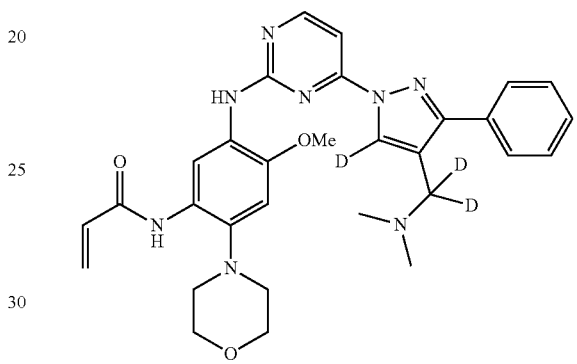
Formula (18)
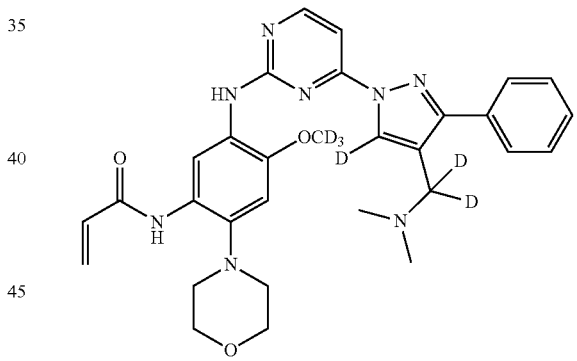
Formula (19)
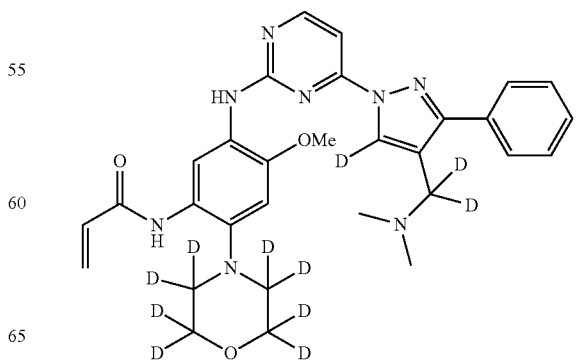

Formula (20)
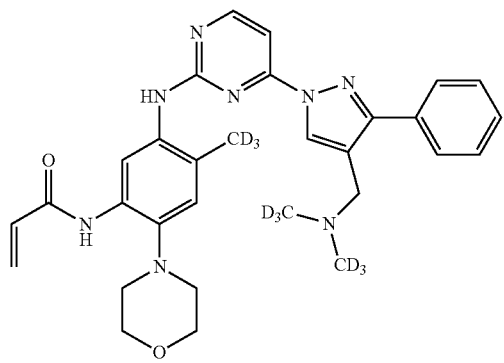
Formula (21)
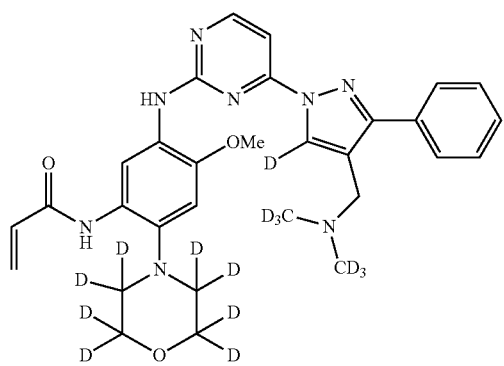
Formula (22)
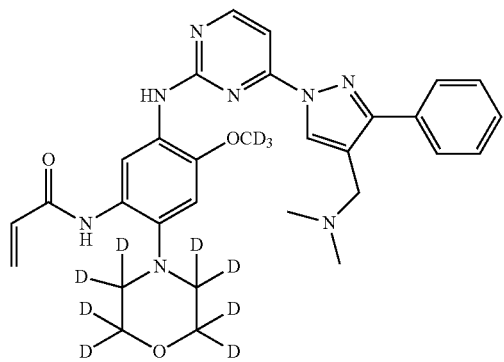
Formula (23)
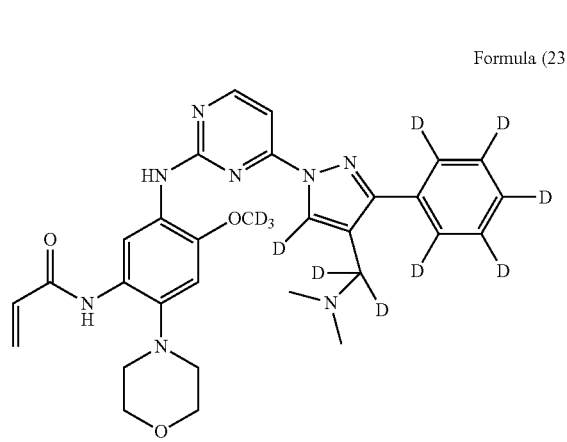
Formula (24)
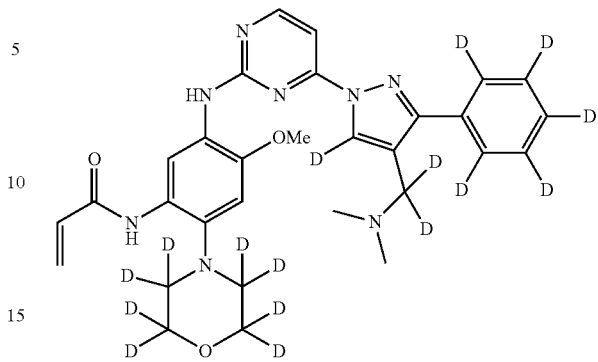
Formula (25)
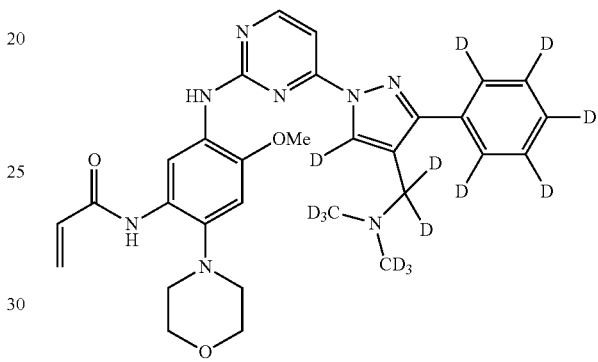
Formula (26)
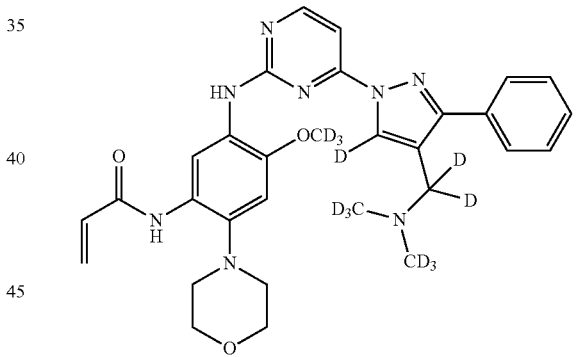
Formula (27)
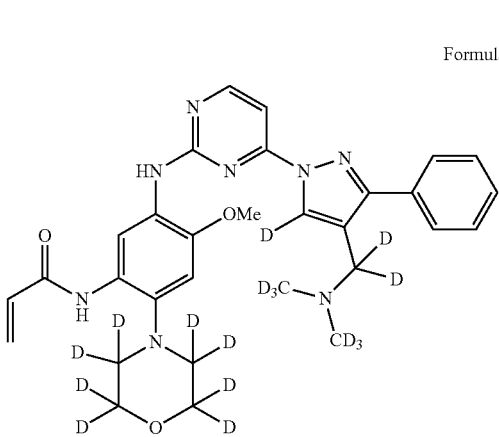

Formula (28)
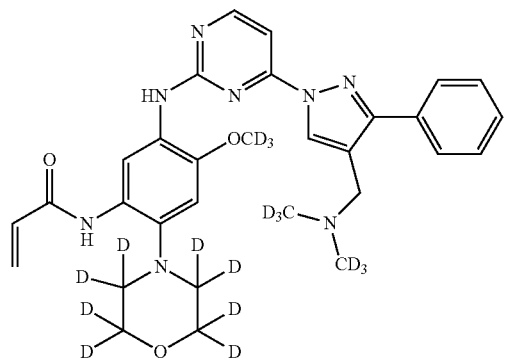
Formula (29)
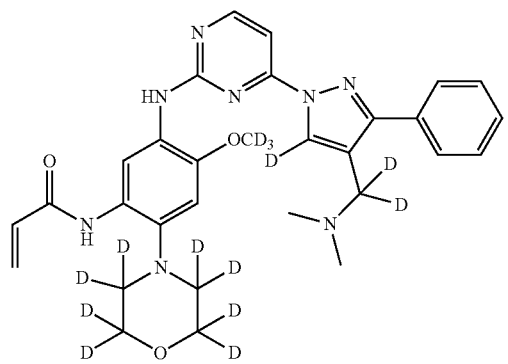
Formula (30)
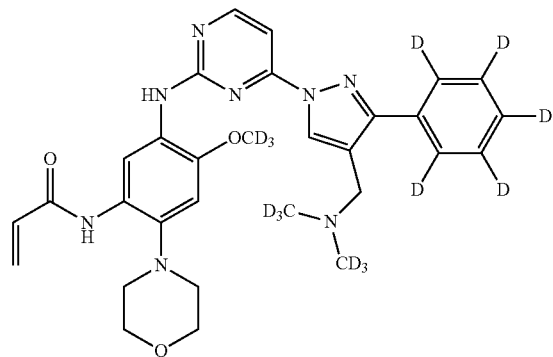
Formula (31)
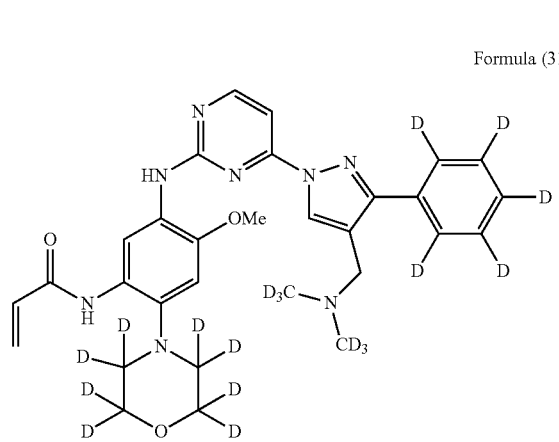
Formula (32)
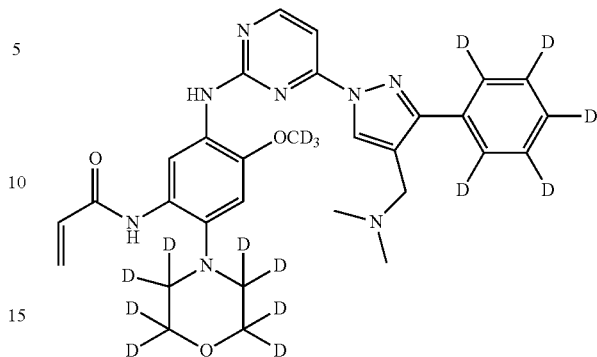
Formula (33)
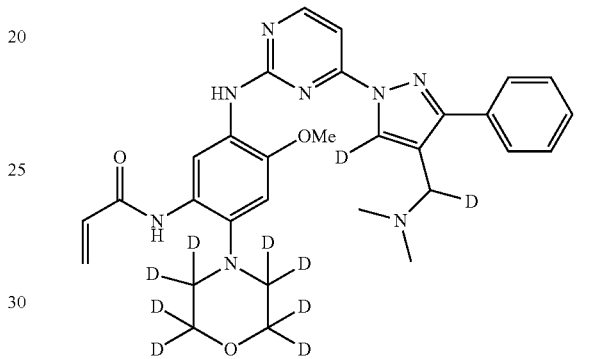
Formula (34)
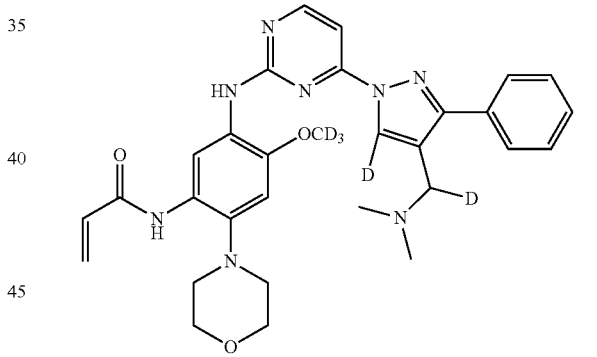
Formula (35)
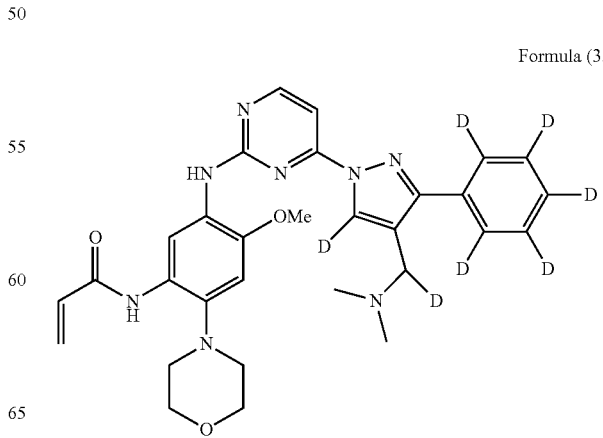

-continued
Formula (36)
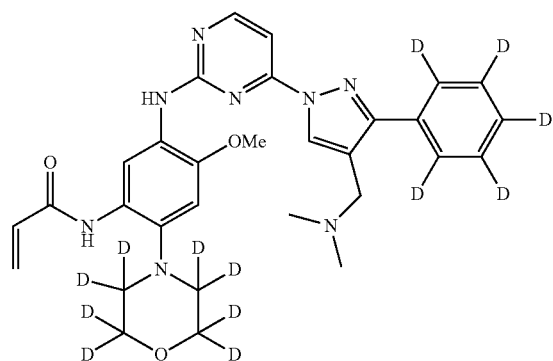
Formula (37)
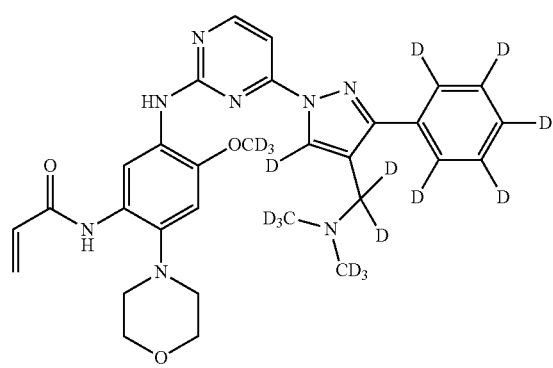
Formula (38)
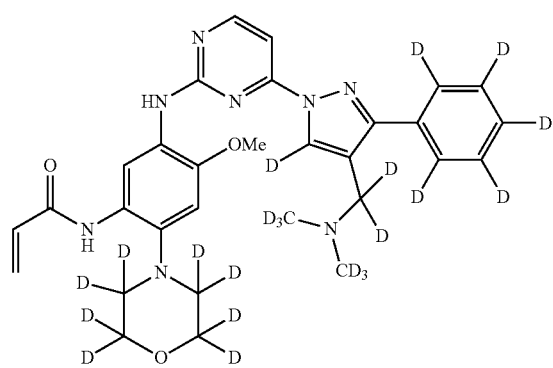
Formula (39)
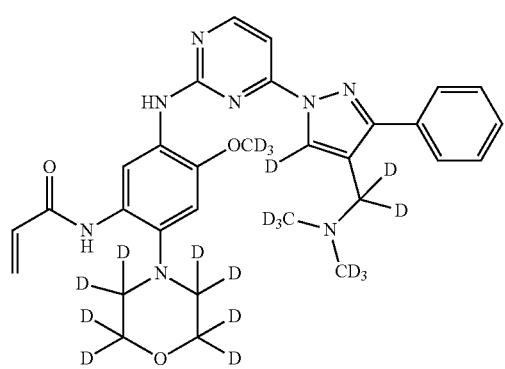
Formula (40)
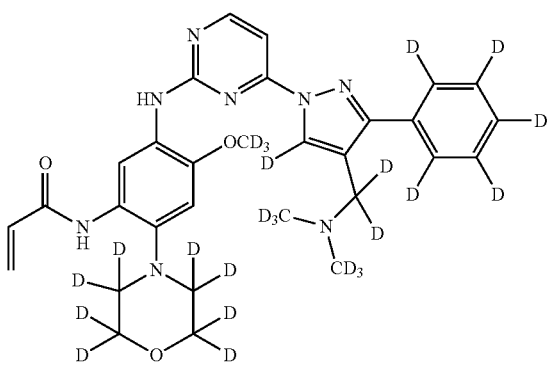
Formula (41)
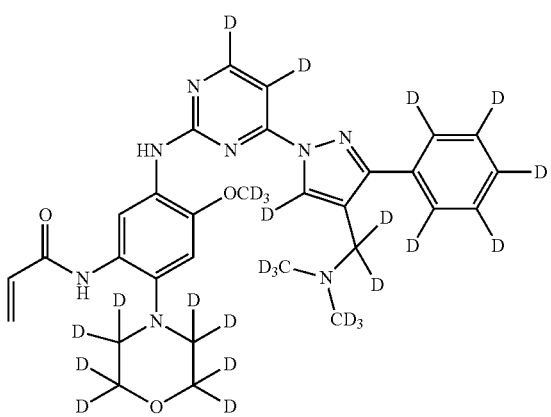
Formula (42)
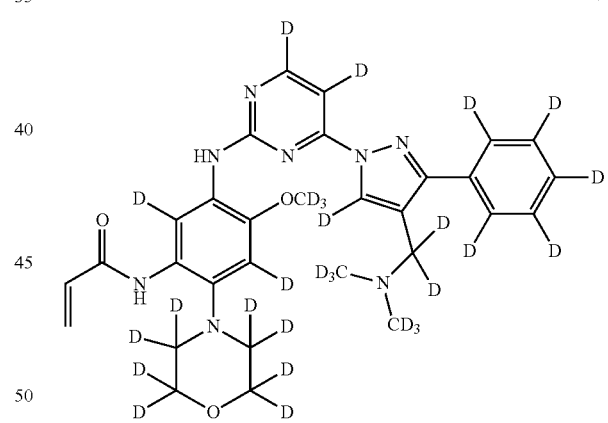
Formula (43)
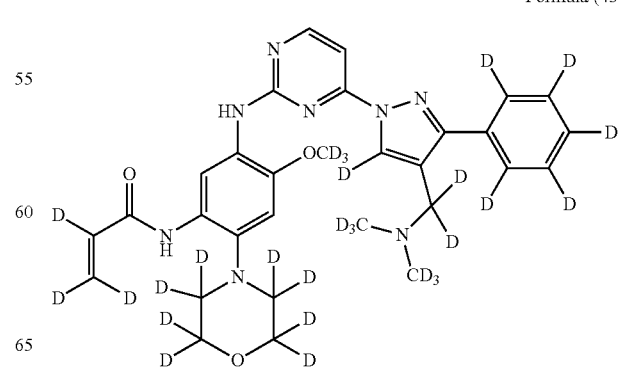

Formula (44)
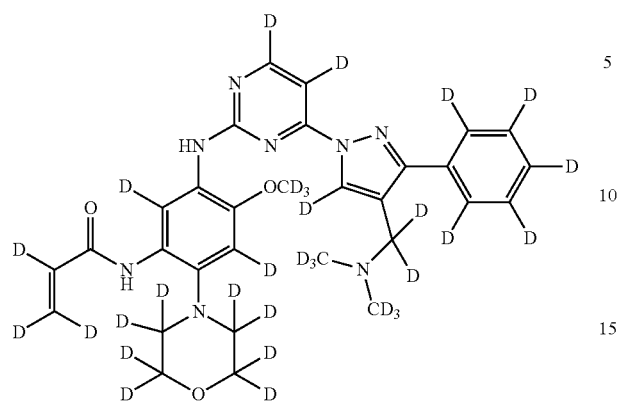
Formula (45)
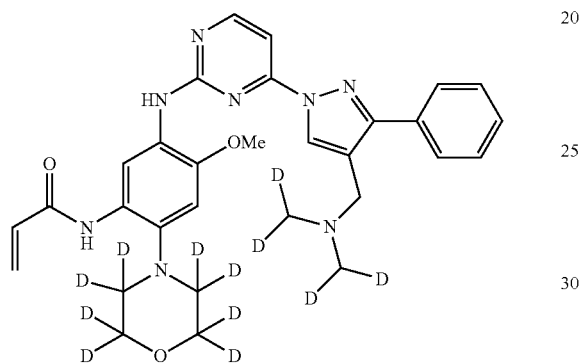
Formula (46)
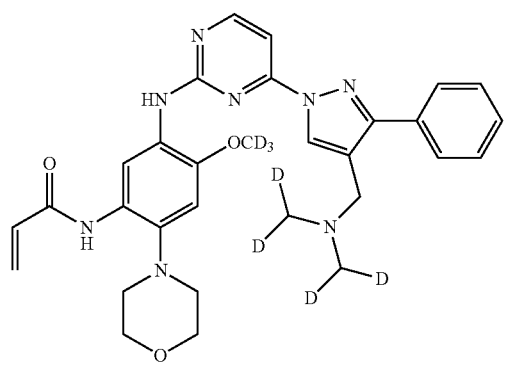
Formula (47)
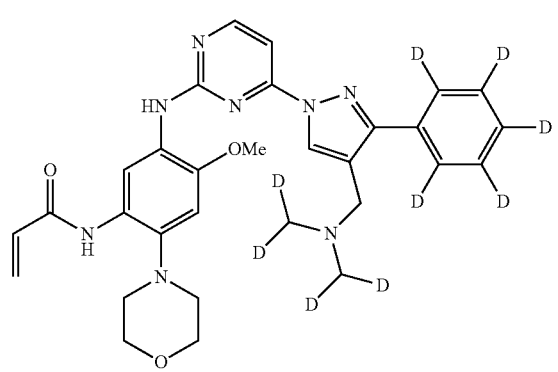
Formula (48)
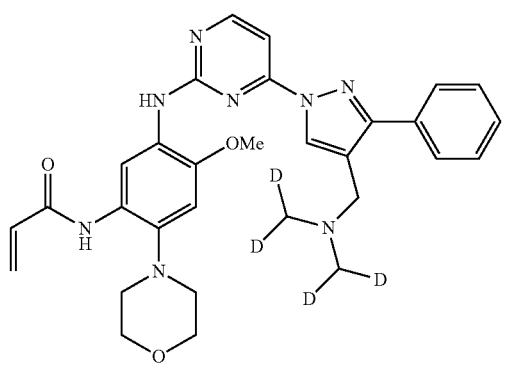
Formula (49)
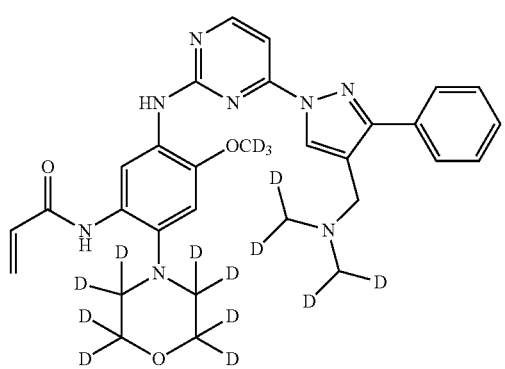
Formula (50)
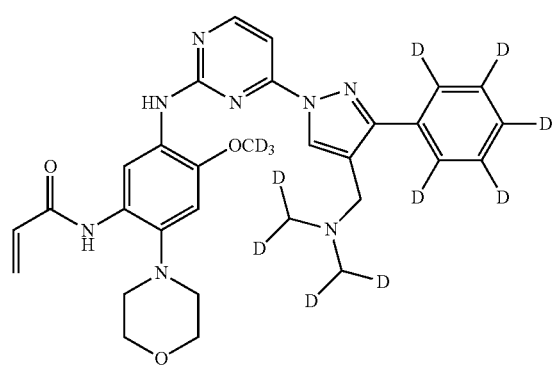
Formula (51)
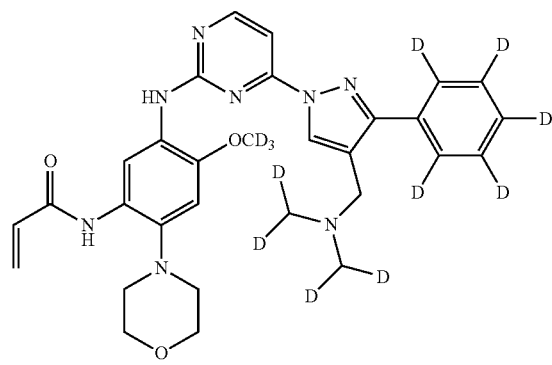

Formula (52)
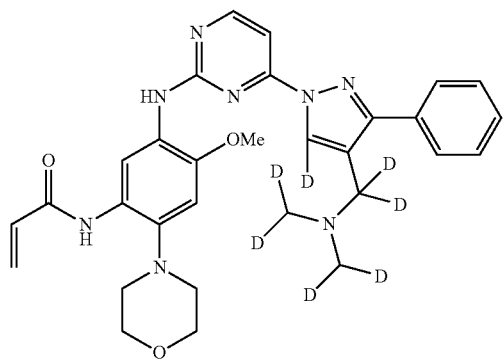
Formula (53)
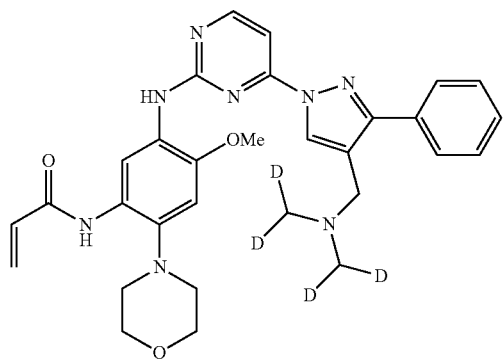
Formula (54)
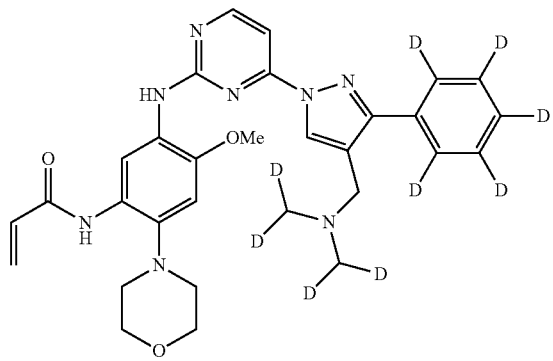
Formula (55)
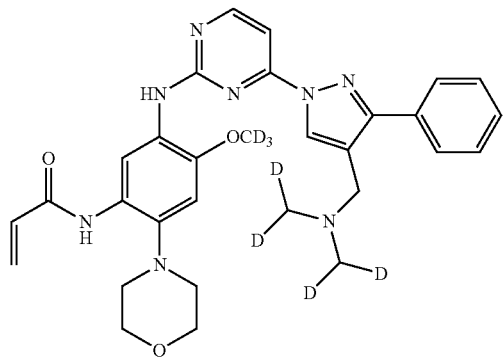
Formula (56)
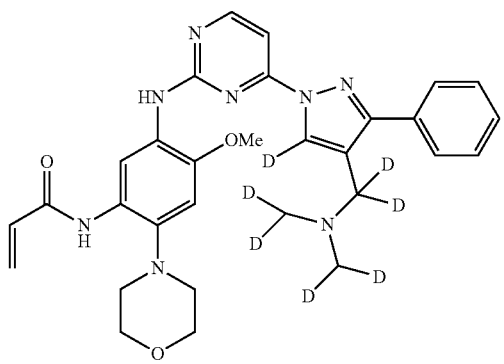
Formula (57)
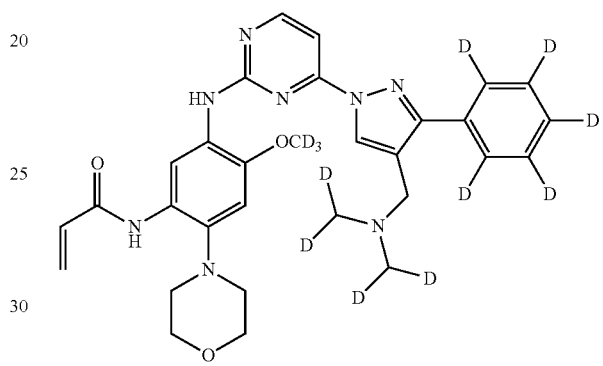
Formula (58)
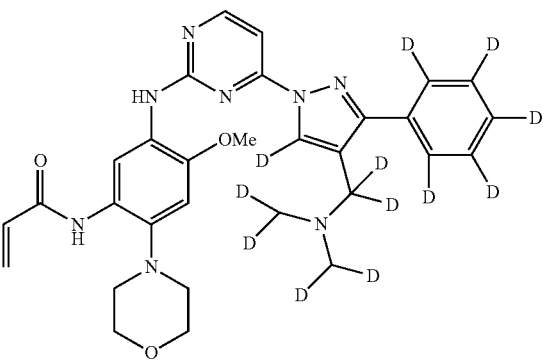
Formula (59)
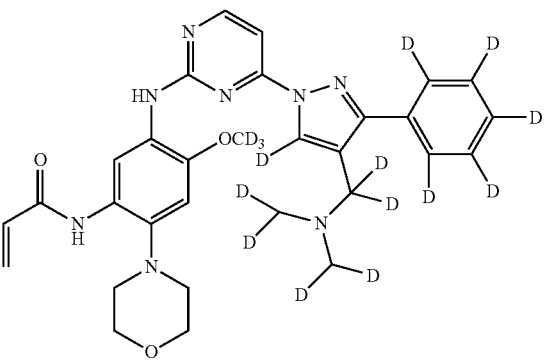

-continued

Formula (60)

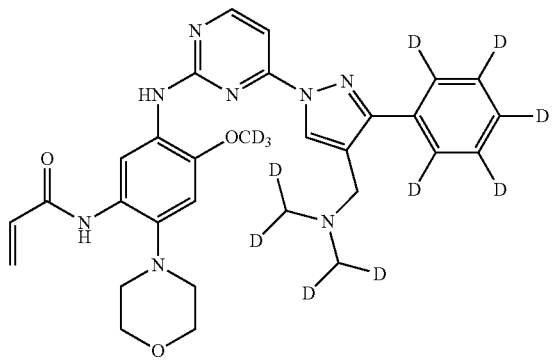

Formula (61)

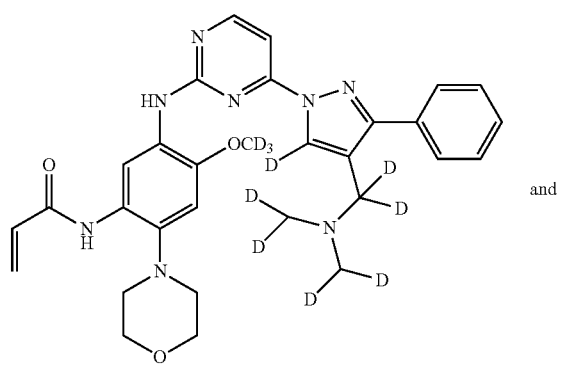

and

Formula (62)

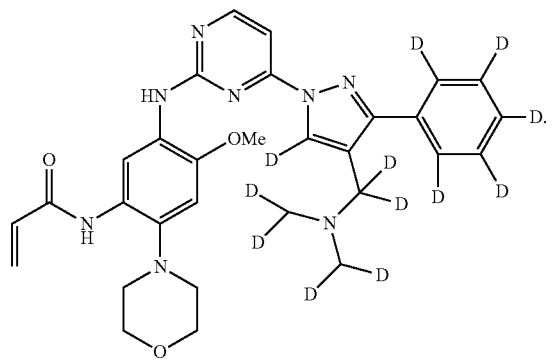

Formulations

The following formulation examples illustrate representative pharmaceutical compositions that may be prepared in accordance with this invention. The present disclosure, however, is not limited to the following pharmaceutical compositions.

Exemplary Formulation 1—Tablets: A compound of the present disclosure may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 2—Tablets: A compound of the present disclosure may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 3—Tablets: A compound of the present disclosure may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 4—Tablets: A compound of the present disclosure may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 5—Tablets: A compound of the present disclosure may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 6—Tablets: A compound of the present disclosure may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Exemplary Formulation 7—Tablets: A compound of the present disclosure may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 8—Capsules: A compound of the present disclosure may be admixed as a dry powder with a starch diluent in an approximate 1:1 weight ratio. The mixture is filled into 250 mg capsules (125 mg of active compound per capsule).

Exemplary Formulation 9—Liquid: A compound of the present disclosure (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 10—Injection: A compound of the present disclosure may be dissolved or suspended in a buffered sterile saline injectable aqueous medium to a concentration of approximately 5 mg/mL.

Administration

The pharmaceutical composition provided herein can be administered by a variety of routes including, but not limited to, oral administration, parenteral administration, inhalation administration, topical administration, rectal administration, nasal administration, buccal cavity administration, vaginal administration, administration by implant or other means of administration. For example, the parenteral administration as used herein includes subcutaneous administration, intradermal administration, intravenous administration, intramuscular administration, intra-articular administration, intra-arterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the condition disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to the administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In some embodiments, the chronic administration is intended to provide a constant level of the compound in the blood, e.g., within the therapeutic window over the extended period of time.

The pharmaceutical compositions disclosed herein may be further delivered using a variety of dosing methods. For example, in some embodiments, the pharmaceutical composition may be given as a bolus, e.g., in order to rapidly raise the concentration of the compound in the blood to an effective level. The placement of the bolus dose depends on the systemic levels of the active ingredient desired, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1% to about 50% by weight or preferably from about 1% to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 mg/kg to about 20 mg/kg of the compound disclosed herein, with preferred doses each providing from about 0.1 mg/kg to about 10 mg/kg, and especially about 1 mg/kg to about 5 mg/kg.

Transdermal doses are generally selected to provide similar or lower blood levels than are achieved using injection doses, generally in an amount ranging from about 0.01% to about 20% by weight, preferably from about 0.1% to about 20% by weight, preferably from about 0.1% to about 10% by weight, and more preferably from about 0.5% to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin or a flavoring agent such as peppermint, methyl salicylate, or orange flavoring.

Injectable compositions are typically based upon injectable sterile saline or phosphate-buffered saline or other injectable excipients known in the art. As mentioned before, the active compound in such compositions is typically a minor component, often being from about 0.05% to 10% by weight with the remainder being the injectable excipient and the like.

Transdermal compositions are typically formulated as a topical ointment or cream containing the active ingredient (s). When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the stable dermal penetration of the active ingredients or formulation. All such known transdermal formulations and ingredients are included within the scope provided herein.

The compounds disclosed herein can also be administered by a transdermal device. Accordingly, transdermal administration can be accomplished using a reservoir or a patch in porous membrane type or with various solid matrixes.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds disclosed herein can also be administered in sustained release forms or from sustained release drug delivery systems. A description of representative sustained release materials can be found in Remington's Pharmaceutical Sciences.

The present disclosure also relates to the pharmaceutically acceptable formulations of a compound disclosed herein. In one embodiment, the formulation comprises water. In another embodiment, the formulation comprises a cyclodextrin derivative. The most common cyclodextrins are α—, β— and γ-cyclodextrins consisting of 6, 7 and 8 α-1,4- linked glucose units, respectively, optionally comprising one or more substituents on the linked sugar moieties, which include, but are not limited to, methylated, hydroxyalkylated, acylated, and sulfoalkylether substitution. In some embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In some embodiments, the formulation comprises hexapropyl-β-cyclodextrin (e.g., 10% to 50% in water).

EXAMPLES

The preferred examples of the present disclosure are described in further detail below. It should be understood that these examples are only for illustrating the present disclosure and are not intended to limit the scope disclosed herein. Experimental methods that do not specify specific conditions in the examples are generally based on conventional conditions or conditions recommended by the manufacturer. Parts and percentages are parts by weight and percentages by weight unless otherwise indicated.

Generally, in the preparation process, the reactions are usually carried out in an inert solvent at the temperature ranging from room temperature to reflux temperature (e.g., from 0° C. to 100° C., preferably from 0° C. to 80° C.). The reaction time is usually from 0.1 to 60 hours, preferably from 0.5 to 24 hours.

Example 1

Preparation of N-(5-((4-(4-((dimethylamino)methyl-d$_2$)-3-phenyl-1H-pyrazol-1-yl-5-d)pyrimidin-2-yl)amino)-4-methoxy-2-morpholinophenyl)acrylamide (Compound T-1)

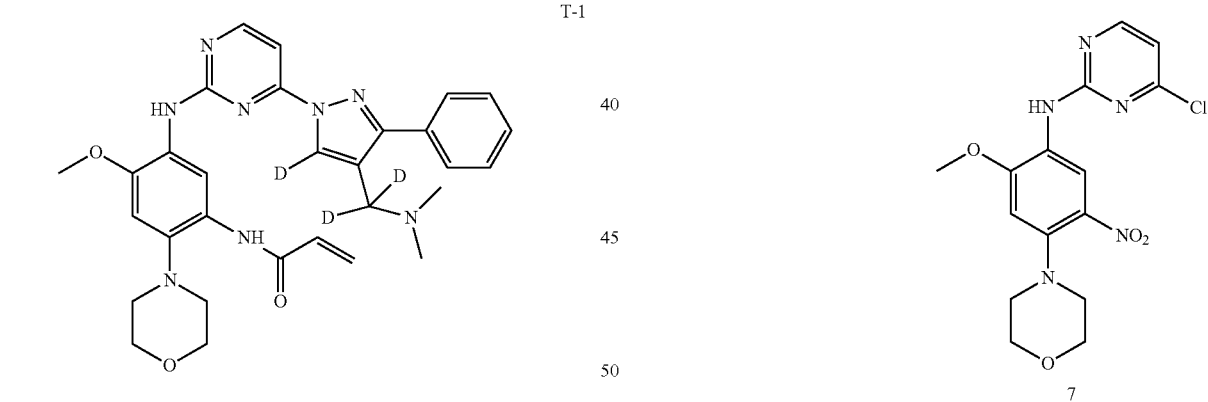

The specific synthetic steps are as follows:

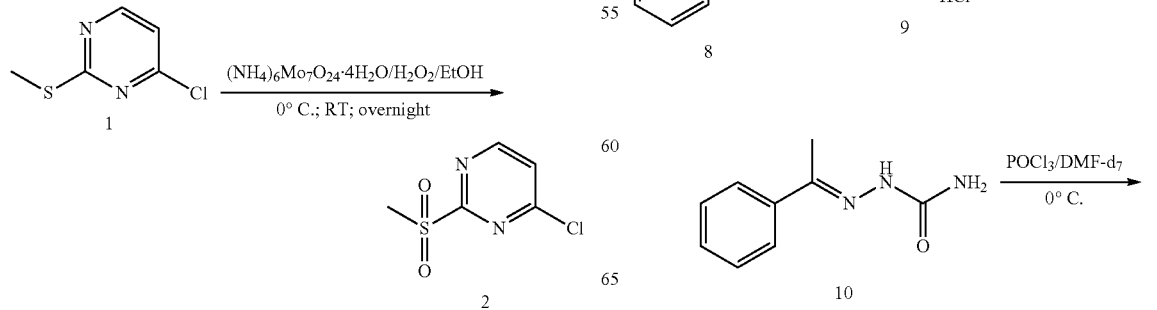

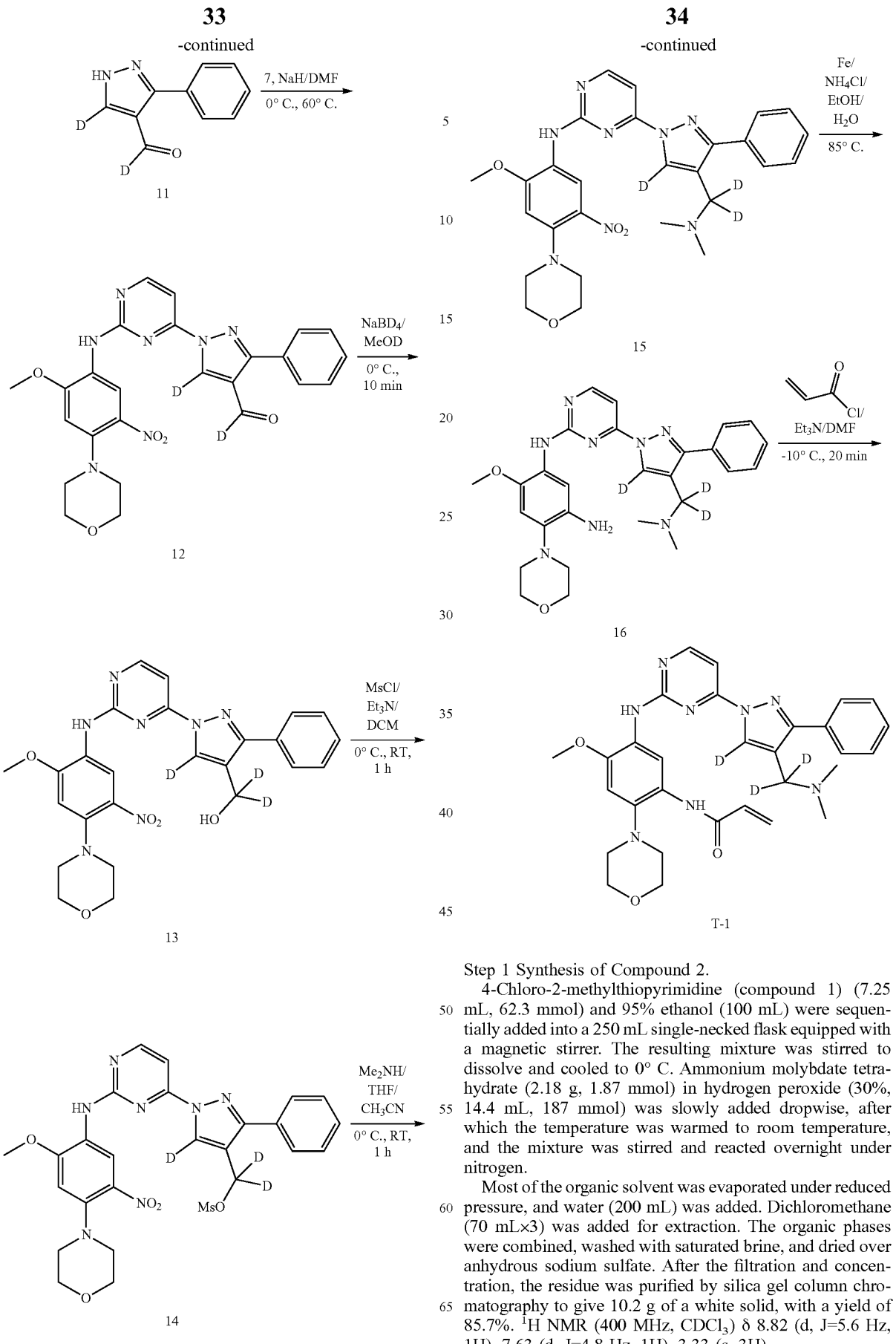

Step 1 Synthesis of Compound 2.

4-Chloro-2-methylthiopyrimidine (compound 1) (7.25 mL, 62.3 mmol) and 95% ethanol (100 mL) were sequentially added into a 250 mL single-necked flask equipped with a magnetic stirrer. The resulting mixture was stirred to dissolve and cooled to 0° C. Ammonium molybdate tetrahydrate (2.18 g, 1.87 mmol) in hydrogen peroxide (30%, 14.4 mL, 187 mmol) was slowly added dropwise, after which the temperature was warmed to room temperature, and the mixture was stirred and reacted overnight under nitrogen.

Most of the organic solvent was evaporated under reduced pressure, and water (200 mL) was added. Dichloromethane (70 mL×3) was added for extraction. The organic phases were combined, washed with saturated brine, and dried over anhydrous sodium sulfate. After the filtration and concentration, the residue was purified by silica gel column chromatography to give 10.2 g of a white solid, with a yield of 85.7%. $^1$H NMR (400 MHz, CDCl$_3$) δ 8.82 (d, J=5.6 Hz, 1H), 7.63 (d, J=4.8 Hz, 1H), 3.33 (s, 3H).

Step 2 Synthesis of Compound 4.

4-Fluoro-2-methoxy-5-nitroaniline (compound 3) (9.3 g, 50 mmol) and formic acid (50 mL) were sequentially added into a 100 mL single-necked flask equipped with a magnetic stirrer and a condenser. The mixture was heated to reflux, stirred and reacted for 2 hs at this temperature.

After cooling to room temperature, the unreacted formic acid was evaporated under reduced pressure. The residue was purified by silica gel column chromatography to give 7.8 g of a white solid, with a yield of 73%. LC-MS(APCI): m/z=215.1 (M+1)$^+$.

Step 3 Synthesis of Compound 6.

Compound 4 (2.14 g, 10 mmol), DMF (25 mL), $K_2CO_3$ (2.07 g, 15 mmol) and morpholine (0.87 g, 10 mmol) were sequentially added into a 100 mL single-necked flask equipped with a magnetic stirrer, and the mixture was stirred and reacted overnight at room temperature under nitrogen.

Ethyl acetate (80 mL) was added and the insoluble solid was filtered off. The filtrate was concentrated, and the residue was purified by silica gel column chromatography to give 2.11 g of a yellow solid, with a yield of 70%. LC-MS (APCI): m/z=282.1 (M+1)$^+$.

Step 4 Synthesis of Compound 7.

Compound 6 (2.81 g, 10 mmol) and dry DMF (15 ml) were sequentially added into a 100 mL three-necked flask equipped with a magnetic stirrer, cooled to 0° C., and NaH (60%, 480 mg, 12 mmol) was added.

The resulting mixture was stirred and reacted at room temperature under nitrogen for half an hour. Then the mixture was cooled to 0° C., and a dry solution of compound 2 (1.93 g, 10 mmol) in DMF (15 ml) was slowly added dropwise, after which, the mixture was stirred and reacted at room temperature for 3 h.

Water (25 mL) was added to quench the reaction. After stirring for 2 h, ethyl acetate (50 mL×3) was added for extraction. The organic phases were combined, and dried over anhydrous sodium sulfate. After the filtration and concentration, the residue was purified by silica gel column chromatography to give 2.83 g of a yellow solid, with a yield of 77%. LC-MS(APCI): m/z=366.1 (M+1)$^+$. $^1$H NMR (400 MHz, CDCl$_3$) δ9.19 (s, 1H), 8.36 (d, J=5.2 Hz, 1H), 7.70 (s, 1H), 6.82 (d, J=5.2 Hz, 1H), 6.61 (s, 1H), 4.00 (s, 3H), 3.89 (t, J=4.8 Hz, 4H), 3.08 (t, J=4.8 Hz, 4H).

Step 5 Synthesis of Compound 10.

Semicarbazide hydrochloride (compound 9, 2.04 g, 18.31 mmol) and anhydrous sodium acetate (2.05 g, 24.97 mmol) were added to the absolute ethanol (20 mL). The resulting mixture was refluxed for 45 minutes, and filtered when the mixture was still hot. Acetophenone (compound 8, 2.0 g, 16.65 mmol) was added to the filtrate, refluxed for 1 hour, and cooled to room temperature. A large amount of white solid was precipitated out. After the filtration, the residue was washed with a small amount of ethanol, and dried to give 2.5 g of a white solid, with a yield of 84.7%. LC-MS (APCI): m/z=178.1 (M+1)$^+$. $^1$H NMR (300 MHz, DMSO-d$_6$) δ 9.36 (s, 1H), 7.86-7.83 (m, 2H), 7.38-7.36 (m, 3H), 6.51 (s, 2H).

Step 6 Synthesis of Compound 11.

DMF-d$_7$ (5 mL) was added to a 50 mL three-necked flask equipped with a magnetic stirrer and a condenser. The flask was evacuated and purged with nitrogen. After cooling to 0° C., phosphorus oxychloride (4.98 g, 34.25 mmol) was slowly added dropwise, after which the mixture was warmed to room temperature and stirred for 20 minutes. The mixture was cooled to 0° C. again, and compound 10 (2.5 g, 14.11 mmol) was added. The reaction mixture was heated to 80° C., stirred and reacted for 1.5 h at this temperature. Then the mixture was poured into ice water (100 g) when it was still hot, and the pH was adjusted to 8 to 9 with an aqueous solution of NaOH (30%, w/w). The resulting mixture was stirred for half an hour, and the pH was adjusted to neutral with the concentrated hydrochloric acid. After stirring for 1 h, ethyl acetate (50 mL×3) was added for extraction. The organic phases were combined, washed with saturated brine, and dried over anhydrous sodium sulfate. After the filtration and concentration, the residue was purified by silica gel column chromatography to give 1.1 g of a white solid, with a yield of 44.8%. LC-MS(APCI): m/z=175.2 (M+1)$^+$. NMR (400 MHz, DMSO-d$_6$) δ 7.84-7.82 (m, 2H), 7.50-7.48 (m, 3H).

Step 7 Synthesis of Compound 12.

Compound 11 (100 mg, 571 μmol) and dry DMF (2 ml) were sequentially added into a 100 mL three-necked flask equipped with a magnetic stirrer, cooled to 0° C., and NaH (60%, 30 mg, 742 μmol) was added. The resulting mixture was stirred and reacted at room temperature under nitrogen for half an hour. Then the mixture was cooled to 0° C., and a dry solution of compound 7 (188 mg, 514 μmol) in DMF (3 ml) was slowly added dropwise. After the dropwise addition, the reaction solution was warmed to room temperature and heated to 60° C., at which the solution was stirred and reacted for 2 h.

Water (25 mL) was added to quench the reaction. After stirring for 2 h, ethyl acetate (50 mL×3) was added for extraction. The organic phases were combined, and dried over anhydrous sodium sulfate. After the filtration and concentration, the residue was purified by silica gel column chromatography to give 190 g of a yellow solid, with a yield of 66.1%. LC-MS(APCI): m/z=504.4 (M+1)$^+$. NMR (400 MHz, DMSO-d$_6$) δ 8.82 (s, 1H), 8.75 (s, 1H), 8.67 (d, J=3.9 Hz, 1H), 7.98-7.96 (m, 2H), 7.54-7.52 (m, 3H), 7.42 (d, J=3.9 Hz, 1H), 6.87 (s, 1H), 3.99 (s, 3H), 3.76 (t, J=3.3 Hz, 4H), 3.09 (t, J=3.3 Hz, 4H).

Step 8 Synthesis of Compound 13.

At 0° C., deuterated sodium borohydride (19 mg, 453 μmol) was added into a solution of compound 12 (190 mg, 377 μmol) in dichloromethane/methanol (10 mL, 1/1) under magnetic stirring, and the resulting mixture was stirred and reacted at 0° C. for 10 minutes.

Water (10 mL) was added to quench the reaction. After stirring for 10 minutes, the organic solvent was evaporated under reduced pressure, and a solid was precipitated out. The solid was filtered, washed with a small amount of water, and dried to give 190 mg of a white solid, with a yield of 99%. LC-MS(APCI): m/z=507.3 (M+1)$^+$.

Step 9 Synthesis of Compound 14.

At 0° C., triethylamine (114 mg, 1.13 mmol) was added to a solution of compound 13 (190 mg, 375 μmol) in dichloromethane (10 mL) under magnetic stirring, and methanesulfonyl chloride (129 mg, 1.13 mmol) was slowly added dropwise, after which, the resulting mixture was stirred and reacted at room temperature under nitrogen for 1 h.

The resulting reaction solution was used directly in the next reaction. LC-MS(APCI): m/z=585.2 (M+1)$^+$.

Step 10 Synthesis of Compound 15.

At 0° C., a solution of dimethylamine in tetrahydrofuran (5.6 mL, 2 M) was added dropwise into a solution of compound 14 in dichloromethane under magnetic stirring, after which, the resulting mixture was stirred and reacted overnight at room temperature under nitrogen.

The organic solvent was evaporated under reduced pressure, and the residue was purified by silica gel column chromatography to give 200 mg of a white solid, with a yield of 99%. LC-MS(APCI): m/z=535.5 (M+1)⁺. NMR (400 MHz, DMSO-d$_6$) δ8.91 (s, 1H), 8.60 (s, 1H), 8.57 (d, J=3.9 Hz, 1H), 7.98 (d, J=5.4 Hz, 2H), 7.51-7.43 (m, 3H), 7.35 (d, J=4.2 Hz, 1H), 6.87 (s, 1H), 4.00 (s, 3H), 3.75 (t, J=3.3 Hz, 4H), 3.08 (t, J=3.3 Hz, 4H), 2.23 (s, 6H).

Step 11 Synthesis of Compound 16.

A mixture of ethanol/water (15 mL, 2/1) and compound 15 (200 mg, 375 μmol) were added to a 50 mL single-necked flask equipped with a magnetic stirrer and a condenser. Reduced iron powder (209 mg, 3.75 mmol) and ammonium chloride (100 mg, 1.87 mmol) were added under stirring. The temperature was raised to 85° C. under nitrogen, at which the resulting mixture was stirred and reacted for 1 h.

The mixture was cooled to room temperature, and the insoluble solid was filtered off. The organic solvent was evaporated under reduced pressure, and the residue was extracted with ethyl acetate (15 mL×3). The organic phases were combined, dried over anhydrous sodium sulfate, filtered and concentrated to give 175 mg of a brown solid, with a yield of 92.7%. LC-MS(APCI): m/z=504.4 (M+1)⁺.

Step 12 Synthesis of Compound T-1.

Dry dichloromethane (10 mL) and compound 16 (175 mg, 347 μmol) were added into a 50 mL three-necked flask equipped with a magnetic stirrer. The resulting mixture was stirred to dissolve, cooled to −10° C., and triethylamine (105 mg, 1.04 mmol) was added. A solution of acryloyl chloride (47 mg, 521 μmol) in dichloromethane (1 mL) was slowly added dropwise under nitrogen, after which, the resulting mixture was stirred and reacted at −10° C. for 30 minutes.

Saturated Na$_2$CO$_3$ aqueous solution (5 mL) was added to quench the reaction, stirred for 10 minutes, and the organic phase was separated. The aqueous phase was extracted with dichloromethane (10 mL×2). The organic phases were combined, and dried over anhydrous sodium sulfate. After the filtration and concentration, the residue was purified by silica gel column chromatography to give 100 mg of a white solid, with a yield of 51.6%. LC-MS(APCI): m/z=558.5 (M+1)⁺. ¹H NMR (400 MHz, CDCl$_3$) δ 9.71 (s, 1H), 8.75 (s, 1H), 8.48 (d, J=3.9 Hz, 1H), 7.91 (s, 3H), 7.50-7.42 (m, 4H), 6.80 (s, 1H), 6.52 (d, J=12.6 Hz, 1H), 6.34 (dd, J1=12.6 Hz, J2=7.5 Hz, 1H), 5.87 (d, J=7.5 Hz, 1H), 3.93 (s, 3H), 3.90 (t, J=3.3 Hz, 4H), 2.90 (t, J=3.3 Hz, 4H), 2.36 (s, 6H).

Example 2

Preparation of N-(5-((4-(4-((dimethylamino)methyl)-3-(phenyl-d$_5$)-1H-pyrazol-1-yl)pyrimidin-2-yl)amino)-4-methoxy-2-morpholinophenyl)acrylamide (Compound T-2)

T-2

The Specific Synthetic Steps are as Follows:

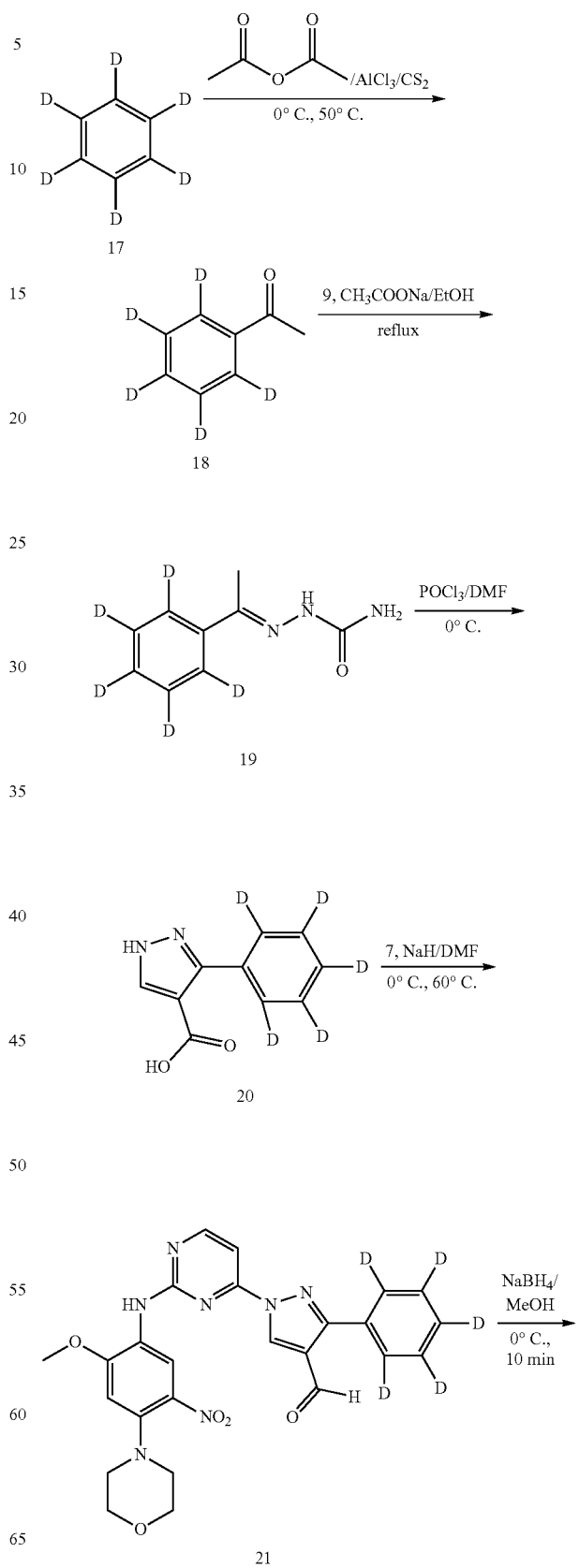

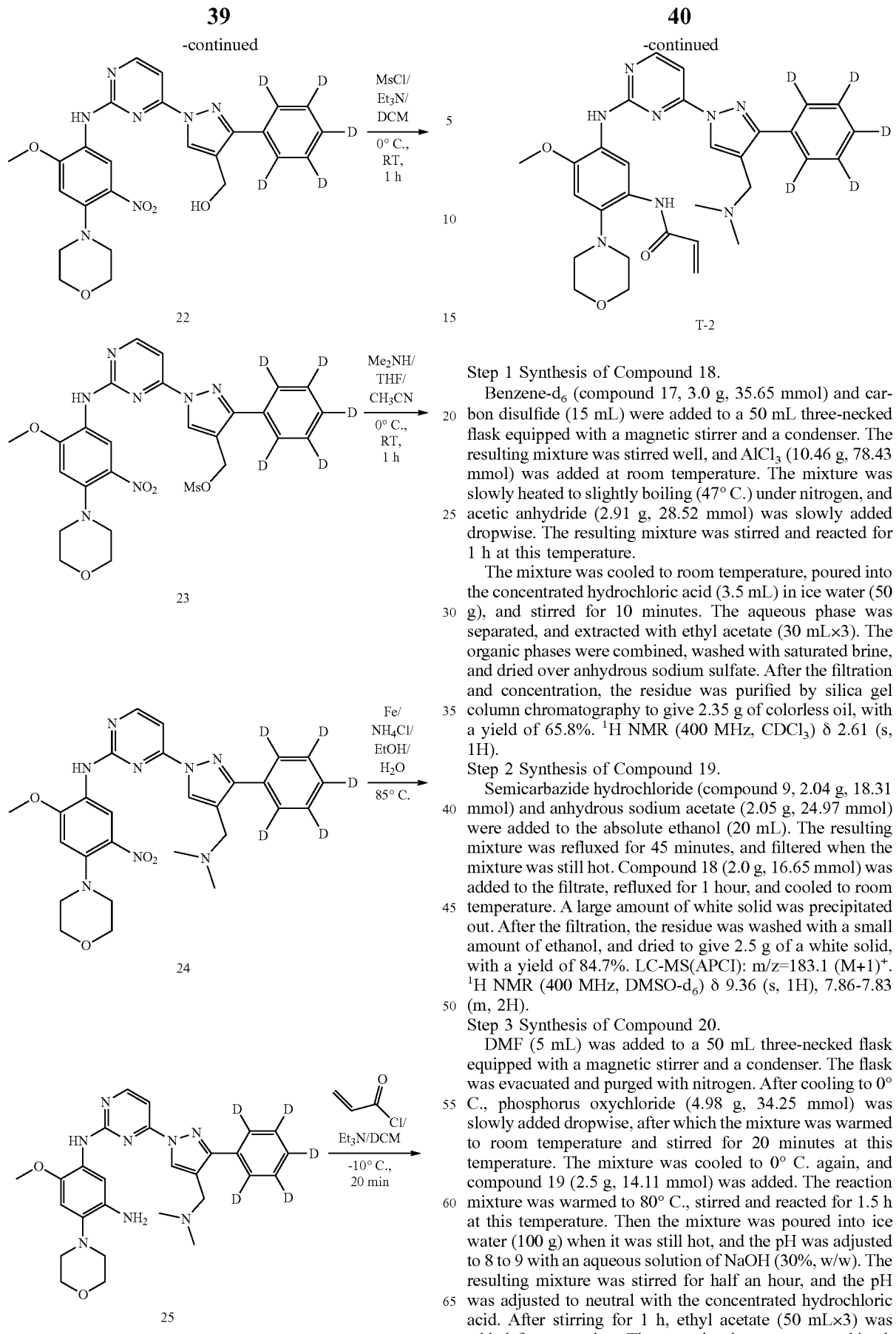

Step 1 Synthesis of Compound 18.

Benzene-d$_6$ (compound 17, 3.0 g, 35.65 mmol) and carbon disulfide (15 mL) were added to a 50 mL three-necked flask equipped with a magnetic stirrer and a condenser. The resulting mixture was stirred well, and AlCl$_3$ (10.46 g, 78.43 mmol) was added at room temperature. The mixture was slowly heated to slightly boiling (47° C.) under nitrogen, and acetic anhydride (2.91 g, 28.52 mmol) was slowly added dropwise. The resulting mixture was stirred and reacted for 1 h at this temperature.

The mixture was cooled to room temperature, poured into the concentrated hydrochloric acid (3.5 mL) in ice water (50 g), and stirred for 10 minutes. The aqueous phase was separated, and extracted with ethyl acetate (30 mL×3). The organic phases were combined, washed with saturated brine, and dried over anhydrous sodium sulfate. After the filtration and concentration, the residue was purified by silica gel column chromatography to give 2.35 g of colorless oil, with a yield of 65.8%. $^1$H NMR (400 MHz, CDCl$_3$) δ 2.61 (s, 1H).

Step 2 Synthesis of Compound 19.

Semicarbazide hydrochloride (compound 9, 2.04 g, 18.31 mmol) and anhydrous sodium acetate (2.05 g, 24.97 mmol) were added to the absolute ethanol (20 mL). The resulting mixture was refluxed for 45 minutes, and filtered when the mixture was still hot. Compound 18 (2.0 g, 16.65 mmol) was added to the filtrate, refluxed for 1 hour, and cooled to room temperature. A large amount of white solid was precipitated out. After the filtration, the residue was washed with a small amount of ethanol, and dried to give 2.5 g of a white solid, with a yield of 84.7%. LC-MS(APCI): m/z=183.1 (M+1)$^+$. $^1$H NMR (400 MHz, DMSO-d$_6$) δ 9.36 (s, 1H), 7.86-7.83 (m, 2H).

Step 3 Synthesis of Compound 20.

DMF (5 mL) was added to a 50 mL three-necked flask equipped with a magnetic stirrer and a condenser. The flask was evacuated and purged with nitrogen. After cooling to 0° C., phosphorus oxychloride (4.98 g, 34.25 mmol) was slowly added dropwise, after which the mixture was warmed to room temperature and stirred for 20 minutes at this temperature. The mixture was cooled to 0° C. again, and compound 19 (2.5 g, 14.11 mmol) was added. The reaction mixture was warmed to 80° C., stirred and reacted for 1.5 h at this temperature. Then the mixture was poured into ice water (100 g) when it was still hot, and the pH was adjusted to 8 to 9 with an aqueous solution of NaOH (30%, w/w). The resulting mixture was stirred for half an hour, and the pH was adjusted to neutral with the concentrated hydrochloric acid. After stirring for 1 h, ethyl acetate (50 mL×3) was added for extraction. The organic phases were combined, washed with saturated brine, and dried over anhydrous sodium sulfate. After the filtration and concentration, the residue was purified by silica gel column chromatography to give 1.1 g of a white solid, with a yield of 44.8%. LC-MS (APCI): m/z=178.2 (M+1)$^+$.

Step 4 Synthesis of Compound 21.

Compound 20 (100 mg, 571 μmol) and dry THF (2 ml) were sequentially added into a 100 mL three-necked flask equipped with a magnetic stirrer, cooled to 0° C., and NaH (60%, 30 mg, 742 μmol) was added. The resulting mixture was stirred and reacted at room temperature under nitrogen for half an hour. Then the mixture was cooled to 0° C., and a dry solution of compound 7 (188 mg, 514 μmol) in THF (3 ml) was slowly added dropwise. After the dropwise addition, the reaction solution was warmed to room temperature and heated to 60° C., at which the solution was stirred and reacted for 2 h.

Water (25 mL) was added to quench the reaction. After stirring for 2 h, ethyl acetate (50 mL×3) was added for extraction. The organic phases were combined, and dried over anhydrous sodium sulfate. After the filtration and concentration, the residue was purified by silica gel column chromatography to give 190 mg of a yellow solid, with a yield of 66.1%. LC-MS(APCI): m/z=507.2 (M+1)$^+$. $^1$H NMR (400 MHz, DMSO-d$_6$) δ10.05 (s, 1H), 9.29 (s, 1H), 8.84 (s, 1H), 8.75 (s, 1H), 8.67 (d, J=4.5 Hz, 1H), 7.42 (d, J=4.5 Hz, 1H), 6.87 (s, 1H), 4.00 (s, 3H), 3.76 (t, J=3.3 Hz, 4H), 3.09 (t, J=3.3 Hz, 4H).

Step 5 Synthesis of Compound 22.

At 0° C., sodium borohydride (19 mg, 453 μmol) was added into a solution of compound 21 (190 mg, 377 μmol) in dichloromethane/methanol (10 mL, 1/1) under magnetic stirring, and the resulting mixture was stirred and reacted at 0° C. for 10 minutes.

Water (10 mL) was added to quench the reaction. After stirring for 10 minutes, the organic solvent was evaporated under reduced pressure, and a solid was precipitated. The solid was filtered, washed with a small amount of water, and dried to give 190 mg of a white solid, with a yield of 99%. LC-MS(APCI): m/z=509.3 (M+1)$^+$.

Step 6 Synthesis of Compound 23.

At 0° C., triethylamine (114 mg, 1.13 mmol) was added to a solution of compound 22 (190 mg, 375 μmol) in dichloromethane (10 mL) under magnetic stirring, and methanesulfonyl chloride (129 mg, 1.13 mmol) was slowly added dropwise, after which, the resulting mixture was stirred and reacted at room temperature under nitrogen for 1 h.

The resulting reaction solution was used directly in the next reaction. LC-MS(APCI): m/z=587.2 (M+1))$^+$.

Step 7 Synthesis of Compound 24.

At 0° C., a solution of dimethylamine in tetrahydrofuran (5.6 mL, 2 M) was added dropwise into a solution of compound 23 in dichloromethane under magnetic stirring, after which, the resulting mixture was stirred and reacted overnight at room temperature under nitrogen. The organic solvent was evaporated under reduced pressure, and the residue was purified by silica gel column chromatography to give 200 mg of a white solid, with a yield of 99%. LC-MS (APCI): m/z=536.5 (M+1)$^+$. NMR (400 MHz, DMSO-d$_6$) δ 8.92 (s, 1H), 8.61-8.58 (m, 3H), 7.37 (d, J=3.9 Hz, 1H), 6.88 (s, 1H), 4.02 (s, 3H), 3.77 (t, J=3.3 Hz, 4H), 3.09 (t, J=3.3 Hz, 4H), 2.25 (s, 6H).

Step 8 Synthesis of Compound 25.

A mixture of ethanol/water (15 mL, 2/1) and compound 24 (200 mg, 375 μmol) were added to a 50 mL single-necked flask equipped with a magnetic stirrer and a condenser. Reduced iron powder (209 mg, 3.75 mmol) and ammonium chloride (100 mg, 1.87 mmol) were added under stirring. The temperature was raised to 85° C. under nitrogen, at which the resulting mixture was stirred and reacted for 1 h.

The mixture was cooled to room temperature, and the insoluble solid was filtered off. The organic solvent was evaporated under reduced pressure, and the residue was extracted with ethyl acetate (15 mL×3). The organic phases were combined, dried over anhydrous sodium sulfate, filtered and concentrated to give 175 mg of a brown solid, with a yield of 92.7%. LC-MS(APCI): m/z=506.4 (M+1)$^+$.

Step 9 Synthesis of Compound T-2.

Dry dichloromethane (10 mL) and compound 25 (175 mg, 347 μmol) were added into a 50 mL three-necked flask equipped with a magnetic stirrer, The resulting mixture was stirred to dissolve, cooled to −10° C., and triethylamine (105 mg, 1.04 mmol) was added. A solution of acryloyl chloride (47 mg, 521 μmol) in dichloromethane (1 mL) was slowly added dropwise under nitrogen, after which, the resulting mixture was stirred and reacted at −10° C. for 30 minutes.

Saturated Na$_2$CO$_3$ aqueous solution (5 mL) was added to quench the reaction, stirred for 10 minutes, and the organic phase was separated. The aqueous phase was extracted with dichloromethane (10 mL×2). The organic phases were combined, and dried over anhydrous sodium sulfate. After the filtration and concentration, the residue was purified by silica gel column chromatography to give 100 mg of a white solid, with a yield of 51.6%. LC-MS(APCI): m/z=560.5 (M+1)$^+$. $^1$H NMR (400 MHz, CDCl$_3$) δ 9.72 (s, 1H), 8.75 (s, 1H), 8.49 (d, J=3.9 Hz, 1H), 7.93 (s, 1H), 7.47 (d, J=4.2 Hz, 1H), 6.82 (s, 1H), 6.52 (d, J=12.6 Hz, 1H), 6.35 (dd, J1=12.9 Hz, J2=7.8 Hz, 1H), 5.88 (d, J=7.8 Hz, 1H), 3.94 (s, 3H), 3.91 (t, J=3.3 Hz, 4H), 2.91 (t, J=3.3 Hz, 4H), 2.38 (s, 6H).

Example 3

Preparation of N-(5-((4-(4-((dimethylamino)methyl)-3-phenyl-1H-pyrazol-1-yl)pyrimidin-2-yl)amino)-4-(methoxy-d$_3$)-2- morpholinophenyl)acrylamide (Compound T-3)

T-3

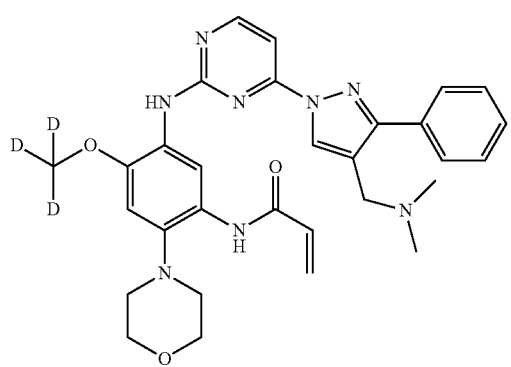

The specific synthetic steps are as follows:
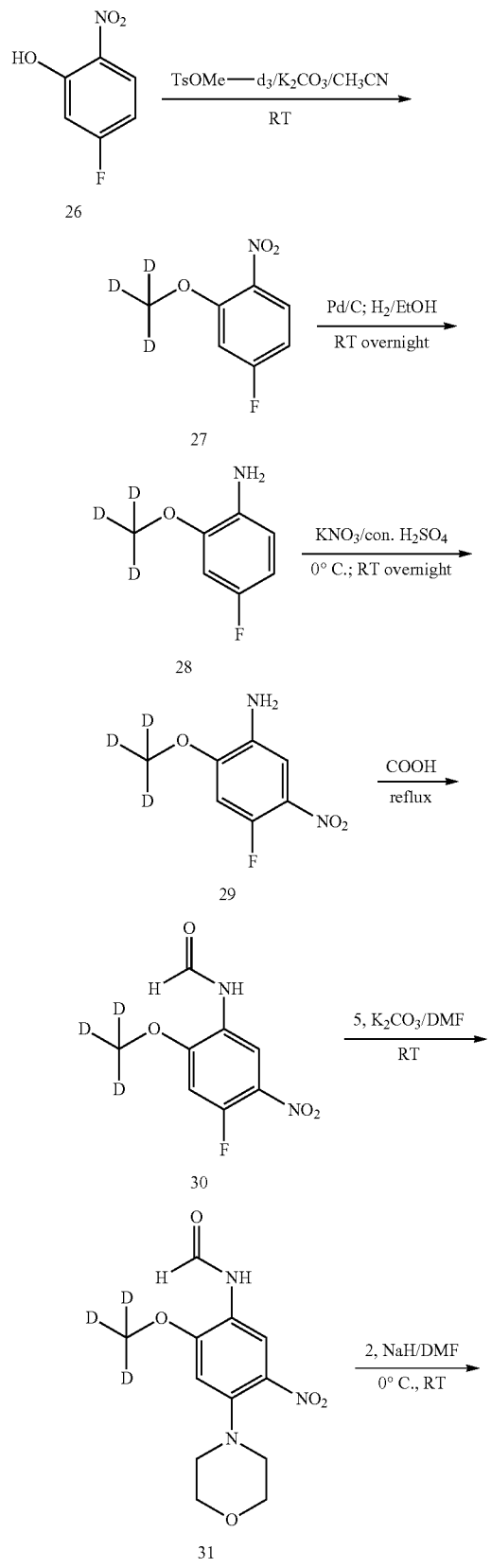
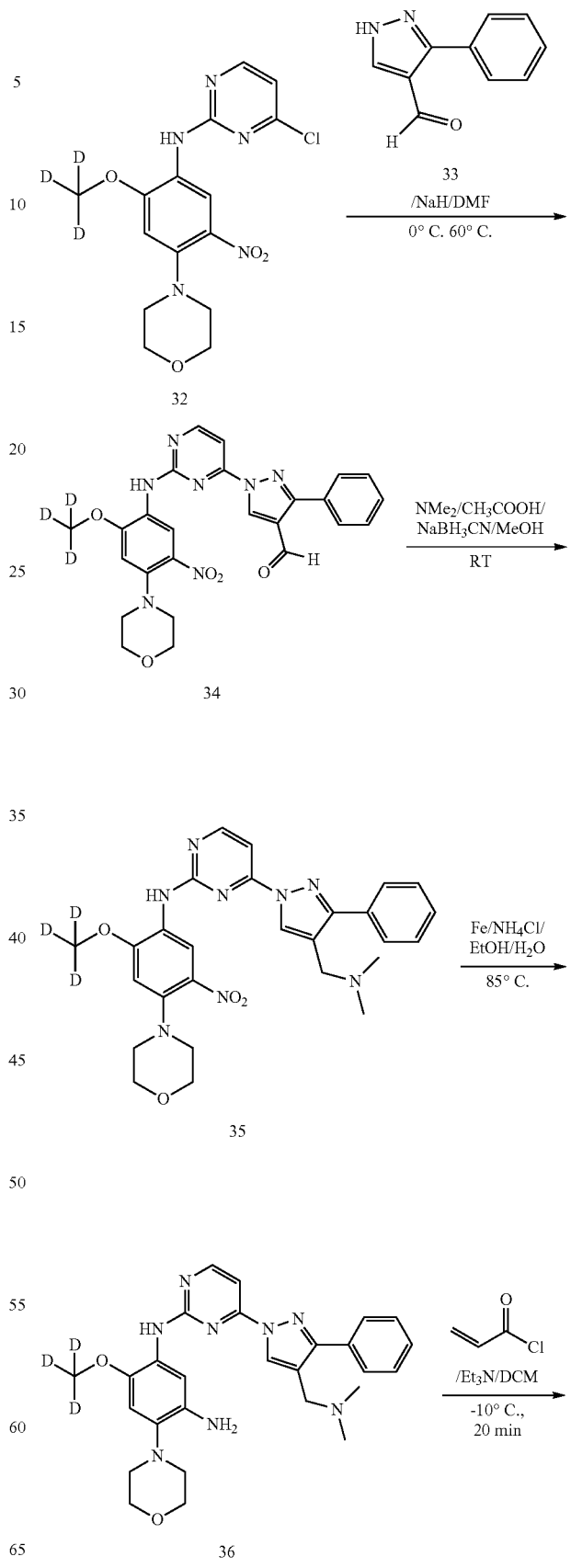

-continued

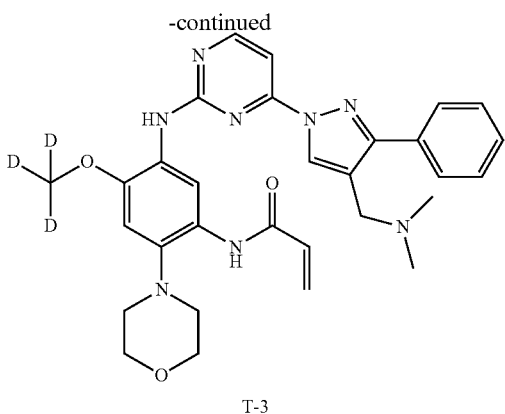

T-3

Step 1 Synthesis of Compound 27.

Acetonitrile (30 mL) and 2-hydroxy-4-fluoronitrobenzene (compound 26) (3.1 g, 20 mmol) were added into a 100 mL single-necked flask equipped with a magnetic stirrer, and stirred to dissolve completely. TsOMe-$d_3$ (4.0 g, 21.2 mmol) was added, and the resulting mixture was stirred overnight at room temperature under nitrogen. The insoluble solid was filtered off, and the filter cake was washed with ethyl acetate. The filtrate was concentrated, and purified by silica gel column chromatography to give 3.2 g of a white solid, with a yield of 92.0%. LC-MS(APCI): m/z=175.1 (M+1)$^+$.

Step 2 Synthesis of Compound 28.

Ethanol (30 mL) and compound 27 (3.2 g, 18.4 mmol) were added into a 100 mL single-necked flask equipped with a magnetic stirrer, and stirred to dissolve completely. Pd/C (320 mg, 10%) was added, and the resulting mixture was vacuumed and purged with hydrogen for three times, and stirred overnight at room temperature under hydrogen. The insoluble Pd/C was filtered off, and the filter cake was washed with ethyl acetate, and the filtrate was concentrated to give 2.5 g of a white solid, with a yield of 94.3%. LC-MS (APCI): m/z=145.1 (M+1)$^+$.

Step 3 Synthesis of Compound 29.

In an ice water bath, concentrated sulfuric acid (30 mL) and compound 28 (2.16 g, 15 mmol) were added to a 100 mL single-necked flask equipped with a magnetic stirrer, and stirred to dissolve completely. Potassium nitrate (1.66 g, 16.5 mmol) was added in batches, after which, the resulting mixture was slowly warmed to room temperature and stirred overnight at this temperature. The resulting mixture was poured into the ice water (150 g), and the pH was adjusted to 9 with ammonia. Ethyl acetate (50 mL×3) was added for extraction. The organic phases were combined, wash with saturated saline, and dried over anhydrous sodium sulfate. After the filtration and concentration, the residue was purified by silica gel column chromatography to give 1.25 g of a yellow solid, with a yield of 44.1%. LC-MS(APCI): m/z=190.1 (M+1)$^+$.

Step 4 Synthesis of Compound 30.

Compound 29 (1.25 g, 6.61 mmol) and formic acid (10 mL) were sequentially added into a 100 mL single-necked flask equipped with a magnetic stirrer and a condenser. The mixture was heated to reflux, stirred and reacted for 2 hs at this temperature. After cooling to room temperature, the unreacted formic acid was evaporated under reduced pressure. The residue was purified by silica gel column chromatography to give 1.1 g of a white solid, with a yield of 83.1%. LC-MS(APCI): m/z=218.1 (M+1)$^+$.

Step 5 Synthesis of Compound 31.

Compound 30 (1.1 g, 5.07 mmol), DMF (8 mL), K$_2$CO$_3$ (1.1 g, 8 mmol) and morpholine (0.52 g, 6 mmol) were sequentially added into a 100 mL single-necked flask equipped with a magnetic stirrer, and the mixture was stirred and reacted overnight at room temperature under nitrogen. Ethyl acetate (80 mL) was added and the insoluble solid was filtered off. The filtrate was concentrated, and the residue was purified by silica gel column chromatography to give 1.0 g of a yellow solid, with a yield of 69.6%. LC-MS (APCI): m/z=285.1 (M+1)$^+$.

Step 6 Synthesis of Compound 32.

Compound 31 (1.0 g, 3.52 mmol) and dry DMF (8 ml) were sequentially added into a 100 mL three-necked flask equipped with a magnetic stirrer, cooled to 0° C., and NaH (60%, 200 mg, 5 mmol was added. The resulting mixture was stirred and reacted at room temperature under nitrogen for half an hour. Then the mixture was cooled to 0° C., and a dry solution of compound 2 (0.77 g, 4 mmol) in DMF (2 ml) was slowly added dropwise, after which, the mixture was stirred and reacted at room temperature for 3 h. Water (25 mL) was added to quench the reaction. After stirring for 2 h, ethyl acetate (40 mL×3) was added for extraction. The organic phases were combined, and dried over anhydrous sodium sulfate. After the filtration and concentration, the residue was purified by silica gel column chromatography to give 0.92 g of a yellow solid, with a yield of 71.4%. LC-MS(APCI): m/z=369.1 (M+1)$^+$. $^1$H NMR (400 MHz, CDCl$_3$) 9.19 (s, 1H), 8.36 (d, J=5.2 Hz, 1H), 7.70 (s, 1H), 6.82 (d, J=5.2 Hz, 1H), 6.61 (s, 1H), 3.89 (t, J=4.8 Hz, 4H), 3.08 (t, J=4.8 Hz, 4H).

Step 7 Synthesis of Compound 34.

Compound 33 (100 mg, 571 µmol) and dry DMF (2 ml) were sequentially added into a 100 mL three-necked flask equipped with a magnetic stirrer, cooled to 0° C., and NaH (60%, 30 mg, 742 µmol) was added. The resulting mixture was stirred and reacted at room temperature under nitrogen for half an hour. Then the mixture was cooled to 0° C., and a solution of compound 32 (188 mg, 514 µmol) in dry DMF (3 ml) was slowly added dropwise. After the dropwise addition, the reaction solution was warmed to room temperature and heated to 60° C., at which the solution was stirred and reacted for 2 h.

Water (25 mL) was added to quench the reaction. After stirring for 2 h, ethyl acetate (50 mL×3) was added for extraction. The organic phases were combined, and dried over anhydrous sodium sulfate. After the filtration and concentration, the residue was purified by silica gel column chromatography to give 190 mg of a yellow solid, with a yield of 66.1%. LC-MS(APCI): m/z=505.3 (M+1)$^+$. $^1$H NMR (400 MHz, DMSO-d$_6$) δ10.05 (s, 1H), 9.29 (s, 1H), 8.82 (s, 1H), 8.75 (s, 1H), 8.67 (d, J=3.9 Hz, 1H), 7.98-7.96 (m, 2H), 7.54-7.52 (m, 3H), 7.42 (d, J=3.9 Hz, 1H), 6.87 (s, 1H), 3.76 (t, J=3.3 Hz, 4H), 3.09 (t, J=3.3 Hz, 4H).

Step 8 Synthesis of Compound 35.

Compound 34 (190 mg, 0.377 mmol) and methanol (6 mL) were sequentially added into a 50 mL three-necked flask equipped with a magnetic stirrer, and stirred to dissolve. Dimethylamine methanol solution (2 M, 0.75 mmol, 0.38 mL) and glacial acetic acid (2 drops) were added and stirred at room temperature for 30 minutes. Sodium cyanoborohydride (0.75 mmol, 46 mg) was added, and stirred overnight at room temperature under nitrogen. The reaction solution was concentrated and purified by silica gel column chromatography to give 150 mg of a white solid, with a yield of 74.6%. LC-MS(APCI): m/z=534.2 (M+1)$^+$. $^1$H NMR (400 MHz, DMSO-d$_6$) δ8.91 (s, 1H), 8.60 (s, 1H), 8.57 (d, J=3.9 Hz, 1H), 7.98 (d, J=5.4 Hz, 2H), 7.69 (s, 1H), 7.51-7.43 (m, 3H), 7.35 (d, J=4.2 Hz, 1H), 6.87 (s, 1H), 3.75 (t, J=3.3 Hz, 4H), 3.50 (s, 2H), 3.08 (t, J=3.3 Hz, 4H), 2.23 (s, 6H).

Step 9 Synthesis of Compound 36.

A mixture of ethanol/water (10 mL, 2/1) and compound 35 (150 mg, 280 μmol) were added to a 50 mL single-necked flask equipped with a magnetic stirrer and a condenser. Reduced iron powder (209 mg, 3.75 mmol) and ammonium chloride (100 mg, 1.87 mmol) were added under stirring. The temperature was raised to 85° C. under nitrogen, at which the resulting mixture was stirred and reacted for 1 h. The mixture was cooled to room temperature, and the insoluble solid was filtered off. The organic solvent was evaporated under reduced pressure, and the residue was extracted with ethyl acetate (15 mL×3). The organic phases were combined, dried over anhydrous sodium sulfate, filtered and concentrated to give 120 mg of a brown solid, with a yield of 85.2%. LC-MS(APCI): m/z=504.2 (M+1)$^+$.

Step 10 Synthesis of Compound T-3.

Dry dichloromethane (10 mL) and compound 36 (120 mg, 241 μmol) were added into a 50 mL three-necked flask equipped with a magnetic stirrer. The resulting mixture was stirred to dissolve, cooled to −10° C., and triethylamine (105 mg, 1.04 mmol) was added. A solution of acryloyl chloride (23 mg, 260 μmol) in dichloromethane (1 mL) was slowly added dropwise under nitrogen, after which the resulting mixture was stirred and reacted at −10° C. for 30 minutes.

Saturated Na$_2$CO$_3$ aqueous solution (5 mL) was added to quench the reaction, stirred for 10 minutes, and the organic phase was separated. The aqueous phase was extracted with dichloromethane (10 mL×2). The organic phases were combined, and dried over anhydrous sodium sulfate. After the filtration and concentration, the residue was purified by silica gel column chromatography to give 60 mg of a white solid, with a yield of 44.9%. LC-MS(APCI): m/z=558.2 (M+1)$^+$. $^1$H NMR (400 MHz, CDCl$_3$) δ 9.72 (s, 1H), 9.54 (br s, 1H), 8.75 (s, 1H), 8.49 (d, J=3.9 Hz, 1H), 7.97-7.92 (m, 3H), 7.51-7.41 (m, 4H), 6.82 (s, 1H), 6.52 (d, J=12.6 Hz, 1H), 6.38-6.32 (m, 1H), 5.88 (d, J=7.8 Hz, 1H), 3.91 (t, J=3.3 Hz, 4H), 2.91 (t, J=3.3 Hz, 4H), 2.38 (s, 6H).

Example 4

Preparation of N-(5-((4-(4-((bis(methyl-d$_3$)amino)methyl)-3-phenyl-1H-pyrazol-1-yl)pyrimidin-2-yl)amino)-4-methoxy-2-morpholinophenyl)acrylamide (Compound T-4)

The specific synthetic steps are as follows:

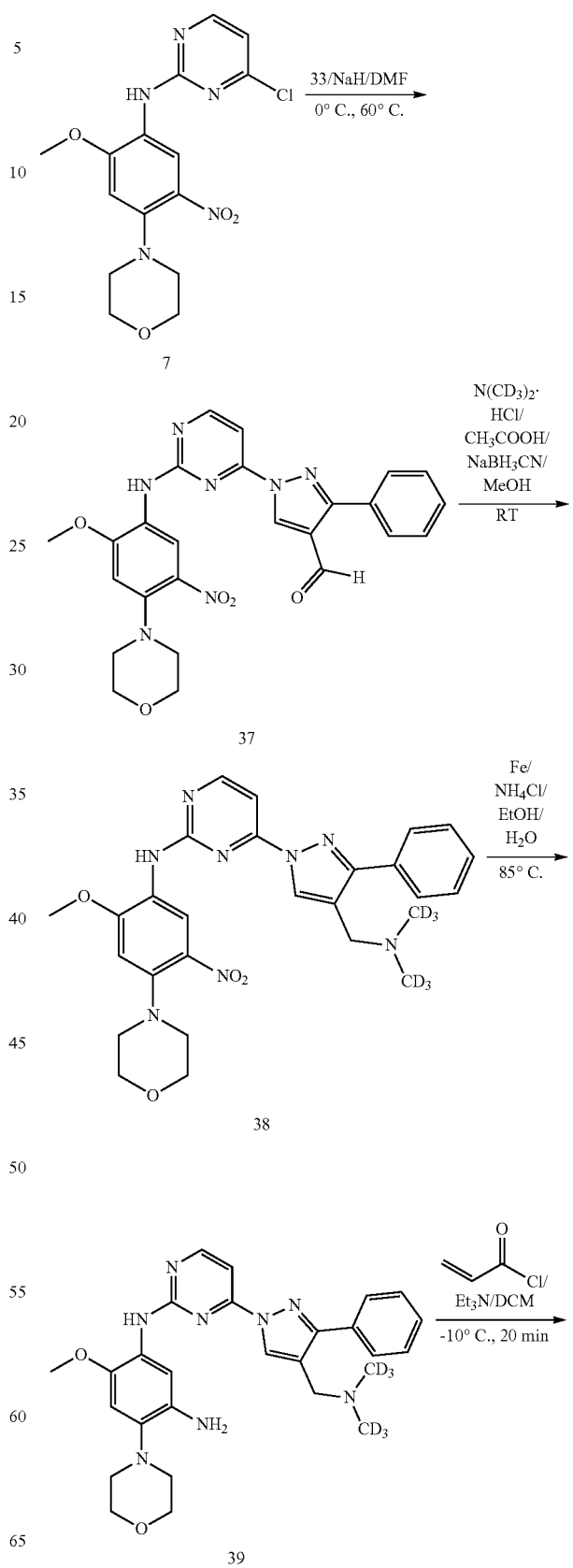

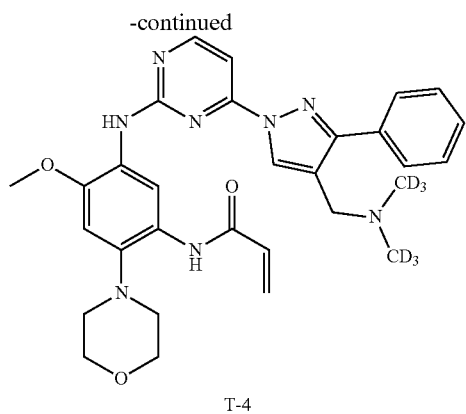

T-4

Step 1 Synthesis of Compound 37.

Compound 33 (100 mg, 571 μmol) and dry DMF (2 ml) were sequentially added into a 100 mL three-necked flask equipped with a magnetic stirrer, cooled to 0° C., and NaH (60%, 30 mg, 742 μmol) was added. The resulting mixture was stirred and reacted at room temperature under nitrogen for half an hour. Then the mixture was cooled to 0° C., and a dry solution of compound 7 (188 mg, 514 μmol) in DMF (3 ml) was slowly added dropwise. After the dropwise addition, the reaction solution was warmed to room temperature and heated to 60° C., at which the solution was stirred and reacted for 2 h. Water (25 mL) was added to quench the reaction. After stirring for 2 h, ethyl acetate (50 mL×3) was added for extraction. The organic phases were combined, and dried over anhydrous sodium sulfate. After the filtration and concentration, the residue was purified by silica gel column chromatography to give 190 mg of a yellow solid, with a yield of 66.1%. LC-MS(APCI): m/z=502.2 (M+1)$^+$. $^1$H NMR (400 MHz, DMSO-$d_6$) δ10.05 (s, 1H), 9.29 (s, 1H), 8.82 (s, 1H), 8.75 (s, 1H), 8.67 (d, J=3.9 Hz, 1H), 7.98-7.96 (m, 2H), 7.54-7.52 (m, 3H), 7.42 (d, J=3.9 Hz, 1H), 6.87 (s, 1H), 3.99 (s, 3H), 3.76 (t, J=3.3 Hz, 4H), 3.09 (t, J=3.3 Hz, 4H).

Step 2 Synthesis of Compound 38.

Dimethylamine-$d_6$ hydrochloride (0.75 mmol, 65 mg) and methanol (5 mL) were sequentially added into a 50 mL three-necked flask equipped with a magnetic stirrer, and stirred to dissolve. Granular NaOH (0.75 mmol, 30 mg) was added and stirred at room temperature for 30 minutes. Then, compound 37 (190 mg, 0.377 mmol) and glacial acetic acid (2 drops) were added, stirred and reacted at room temperature for 30 minutes. Sodium cyanoborohydride (0.75 mmol, 46 mg) was added afterwards, and stirred overnight at room temperature under nitrogen. The reaction solution was concentrated and purified by silica gel column chromatography to give 150 mg of a white solid, with a yield of 74.6%. LC-MS(APCI): m/z=537.2 (M+1)$^+$. $^1$H NMR (400 MHz, DMSO-$d_6$) δ 8.91 (s, 1H), 8.60 (s, 1H), 8.57 (d, J=3.9 Hz, 1H), 7.98 (d, J=5.4 Hz, 2H), 7.69 (s, 1H), 7.51-7.43 (m, 3H), 7.35 (d, J=4.2 Hz, 1H), 6.87 (s, 1H), 4.00 (s, 3H), 3.75 (t, J=3.3 Hz, 4H), 3.50 (s, 2H), 3.08 (t, J=3.3 Hz, 4H).

Step 3 Synthesis of Compound 39.

A mixture of ethanol/water (10 mL, 2/1) and compound 38 (150 mg, 280 μmol) were added to a 50 mL single-necked flask equipped with a magnetic stirrer and a condenser. Reduced iron powder (209 mg, 3.75 mmol) and ammonium chloride (100 mg, 1.87 mmol) were added under stirring. The temperature was raised to 85° C. under nitrogen, at which the resulting mixture was stirred and reacted for 1 h. The mixture was cooled to room temperature, and the insoluble solid was filtered off. The organic solvent was evaporated under reduced pressure, and the residue was extracted with ethyl acetate (15 mL×3). The organic phases were combined, dried over anhydrous sodium sulfate, filtered and concentrated to give 120 mg of a brown solid, with a yield of 85.2%. LC-MS(APCI): m/z=507.2 (M+1)$^+$.

Step 4 Synthesis of Compound T-4.

Dry dichloromethane (10 mL) and compound 39 (120 mg, 241 μmol) were added into a 50 mL three-necked flask equipped with a magnetic stirrer. The resulting mixture was stirred to dissolve, cooled to −10° C., and triethylamine (105 mg, 1.04 mmol) was added. A solution of acryloyl chloride (23 mg, 260 μmol) in dichloromethane (1 mL) was slowly added dropwise under nitrogen, after which, the resulting mixture was stirred and reacted at −10° C. for 30 minutes. Saturated Na$_2$CO$_3$ aqueous solution (5 mL) was added to quench the reaction, stirred for 10 minutes, and the organic phase was separated. The aqueous phase was extracted with dichloromethane (10 mL×2). The organic phases were combined, and dried over anhydrous sodium sulfate. After the filtration and concentration, the residue was purified by silica gel column chromatography to give 60 mg of a white solid, with a yield of 44.9%. LC-MS(APCI): m/z=561.2 (M+1)$^+$. $^1$H NMR (300 MHz, CDCl$_2$) δ 9.72 (s, 1H), 9.54 (br s, 1H), 8.75 (s, 1H), 8.49 (d, J=3.9 Hz, 1H), 7.97-7.92 (m, 3H), 7.51-7.41 (m, 4H), 6.82 (s, 1H), 6.52 (d, J=12.6 Hz, 1H), 6.38-6.32 (m, 1H), 5.88 (d, J=7.8 Hz, 1H), 4.01 (s, 3H), 3.91 (t, J=3.3 Hz, 4H), 2.91 (t, J=3.3 Hz, 4H).

Example 5

Preparation of N-(5-((4-(4-((bis(methyl-$d_2$)amino) methyl)-3-phenyl-1H-pyrazol-1-yl)pyrimidin-2-yl) amino)-4-methoxy-2-morpholinophenyl)acrylamide (Compound T-5)

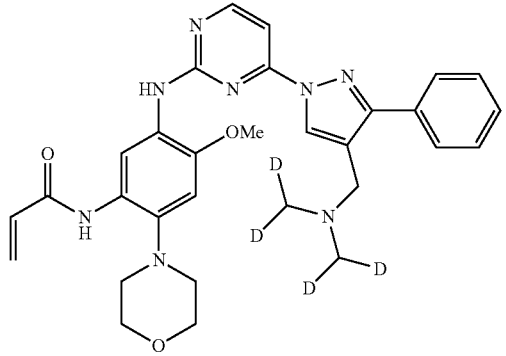

T-5

The following routes are used for synthesis:

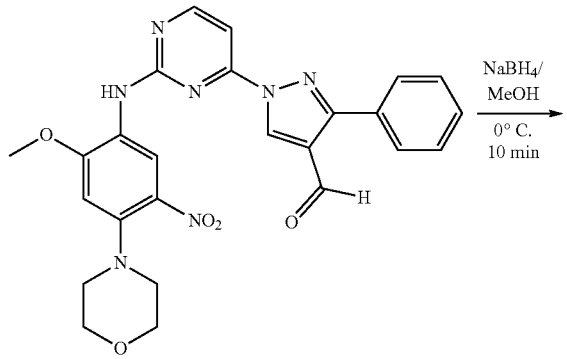

37

-continued

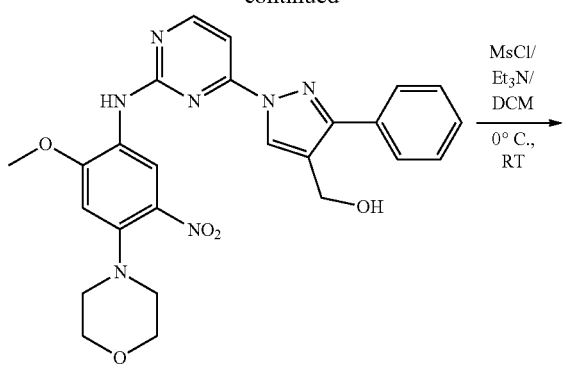

40

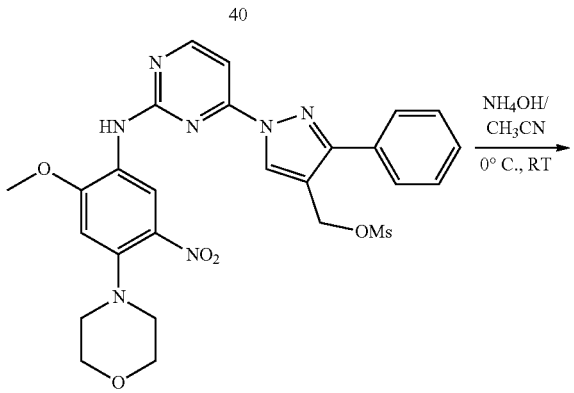

41

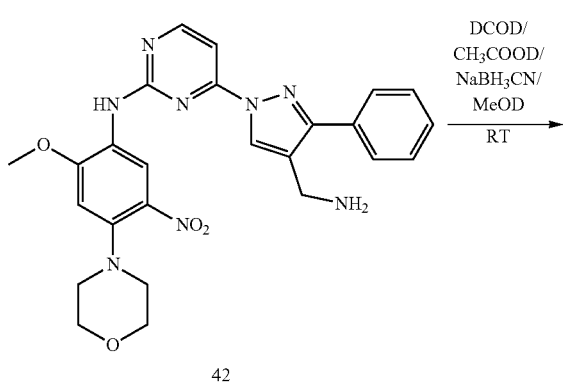

42

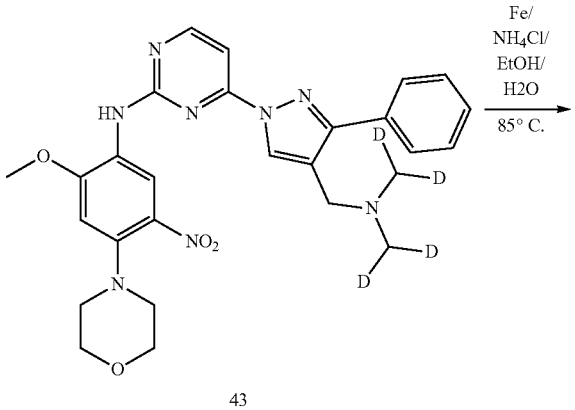

43

-continued

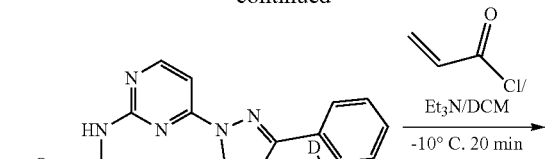

44

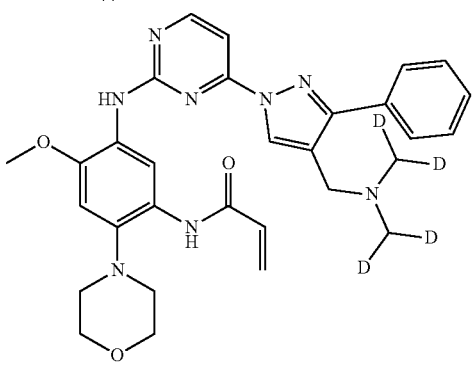

T-5

Step 1 Synthesis of Compound 40.

At 0° C., sodium borohydride (19 mg, 453 µmol) was added into a solution of compound 37 (190 mg, 377 µmol) in dichloromethane/methanol (10 mL, 1/1) under magnetic stirring, and the resulting mixture was stirred and reacted at 0° C. for 10 minutes. Water (10 mL) was added to quench the reaction. After stirring for 10 minutes, the organic solvent was evaporated under reduced pressure, and a solid was precipitated out. The solid was filtered, washed with a small amount of water, and dried to give 190 mg of a white solid, with a yield of 99%. LC-MS(APCI): m/z=504.2 (M+1)$^+$.

Step 2 Synthesis of Compound 41.

At 0° C., triethylamine (114 mg, 1.13 mmol) was added to a solution of compound 40 (190 mg, 375 µmol) in dichloromethane (10 mL) under magnetic stirring, and methanesulfonyl chloride (129 mg, 1.13 mmol) was slowly added dropwise, after which, the resulting mixture was stirred and reacted at room temperature under nitrogen for 1 h. The resulting reaction solution was used directly in the next reaction. LC-MS(APCI): m/z=582.2 (M+1)$^+$.

Step 3 Synthesis of Compound 42.

At 0° C., acetonitrile (5 mL) was added to a solution of compound 41 in dichloromethane under magnetic stirring. Ammonia (3 mL) was added dropwise, after which, the resulting mixture was stirred and reacted overnight at room temperature under nitrogen. The organic solvent was evaporated under reduced pressure, and the residue was purified by silica gel column chromatography to give 200 mg of a white solid, with a yield of 99%. LC-MS(APCI): m/z=503.2 (M+1)$^+$.

Step 4 Synthesis of Compound 43.

Compound 42 (200 mg, 0.4 mmol) and methanol-d (5 mL) were sequentially added into a 50 mL three-necked flask equipped with a magnetic stirrer, and stirred to dissolve. Acetic acid-d (1 drop) and a solution of deuterated formaldehyde in D₂O (20% w/w, 1.0 mmol, 0.16 g) were added dropwise, and the resulting mixture was stirred and reacted at room temperature for 30 minutes. Then sodium cyanoborohydride (0.75 mmol, 46 mg) was added, followed by stirring at room temperature overnight under nitrogen. The reaction solution was concentrated and purified by silica gel column chromatography to give 150 mg of a white solid, with a yield of 74.6%. LC-MS(APCI): m/z=535.2 (M+1)⁺. NMR (400 MHz, DMSO-d₆) δ 8.91 (s, 1H), 8.60 (s, 1H), 8.57 (d, J=3.9 Hz, 1H), 7.98 (d, J=5.4 Hz, 2H), 7.69 (s, 1H), 7.51-7.43 (m, 3H), 7.35 (d, J=4.2 Hz, 1H), 6.87 (s, 1H), 4.00 (s, 3H), 3.75 (t, J=3.3 Hz, 4H), 3.50 (s, 2H), 3.08 (t, J=3.3 Hz, 4H), 2.23 (s, 2H).

Step 5 Synthesis of Compound 44.

A mixture of ethanol/water (10 mL, 2/1) and compound 43 (150 mg, 280 μmol) were added to a 50 mL single-necked flask equipped with a magnetic stirrer and a condenser. Reduced iron powder (209 mg, 3.75 mmol) and ammonium chloride (100 mg, 1.87 mmol) were added under stirring. The temperature was raised to 85° C. under nitrogen, at which the resulting mixture was stirred and reacted for 1 h. The mixture was cooled to room temperature, and the insoluble solid was filtered off. The organic solvent was evaporated under reduced pressure, and the residue was extracted with ethyl acetate (15 mL×3). The organic phases were combined, dried over anhydrous sodium sulfate, filtered and concentrated to give 120 mg of a brown solid, with a yield of 85.2%. LC-MS(APCI): m/z=505.2 (M+1)⁺.

Step 6 Synthesis of Compound T-5.

Dry dichloromethane (10 mL) and compound 44 (120 mg, 241 μmol) were added into a 50 mL three-necked flask equipped with a magnetic stirrer. The resulting mixture was stirred to dissolve, cooled to −10° C., and triethylamine (105 mg, 1.04 mmol) was added. A solution of acryloyl chloride (23 mg, 260 μmol) in dichloromethane (1 mL) was slowly added dropwise under nitrogen, after which, the resulting mixture was stirred and reacted at −10° C. for 30 minutes. Saturated Na₂CO₃ aqueous solution (5 mL) was added to quench the reaction, stirred for 10 minutes, and the organic phase was separated. The aqueous phase was extracted with dichloromethane (10 mL×2). The organic phases were combined, and dried over anhydrous sodium sulfate. After the filtration and concentration, the residue was purified by silica gel column chromatography to give 60 mg of a white solid, with a yield of 44.9%. LC-MS(APCI): m/z=561.2 (M+1)⁺. ¹H NMR (400 MHz, CDCl₃) δ 9.72 (s, 1H), 9.54 (br s, 1H), 8.75 (s, 1H), 8.49 (d, J=3.9 Hz, 1H), 7.97-7.92 (m, 3H), 7.51-7.41 (m, 4H), 6.82 (s, 1H), 6.52 (d, J=12.6 Hz, 1H), 6.38-6.32 (m, 1H), 5.88 (d, J=7.8 Hz, 1H), 4.01 (s, 3H), 3.91 (t, J=3.3 Hz, 4H), 2.91 (t, J=3.3 Hz, 4H), 2.38 (s, 2H).

Example 6

Preparation of N-(5-((4-(4-((bis(methyl-d₃)amino) methyl)-3-(phenyl-d₅)-1H-pyrazol-1-yl)pyrimidin-2-yl)amino)-4-methoxy-2- morpholinophenyl)acryl-amide (Compound T-6)

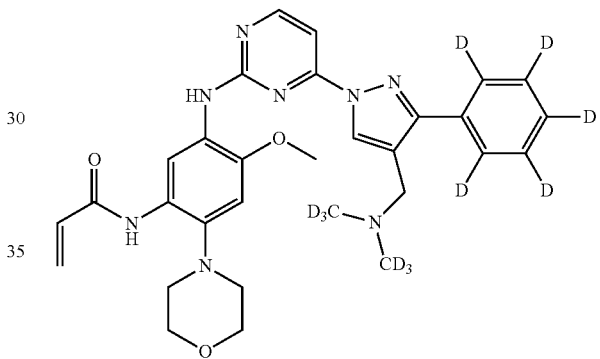

T-6

The following routes are used for synthesis:

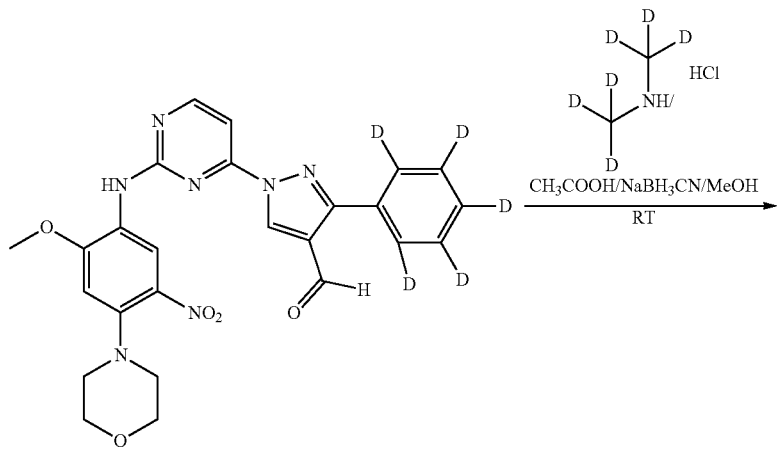

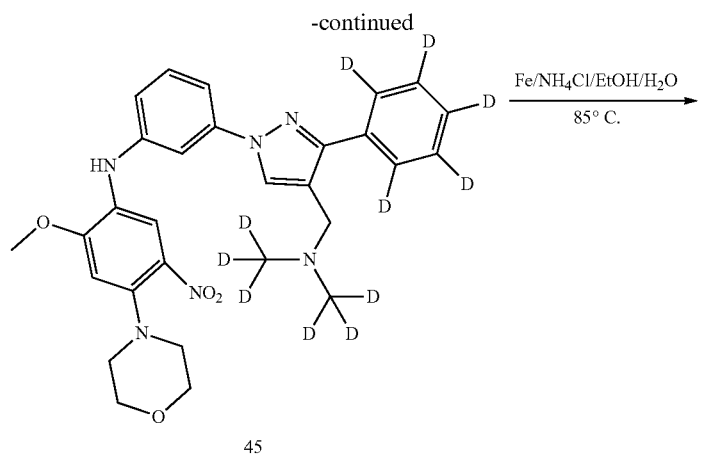

45

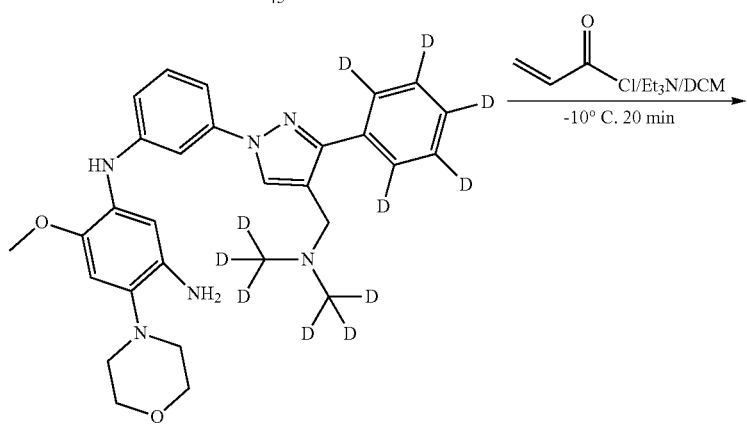

46

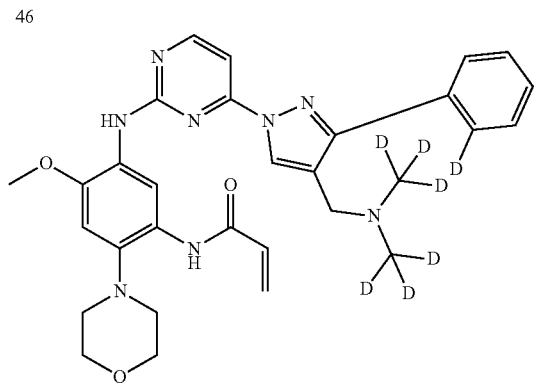

T-6

Step 1 Synthesis of Compound 45.

Dimethylamine-d₆ hydrochloride (0.75 mmol, 65 mg) and methanol (5 mL) were sequentially added into a 50 mL three-necked flask equipped with a magnetic stirrer, and stirred to dissolve. Granular NaOH (0.75 mmol, 30 mg) was added and stirred at room temperature for 30 minutes. Then, compound 21 (190 mg, 0.377 mmol) and glacial acetic acid (2 drops) were added, stirred and reacted at room temperature for 30 minutes. Sodium cyanoborohydride (0.75 mmol, 46 mg) was added afterwards, and stirred overnight at room temperature under nitrogen. The reaction solution was concentrated and purified by silica gel column chromatography to give 150 mg of a white solid, with a yield of 74.6%. LC-MS(APCI): m/z=542.2 (M+1)⁺. NMR (400 MHz, DMSO-d₆) δ 8.92 (s, 1H), 8.61-8.58 (m, 3H), 7.37 (d, J=3.9 Hz, 1H), 6.88 (s, 1H), 4.02 (s, 3H), 3.77 (t, J=3.3 Hz, 4H), 3.09 (t, J=3.3 Hz, 4H).

Step 2 Synthesis of Compound 46.

A mixture of ethanol/water (10 mL, 2/1) and compound 45 (150 mg, 280 μmol) were added to a 50 mL single-necked flask equipped with a magnetic stirrer and a condenser. Reduced iron powder (209 mg, 3.75 mmol) and ammonium chloride (100 mg, 1.87 mmol) were added under stirring. The temperature was raised to 85° C. under nitrogen, at which the resulting mixture was stirred and reacted for 1 h. The mixture was cooled to room temperature, and the insoluble solid was filtered off. The organic solvent was evaporated under reduced pressure, and the residue was extracted with ethyl acetate (15 mL×3). The organic phases were combined, dried over anhydrous sodium sulfate, filtered and concentrated to give 120 mg of a brown solid, with a yield of 85.2%. LC-MS(APCI): m/z=512.2 (M+1)⁺.

Step 3 Synthesis of Compound T-6.

Dry dichloromethane (10 mL) and compound 46 (120 mg, 241 µmol) were added into a 50 mL three-necked flask equipped with a magnetic stirrer. The resulting mixture was stirred to dissolve, cooled to −10° C., and triethylamine (105 mg, 1.04 mmol) was added. A solution of acryloyl chloride (23 mg, 260 µmol) in dichloromethane (1 mL) was slowly added dropwise under nitrogen, after which, the resulting mixture was stirred and reacted at −10° C. for 30 minutes. Saturated $Na_2CO_3$ aqueous solution (5 mL) was added to quench the reaction, stirred for 10 minutes, and the organic phase was separated. The aqueous phase was extracted with dichloromethane (10 mL×2). The organic phases were combined, and dried over anhydrous sodium sulfate. After the filtration and concentration, the residue was purified by silica gel column chromatography to give 60 mg of a white solid, with a yield of 44.9%. LC-MS(APCI): m/z=566.2 (M+1)⁺. $^1$H NMR (400 MHz, $CDCl_3$) δ 9.72 (s, 1H), 8.75 (s, 1H), 8.49 (d, J=3.9 Hz, 1H), 7.93 (s, 1H), 7.47 (d, J=4.2 Hz, 1H), 6.82 (s, 1H), 6.52 (d, J=12.6 Hz, 1H), 6.35 (dd, J1=12.9 Hz, J2=7.8 Hz, 1H), 5.88 (d, J=7.8 Hz, 1H), 3.94 (s, 3H), 3.91 (t, J=3.3 Hz, 4H), 2.91 (t, J=3.3 Hz, 4H).

Biological Activity Assay

The compounds obtained in the above examples were subjected to the biological evaluation to determine their biological activities. In addition, the anti-proliferative activity of these compounds were screened in the human A431 skin cancer cells, as well as the human NCI-H1975 and HCC827 lung cancer cell lines, and the activity was demonstrated to be in the range of <10 nM. The cytotoxicity or the growth inhibition effect of the compounds on the tumor cells of interest was evaluated.

(1) Kinase Inhibition

The biological activity of the compounds in examples 1 to 6 was determined by testing their ability to inhibit a variety of protein kinases of interest. The assays have shown that these compounds show potent inhibitory activity against EGFR kinases. The specific methods are as follows:

Reagents and Materials:

WT EGFR (Cana, Cat. No. 08-115), EGFR [L858R] (Carna, Cat. No. 08-502), EGFR [L858R/T790M] (Carna, Cat. No. 08-510), ATP (Sigma, Cat. No. A7699-1G), DMSO (Sigma, Cat. No. D2650), 96-well plate (Corning, Cat. No. 3365), 384-well plate (Greiner, Cat. No. 784076), HTRF Kinase TK Kit (Cisbio, Cat. No. 62TK0PEJ), Erlotinib (Selleckchem, Cat. No. S7787), EGFR [d746-750] (Life Technologies, Cat. No. PV6178), 5× Kinase Buffer A (Life Technologies, Cat. No. PV3186), Kinase Tracer 199 (Life Technologies, Cat. No. PV5830), LanthaScreen® Eu-anti-GST antibody (Life Technologies, Cat. No. PV5594).

Specific Experimental Protocol:

Compound preparation: the test compound was dissolved in DMSO to make a 20 mM stock solution. Then, it was diluted in DMSO with a 3-fold series gradient dilution for 10 times. The dilutions were diluted 10 fold with buffer when dosing.

WT EGFR and EGFR [L858R/T790M] kinase assay: WT EGFR or EGFR [L858R/T790M] kinase was mixed with different concentrations of pre-diluted compounds for 10 minutes in 5× Kinase Buffer A in duplicate. The corresponding substrate and ATP were added and reacted at room temperature for 20 minutes (in which a negative and a positive control were set: the negative control is blank and the positive control is AZD9291). After the reaction, the detection reagent (the reagent in the HTRF Kinase TK kit) was added, and after incubation at room temperature for 30 minutes, the enzyme activity in the presence of the compounds of the present disclosure at each concentration was measured by an Evnvision microplate reader, and the inhibition of the enzyme by the compound at each concentrations were calculated. The inhibitions of the enzyme activity by the compounds at different concentrations were then fitted using Graphpad 5.0 software according to the four-parameter equation, and the $IC_{50}$ values were calculated.

The compounds of the present disclosure and the non-deuterated compound N-(5-(4-(4-(dimethylamino)methyl)-3-phenyl-1H-pyrazol-1-yl)pyrimidin-2-ylamino)-4-methoxy-2-morpholinophenyl)acrylamide (compound T-0) were tested in the above kinase inhibition assay, and the compounds of the present disclosure were found to have potent activity against EGFR [L858R/T790M] and superior selectivity over WT EGFR. The results for the representative example compounds are summarized in Table 1 below.

TABLE 1

| Example number | WT EGFR $IC_{50}$(nM) | EGFR(L858R/T790M) $IC_{50}$(nM) |
| --- | --- | --- |
| T-0 | <2 | <0.3 |
| T-1 | <2 | <0.3 |
| T-2 | <2 | <0.3 |
| T-3 | <2 | <0.3 |
| T-4 | <2 | <0.3 |
| T-6 | <2 | <0.3 |

(2) Cytotoxic Effect

The in vitro anti-proliferative activity of the compounds of the present disclosure against two types of tumor cells that cultured in vitro was tested by MTS method. The experimental results show that the compounds of the present disclosure have inhibitory effect on the in vitro proliferation of cancer cells that cultured in vitro; wherein the inhibition of in vitro proliferation of king cancer cells is stronger than that of skin cancer cells.

Cell line: Skin cancer cell line A431 (purchased from the American Type Culture Collection (ATCC)); lung cancer cells NCI-H1975 (purchased from the American Type Culture Collection (ATCC)) and HCC827 (purchased from the American Type Culture Collection (ATCC)). All of the cells were cultured in RPMI1640 medium containing 10% fetal bovine serum, 100 U/ml penicillin, and 100 µg/ml streptomycin.

Reagents and materials: RPMI-1640 (GIBCO, Cat. No. A10491-01); fetal bovine serum (GIBCO, Cat. No. 10099141); 0.25% trypsin-EDTA (GIBCO, Cat. No. 25200); penicillin-streptomycin, liquid (GIBCO, Cat. No. 15140-122); DMSO (Sigma, Cat. No. D2650); MTS Test Kit (Promega, Cat. No. G3581), 96-well plate (Corning, Cat. No. 3365).

Specific Experimental Protocol:

Compound preparation: the test compound was dissolved in DMSO to make a 20 mM stock solution and stored at −20° C. It was diluted in DMSO with a 3-fold series gradient dilution for 10 times. The dilutions were diluted 4 fold with cell culture medium.

MTS cell viability assay: cells in logarithmic growth phase was digested with 0.25% trypsin-EDTA, and 150 µl of the cells was inoculated in 96-well plates at an optimized density. After 24 hours, the compound diluted 4 fold by adding the medium, 50 µl/well (generally 10 Concentrations were selected: 100, 33.3, 11.1, 3.70, 1.23, 0.412, 0.137, 0.0457, 0.0152, 0.00508 µM). A well added with the same volume of 0.5% DMSO was used as a control. After the cells were cultured for further 72 hours, the cell viability was detected with MTS.

Specific procedure: cells were adhered, the medium was discarded, and a mixture containing 20 μL MTS and 100 μL medium was added to each well. The OD490 was detected after being placed in the incubator for 1-4 hours, and the OD650 value was used as a reference. A dose-effect curve was prepared using GraphPad Prism software and $IC_{50}$ was calculated.

The compounds of the present disclosure and the non-deuterated compound N-(5-(4-(4-(dimethylamino)methyl)-3-phenyl-1H-pyrazol-1-yl)pyrimidin-2-ylamino)-4-methoxy-2-morpholinophenyl)acrylamide (compound T-0) were tested in the above cytotoxicity assay, and the compounds of the present disclosure were found to have potent activity against lung cancer cells NCI-H1975 and HCC827 and superior selectivity over skin cancer cells A431. The results of the in vitro inhibition of the proliferation of cancer cells by representative examples are summarized in Table 2 below.

TABLE 2

| Example number | A431(WT) $IC_{50}$(nM) | HCC827(Del19) $IC_{50}$(nM) | H1975(L858R/T790M) $IC_{50}$(nM) |
|---|---|---|---|
| T-0 | 200~450 | 4.2 | 4.7 |
| T-1 | 200~450 | 1.56 | 3.62 |
| T-2 | 200~450 | 1.98 | 3.57 |
| T-3 | 200~450 | 2.27 | 4.53 |
| T-4 | 200~450 | 2.50 | 5.02 |
| T-6 | 200~450 | 2.00 | 4.23 |

(3) Metabolic Stability Evaluation

Microsome assay: human liver microsomes: 0.5 mg/mL, Xenotech; rat liver microsomes: 0.5 mg/mL, Xenotech; mouse liver microsomes: 0.5 mg/mL, Xenotech; coenzyme (NADPH/NADH): 1 mM, Sigma Life Science; magnesium chloride: 5 mM, 100 mM phosphate buffer (pH 7.4).

Preparation of stock solutions: Powder of the example compounds were accurately weighed and dissolved in DMSO to 5 mM.

Preparation of phosphate buffer (100 mM, pH7.4): A pre-prepared 0.5 M potassium dihydrogen phosphate (150 mL) was mixed with 0.5 M dibasic potassium phosphate (700 mL). The pH of the mixture was adjusted to 7.4 with 0.5 M dibasic potassium phosphate solution. The mixture was diluted 5-fold with ultrapure water before use, and magnesium chloride was added to obtain a phosphate buffer (100 mM) containing 100 mM potassium phosphate, 3.3 mM magnesium chloride, pH 7.4.

A NADPH regeneration system solution (containing 6.5 mM NADP, 16.5 mM G-6-P, 3 U/mL G-6-P D, 3.3 mM magnesium chloride) was prepared and placed on wet ice prior to use.

Preparation of stop solution: an acetonitrile solution containing 50 ng/mL propranolol hydrochloride and 200 ng/mL tolbutamide (internal standard). 25057.5 μL of phosphate buffer (pH 7.4) was taken into three 50 mL centrifuge tubes, to which 812.5 μL of human, rat and mouse liver microsomes were added respectively, and mixed to obtain the liver microsome dilutions with a protein concentration of 0.625 mg/mL. Incubation of the samples: The stock solutions of the respective compounds were respectively diluted to 0.25 mM with an aqueous solution containing 70% acetonitrile, and used as a working solution, ready for use. 398 μL of the dilutions of human liver, rat liver and mouse liver microsomes were added to 96-well incubation plates (N=2), respectively, and 2 μL of 0.25 mM working solution was added respectively and mixed.

Metabolic stability assay: 300 μL of pre-chilled stop solution was added to each well of 96-well deep well plates and placed on ice as stop plates. The 96-well incubation plates and NADPH regeneration system were placed in a 37° C. water bath box, shaken at 100 rpm and pre-incubated for 5 min. 80 μL of incubation solution was taken out from each well of the incubation plates and added to the stop plates, mixed, and replenished with 20 μL of NADPH regeneration system solution as a 0-min sample. 80 μL of NADPH regeneration system solution was added to each well of the incubation plates to start the reaction and start counting. The corresponding compounds had a reaction concentration of 1 μM and the protein concentration was 0.5 mg/mL. Separately, 100 μL of the reaction solutions was taken at 10, 30, and 90 min reaction, respectively, added to stop plates, and vortexed for 3 minutes to terminate the reaction. The stop plates were centrifuged at 5000 ×g at 4° C. for 10 min. 100 μL of the supernatant was added to a 96-well plate to which 100 μL of distilled water was previously added, mixed, and analyzed by LC-MS/MS.

Data analysis: The peak areas of the corresponding compounds and internal standard were detected by LC-MS/MS system, and the ratio of the peak area of the compounds to the internal standard was calculated. The slope was measured by plotting the natural logarithm of the percent of compound remaining versus time, and $t_{1/2}$ and $CL_{int}$ were calculated according to the equation below, where V/M equals to 1/protein concentration.

$$t_{1/2} = -\frac{0.693}{\text{slope}}, \quad CL_{int} = \frac{0.693}{t_{1/2}} \cdot \frac{V}{M}, \quad t_{1/2}(\text{min}); CL_{int}(\mu L/\text{min/mg}).$$

The metabolic stability of the compounds in human, rat and mouse liver microsomes was evaluated by simultaneously testing and comparing the compounds disclosed herein and the non-deuterated compound. The half-life and liver intrinsic clearance as indicators of metabolic stability are shown in the table. In the table, the non-deuterated compound N-(5-(4-(4-(dimethylamino)methyl)-3-phenyl-1H-pyrazol-1-yl)pyrimidin-2-ylamino)-4-methoxy-2-morpholinophenyl)acrylamide (compound T-0) was used as a control sample. As shown in Table 3, in the human, rat and mouse liver microsome assays, compared with the non-deuterated compound T-0, the compounds of the present disclosure can significantly improve the metabolic stability.

TABLE 3

| No. | Human liver microsome assay | | Rat liver microsome assay | | | |
|---|---|---|---|---|---|---|
| | $t_{1/2}$ | $CL_{int}$ | $t_{1/2}$ | $CL_{int}$ | $t_{1/2}$ | $CL_{int}$ |
| T-0 | 67.1 | 20.6 | 45.3 | 30.6 | 50.4 | 27.5 |
| T-1 | 100.0 | 13.8 | 78.5 | 17.7 | | |
| T-2 | 98.7 | 14.0 | 83.5 | 16.6 | | |
| T-3 | 81.6 | 17.0 | 62.7 | 22.1 | >145 | <9.6 |
| T-4 | 91.0 | 15.2 | 68.3 | 20.3 | 125.4 | 11.4 |
| T-5 | 79.4 | 17.4 | 57.4 | 24.1 | | |
| T-6 | 97.0 | 14.3 | 74.9 | 18.5 | | |

(4) Pharmacokinetic Experiment in Rats

Six male Sprague-Dawley rats, 7 to 8 weeks old, weighing approximately 210 g, were divided into 2 groups with 3 rats in each group. The pharmacokinetic differences were compared after administering to the rats a single dose of compounds through vein (in vein 0.5 mg/kg) or mouth (orally 10 mg/kg).

The rats were fed with standard feed, given water, and fasted 16 hours before the experiment. The drugs were dissolved with PEG400 and dimethyl sulfoxide. Orbital blood was collected at the time point of 0.083, 0.25, 0.5, 1, 2, 4, 6, 8, 12 and 24 hours after administration.

The rats were anesthetized for a short time after inhaling ether, and 300 μL of blood sample was collected from the orbit and put into a test tube, which contains 30 μL of 1% heparin salt solution. The test tubes were dried overnight at 60° C. prior to use. After the blood sample collection at the last time point, the rats were killed after the ether anesthesia.

Immediately after the blood sample collection, the test tubes were gently inverted at least 5 times to ensure the fully mixing and placed them on ice. The blood samples were centrifuged at 4° C., 5000 rpm for 5 minutes to separate the plasma from the red blood cells. 100 μL of plasma was pipetted into a clean plastic centrifuge tube, with the name of the compound and time point on it. The plasma was stored at −80° C. before analysis, and LC-MS/MS was used to determine the concentration of the compounds disclosed herein in plasma. Pharmacokinetic parameters were calculated based on the plasma concentrations of each animal at different time points.

The non-deuterated compound N-(5-(4-(4-(dimethylamino)methyl)-3-phenyl-1H-pyrazol-1-yl)pyrimidin-2-ylamino)-4-methoxy-2-morpholinophenyl)acrylamide (compound T-0) was used as a positive control in this experiment. The experimental results are shown in Table 4.

TABLE 4

|  | T-0 | | T-3 | |
| --- | --- | --- | --- | --- |
|  | IV | PO | IV | PO |
| $T_{max}$(h) | 0.08 | 1.33 | 0.08 | 4.00 |
| $C_{max}$(ng/mL) | 322.7 | 115.3 | 298.7 | 119.6 |
| $AUC_{last}$ (h*ng/mL) | 476.7 | 1595.3 | 435.8 | 1648.3 |
| $AUC_{INF\_pred}$ (h*ng/mL) | 497.7 | 1798.5 | 455.7 | 1923.6 |
| $MRT_{INF\_pred}$ (h) | 2.95 | 9.19 | 3.34 | 8.67 |
| $Vz_{\_pred}$ (L/kg) | 5.73 | 61.56 | 5.71 | 56.99 |
| $Cl_{\_pred}$(L/h/kg) | 1.05 | 5.65 | 1.11 | 5.28 |
| $T_{1/2}$ (h) | 3.78 | 7.55 | 3.56 | 7.48 |
| F(%) | | 16.73 | | 18.91 |

The experimental results showed that the compounds disclosed herein have better pharmacokinetic properties. For example, orally administering compound T-3 and compound T-0 to the rats at the same time, compound T-3 was found to have better metabolic parameters—maximum plasma exposure concentration ($C_{max}$), plasma exposure ($AUC_{last}$) and oral availability (F %).

The above content is a further detailed description disclosed herein in combination with specific preferred embodiments, and it cannot be assumed that the specific implementation disclosed herein is limited to these descriptions. For a person of ordinary skill in the art to which the present disclosure belongs, a number of simple deductions or substitutions can be made without departing from the concept disclosed herein, and should all be considered as falling within the protection scope disclosed herein.

The invention claimed is:

1. An aminopyrimidine compound of formula (I), or a polymorph, pharmaceutically acceptable salt, prodrug, stereoisomer, isotopic variants, hydrate or solvate thereof:

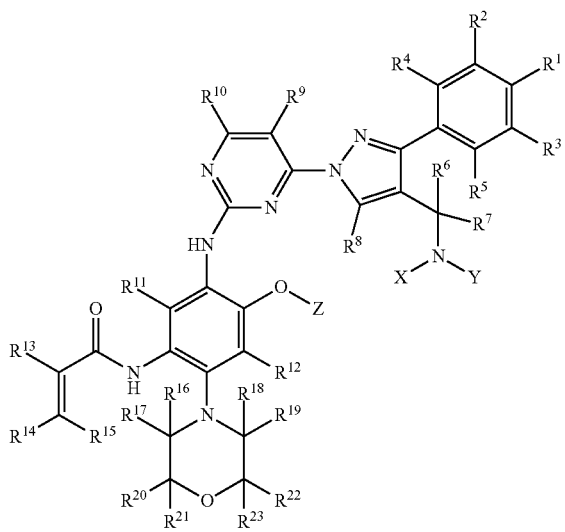

wherein, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$ and $R^{23}$ are independently selected from hydrogen, deuterium and halogen;

X, Y and Z are independently selected from the group consisting of $CH_3$, $CH_2D$, $CHD_2$ and $CD_3$;

with the proviso that the aminopyrimidine compound described above contains at least one deuterium atom.

2. The aminopyrimidine compound of formula (I), or the polymorph, pharmaceutically acceptable salt, prodrug, stereoisomer, isotopic variants, hydrate or solvate thereof according to claim 1, wherein $R^9$, $R^{10}$, $R^{11}$, $R^{12}$, $R^{13}$, $R^{14}$ and $R^{15}$ are hydrogen.

3. The aminopyrimidine compound of formula (I), or the polymorph, pharmaceutically acceptable salt, prodrug, stereoisomer, isotopic variants, hydrate or solvate thereof according to claim 2, wherein $R^{16}$, $R^{17}$, $R^{18}$, $R^{19}$, $R^{20}$, $R^{21}$, $R^{22}$ and $R^{23}$ are hydrogen.

4. The aminopyrimidine compound of formula (I), or the polymorph, pharmaceutically acceptable salt, prodrug, stereoisomer, isotopic variants, hydrate or solvate thereof according to claim 3, wherein $R^1$, $R^2$, $R^3$, $R^4$ and $R^5$ are hydrogen.

5. The aminopyrimidine compound of formula (I), or the polymorph, pharmaceutically acceptable salt, prodrug, stereoisomer, isotopic variants, hydrate or solvate thereof according to claim 3, wherein $R^6$, $R^7$ and $R^8$ are hydrogen.

6. The aminopyrimidine compound of formula (I), or the polymorph, pharmaceutically acceptable salt, prodrug, stereoisomer, isotopic variants, hydrate or solvate thereof according to claim 3, wherein X and Y are $CH_3$.

7. The aminopyrimidine compound of formula (I), or the polymorph, pharmaceutically acceptable salt, prodrug, stereoisomer, isotopic variants, hydrate or solvate thereof according to claim 3, wherein Z is $CD_3$.

8. The aminopyrimidine compound of formula (I), or the polymorph, pharmaceutically acceptable salt, prodrug, stereoisomer, isotopic variants, hydrate or solvate thereof according to claim 3, wherein X and Y are independently methyl substituted with one or more deuteriums.

9. The aminopyrimidine compound of formula (I), or the polymorph, pharmaceutically acceptable salt, prodrug, stereoisomer, isotopic variants, hydrate or solvate thereof according to claim 3, wherein $R^1$, $R^2$, $R^3$, $R^4$ and $R^5$ are D.

10. The aminopyrimidine compound of formula (I), or the polymorph, pharmaceutically acceptable salt, prodrug, stereoisomer, isotopic variants, hydrate or solvate thereof according to claim 8, wherein $R^1$, $R^2$, $R^3$, $R^4$ and $R^5$ are D.

11. The aminopyrimidine compound of formula (I), or the polymorph, pharmaceutically acceptable salt, prodrug, stereoisomer, isotopic variants, hydrate or solvate thereof according to claim 3, wherein $R^6$, $R^7$ and $R^8$ are D.

12. The aminopyrimidine compound of formula (I), or the polymorph, pharmaceutically acceptable salt, prodrug, stereoisomer, isotopic variants, hydrate or solvate thereof according to claim 1, wherein the aminopyrimidine compound of formula (I) is selected from any one of the following structures:

Formula (1)

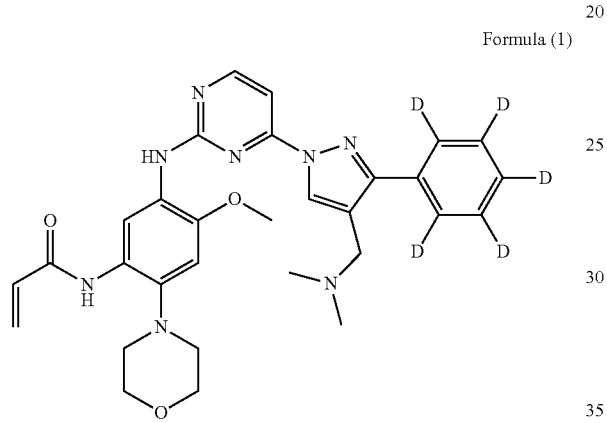

Formula (2)

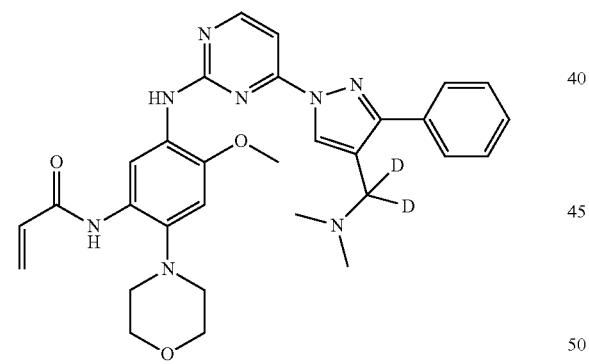

Formula (3)

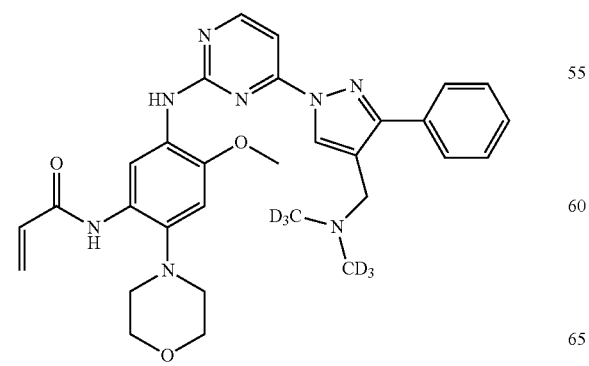

-continued

Formula (4)

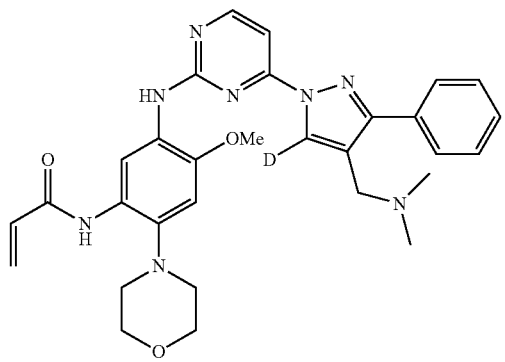

Formula (5)

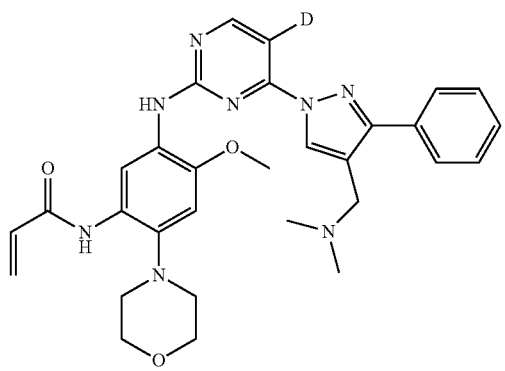

Formula (6)

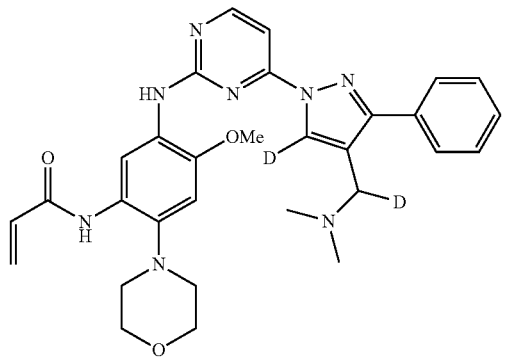

Formula (7)

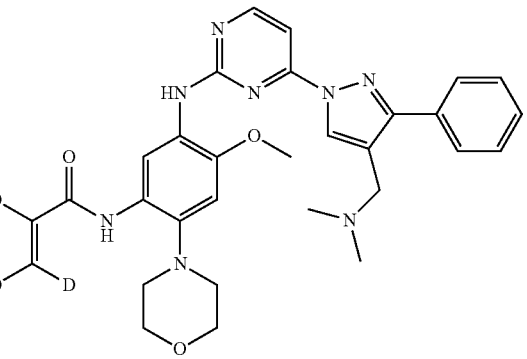

-continued
Formula (8)
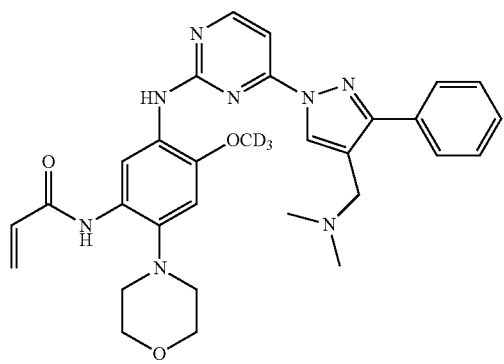
Formula (9)
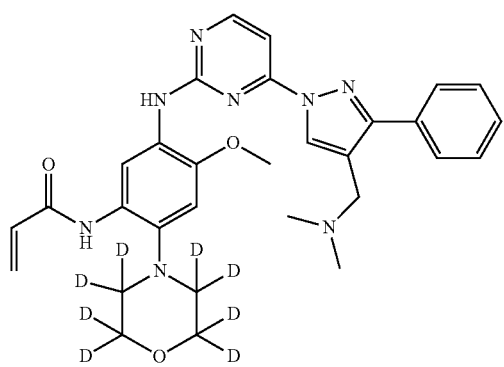
Formula (10)
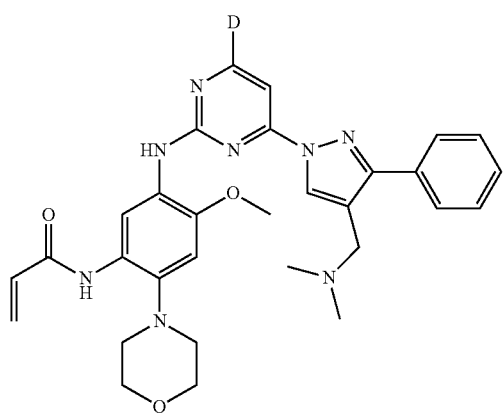
Formula (11)
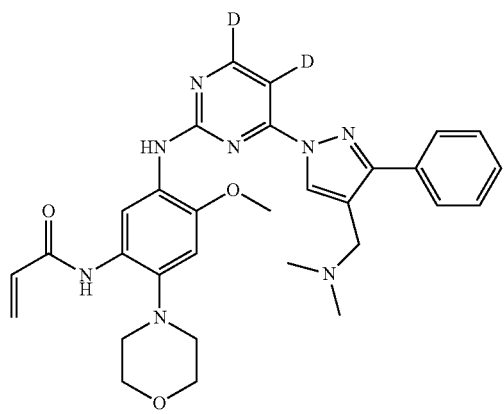
Formula (12)
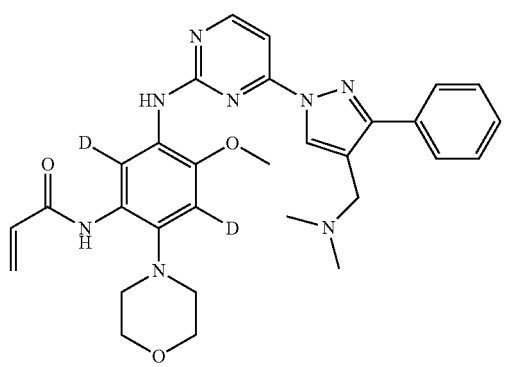
Formula (13)
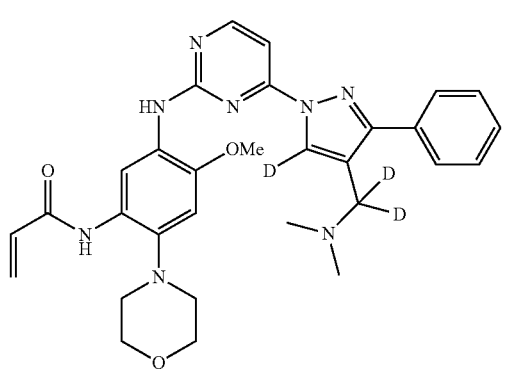
Formula (14)
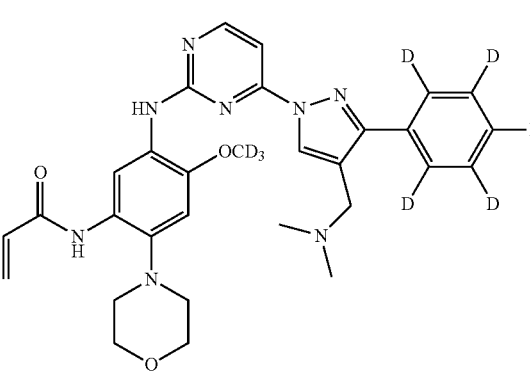
Formula (15)
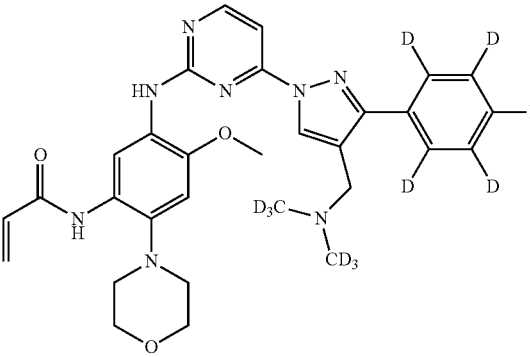

-continued
Formula (16)
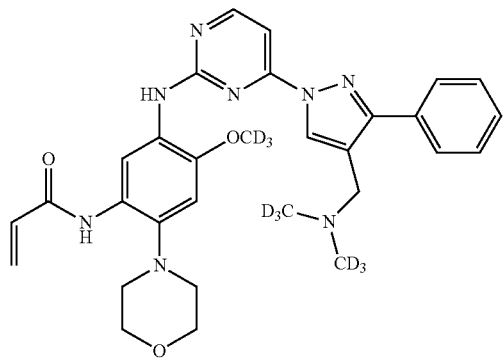
Formula (17)
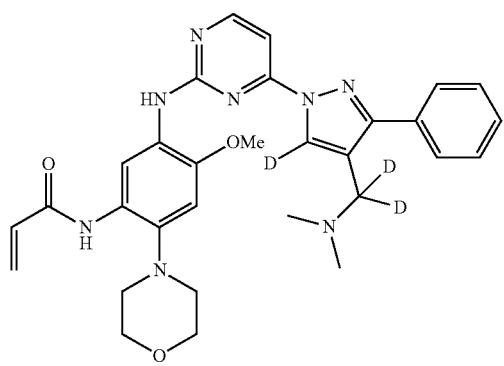
Formula (18)
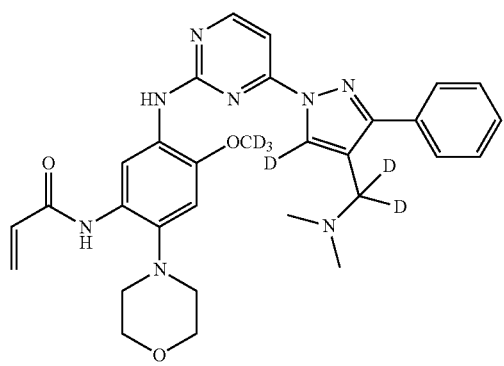
Formula (19)
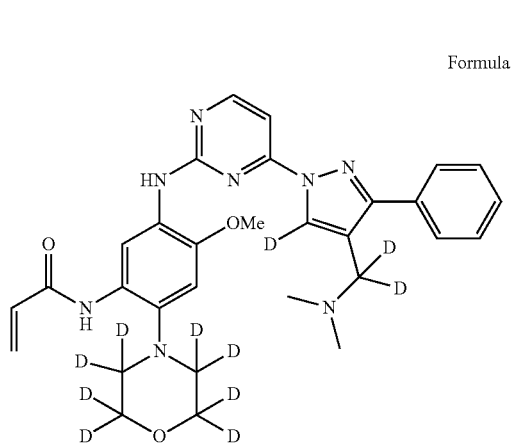
-continued
Formula (20)
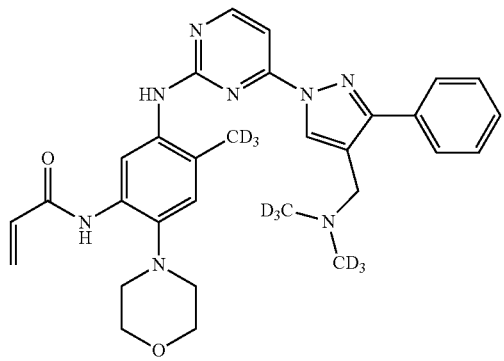
Formula (21)
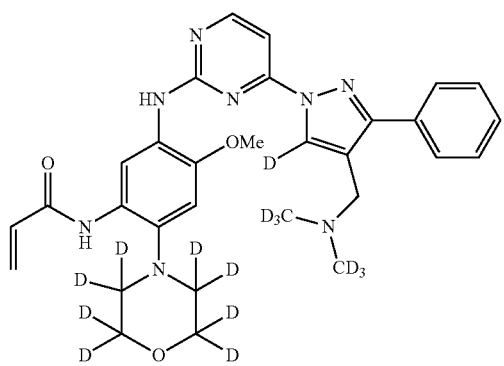
Formula (22)
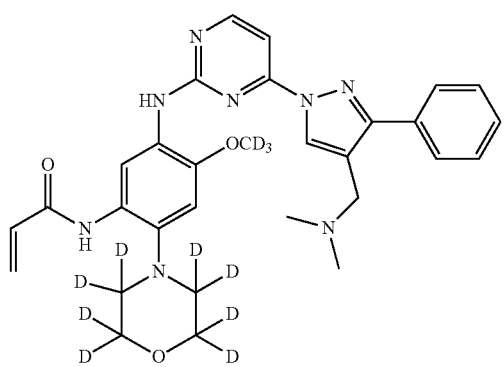
Formula (23)
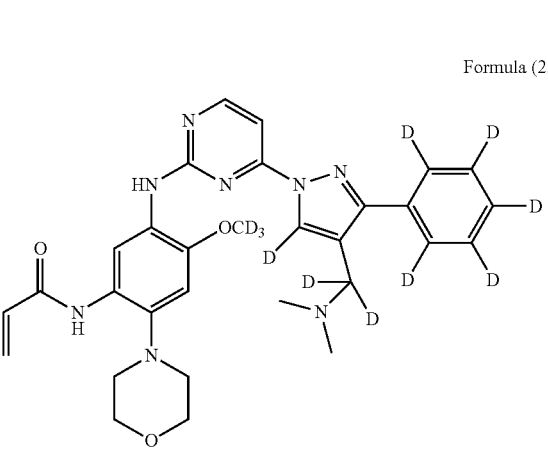

Formula (24)
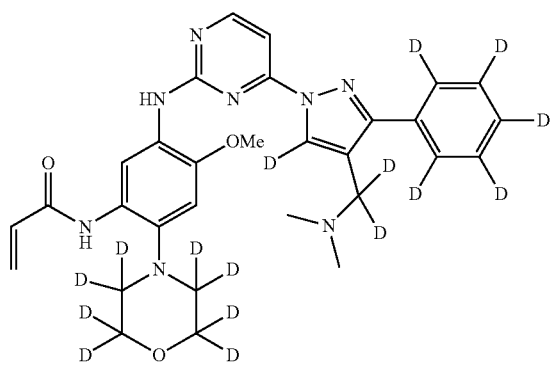
Formula (25)
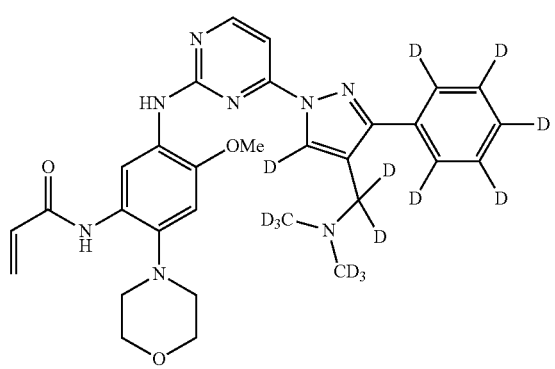
Formula (26)
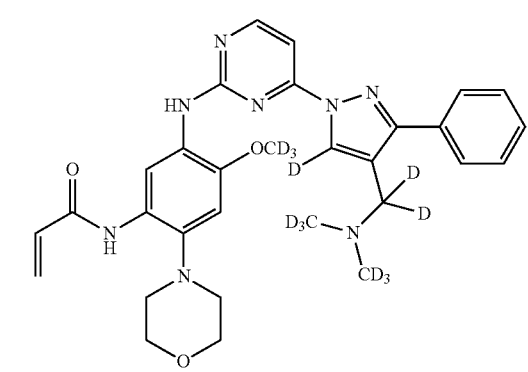
Formula (27)
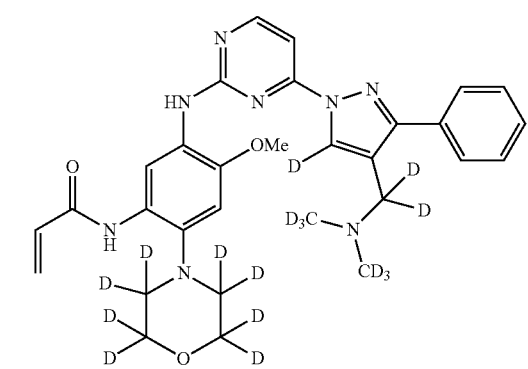
Formula (28)
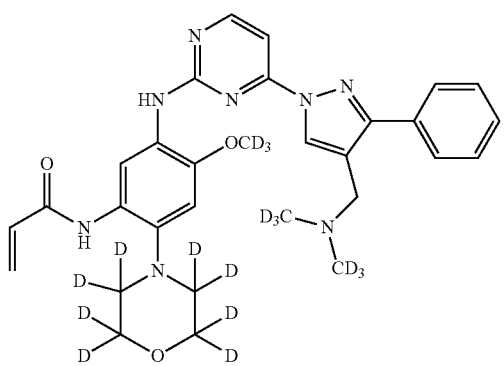
Formula (29)
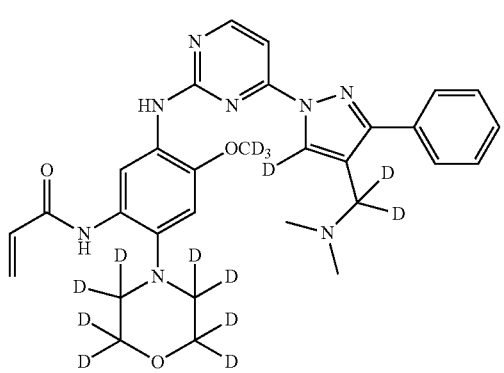
Formula (30)
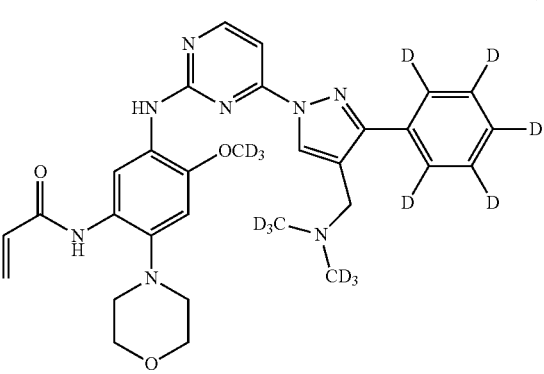
Formula (31)
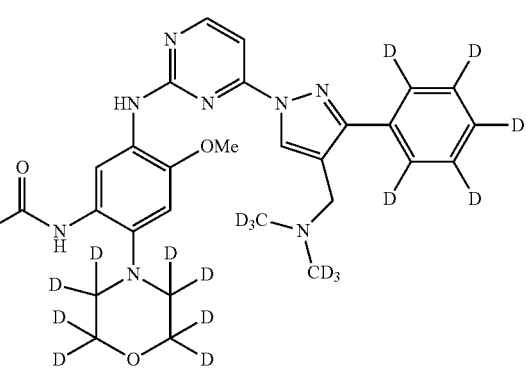

Formula (32)
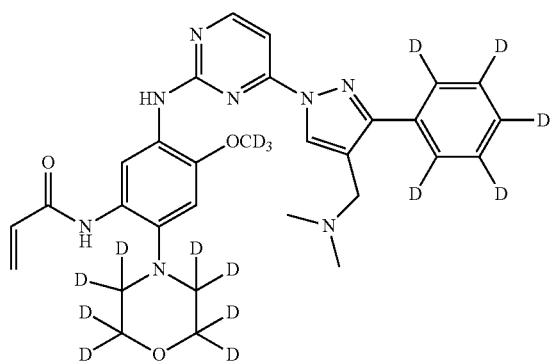
Formula (33)
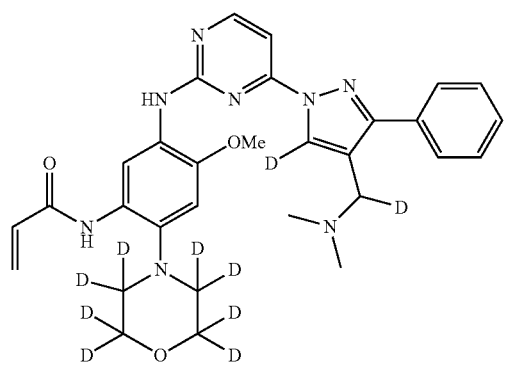
Formula (34)
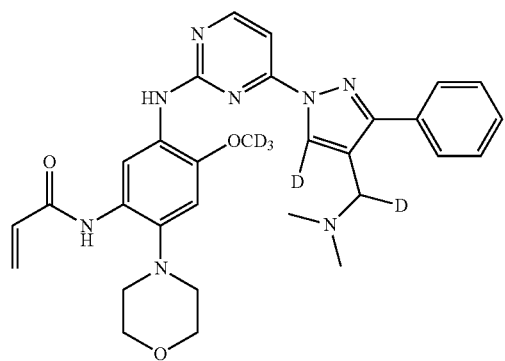
Formula (35)
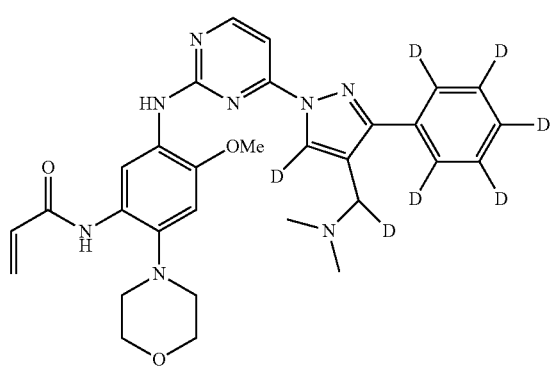
Formula (36)
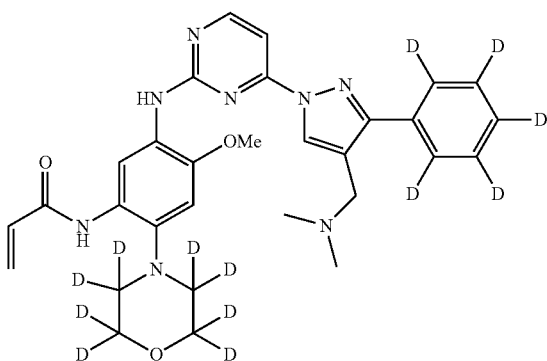
Formula (37)
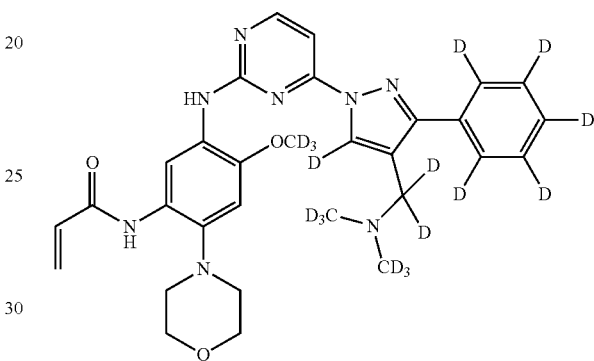
Formula (38)
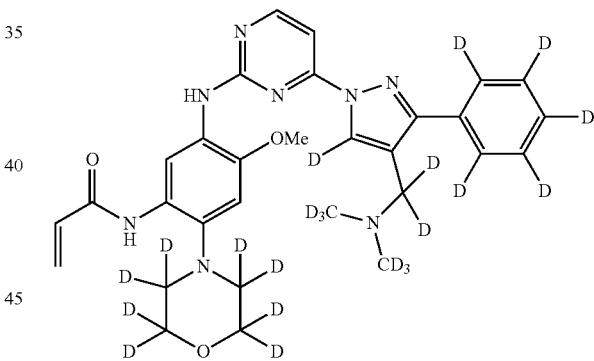
Formula (39)
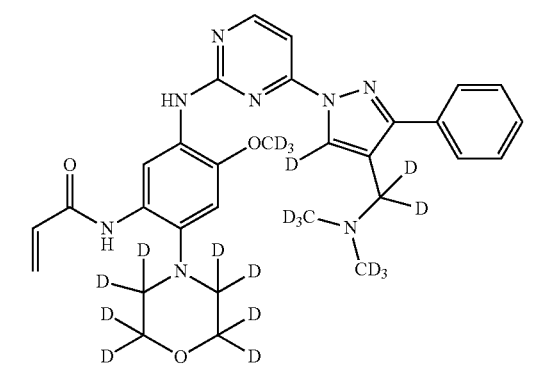

Formula (40)
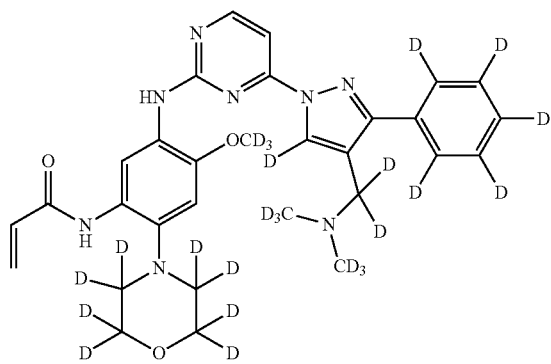
Formula (41)
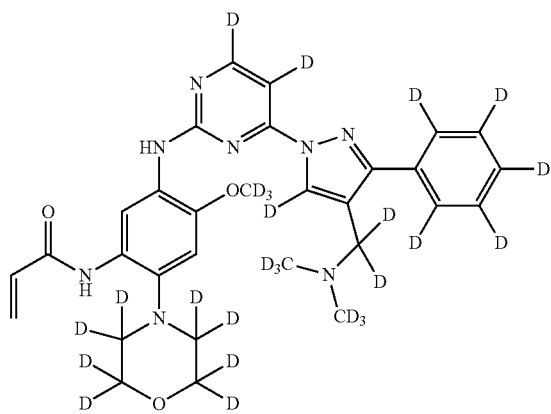
Formula (42)
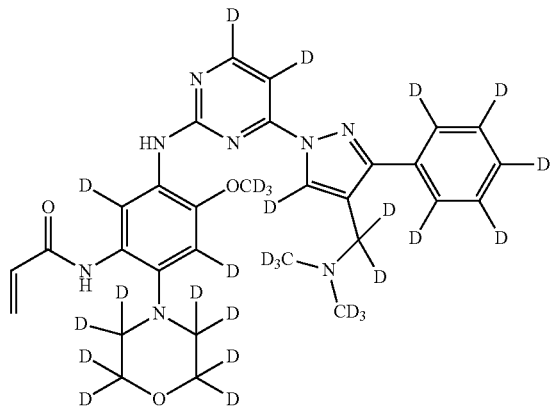
Formula (43)
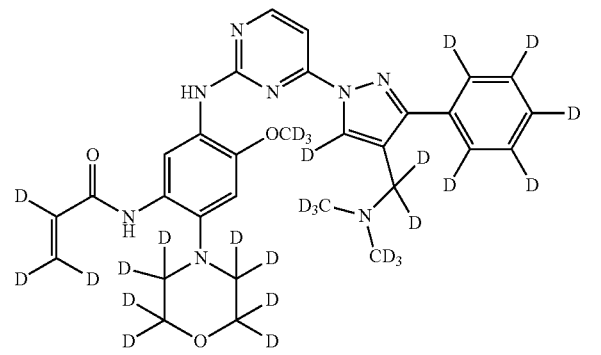
Formula (44)
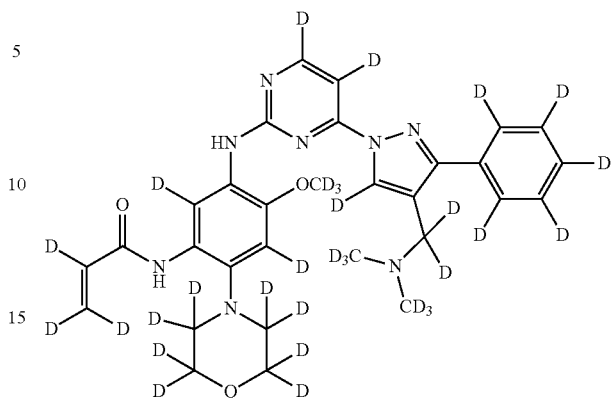
Formula (45)
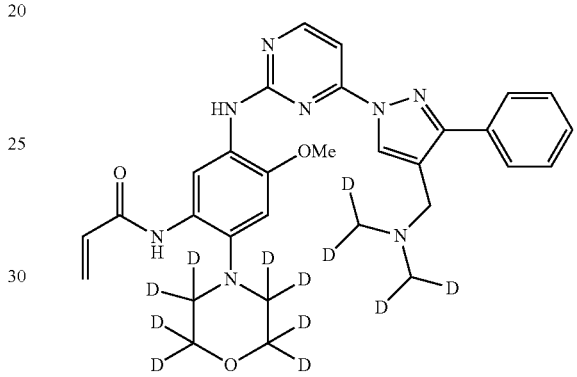
Formula (46)
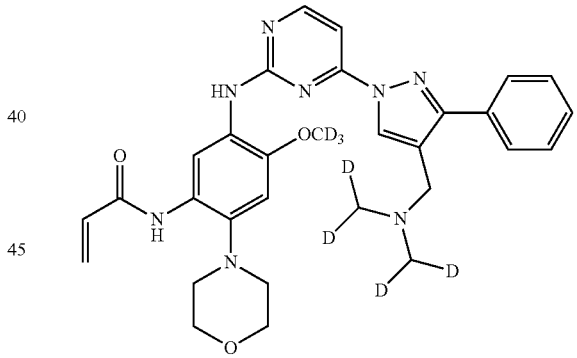
Formula (47)
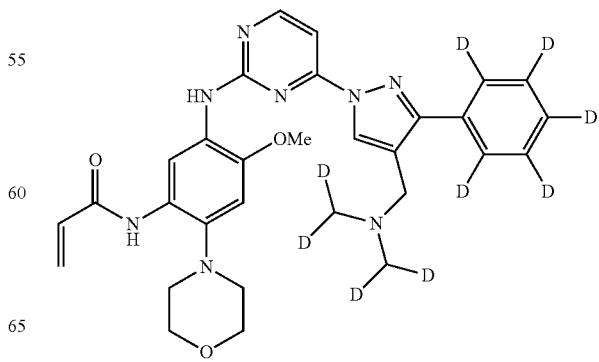

Formula (48)
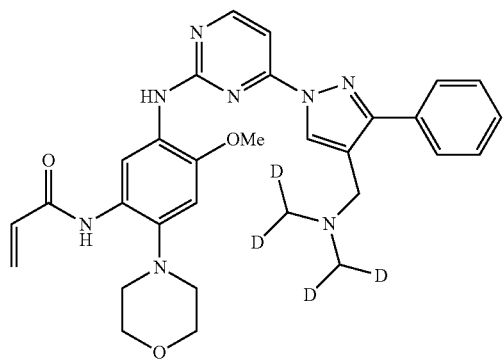
Formula (49)
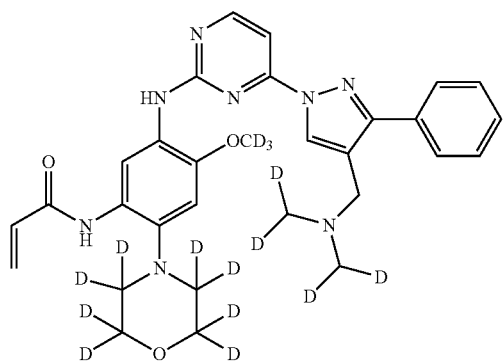
Formula (50)
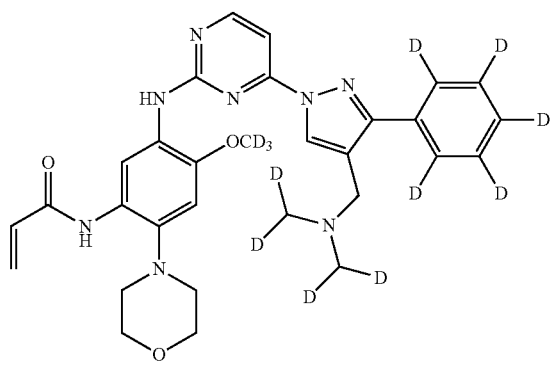
Formula (51)
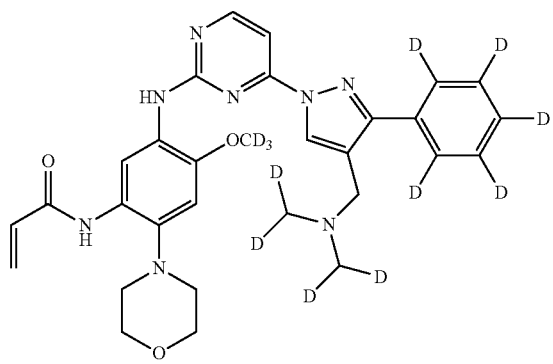
Formula (52)
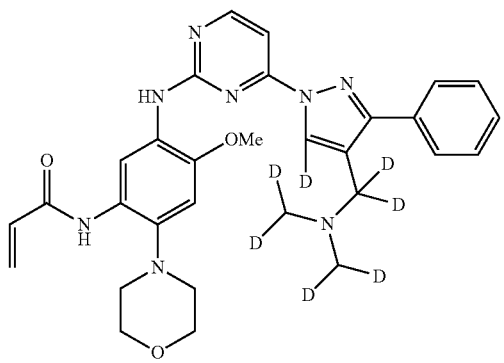
Formula (53)
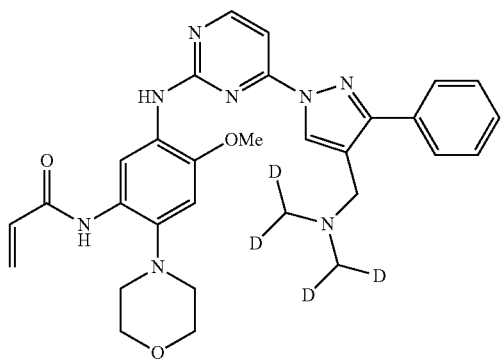
Formula (54)
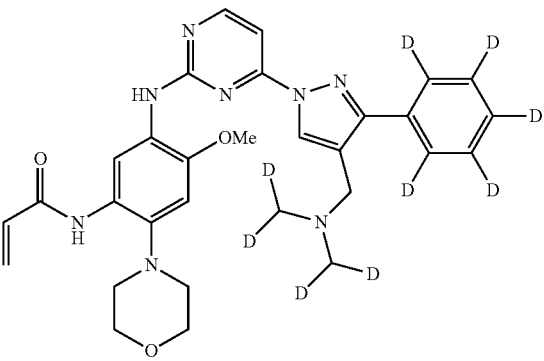
Formula (55)
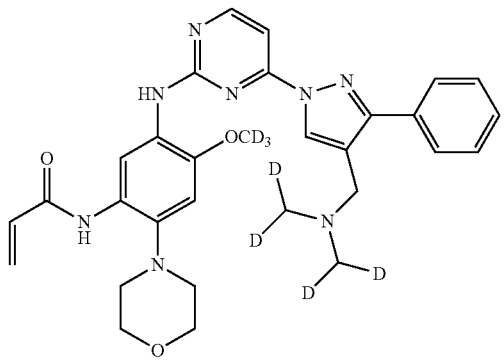

Formula (56)

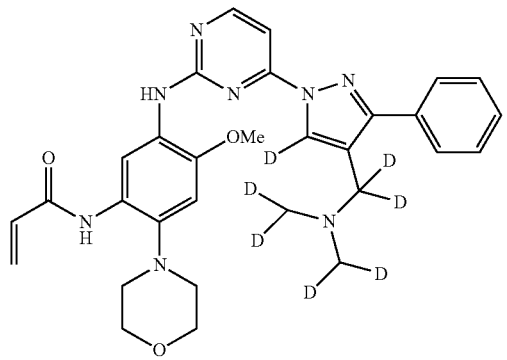

Formula (57)

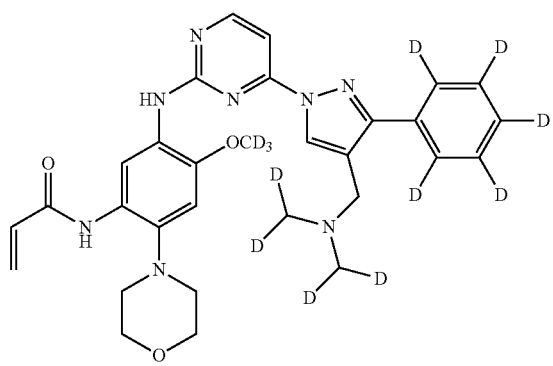

Formula (58)

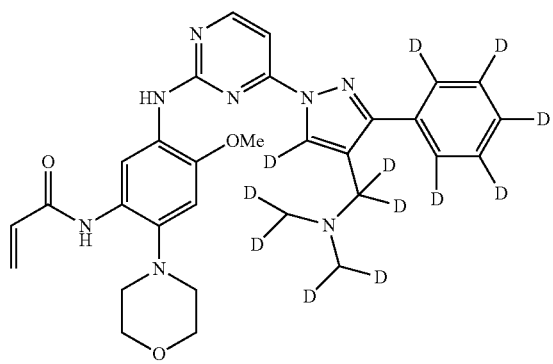

Formula (59)

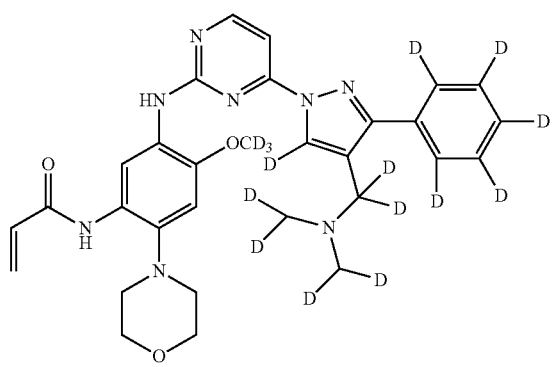

Formula (60)

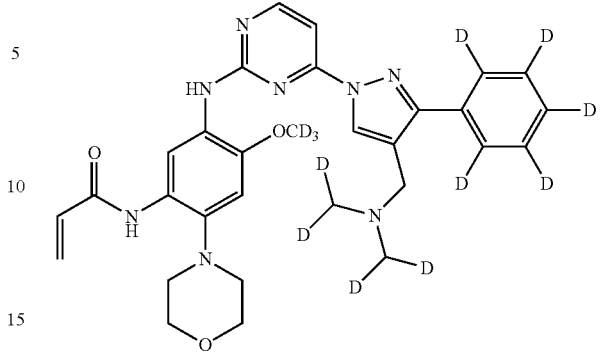

Formula (61)

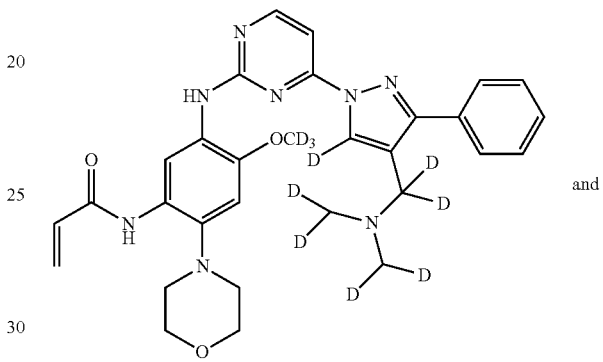

and

Formula (62)

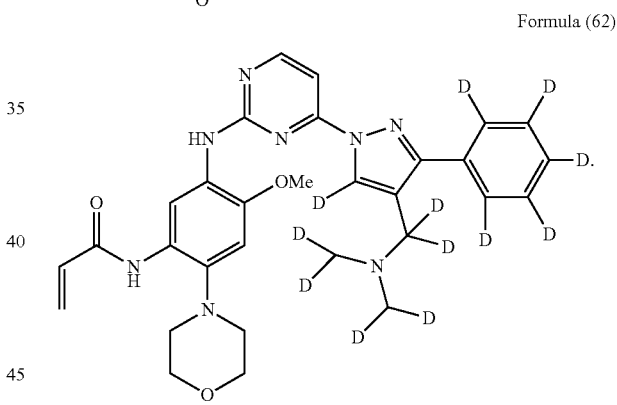

13. A pharmaceutical composition, comprising pharmaceutically acceptable excipient(s) and the aminopyrimidine compound of formula (I), or the polymorph, pharmaceutically acceptable salt, prodrug, stereoisomer, isotopic variants, hydrate or solvate thereof according to claim 1.

14. A method of treating non-small cell lung cancer (NSCLC) mediated by a mutant form of EGFR in a subject, comprising administering to the subject the aminopyrimidine compound of formula (I), or the polymorph, pharmaceutically acceptable salt, prodrug, stereoisomer, isotopic variants, hydrate or solvate thereof according to claim 1.

15. The method according to claim 14, wherein the mutant form of EGFR is del19, L858R or T790M.

16. The method according to claim 14, wherein the mutant form of EGFR is del19/T790M or L858R/T790M.

* * * * *